US010056548B2

(12) United States Patent
Pan et al.

(10) Patent No.: US 10,056,548 B2
(45) Date of Patent: Aug. 21, 2018

(54) EMITTER AND HOSTS WITH AROMATIC UNITS

(71) Applicant: Merck Patent GmbH, Darmstadt (DE)

(72) Inventors: Junyou Pan, Frankfurt am Main (DE); Martin Engel, Darmstadt (DE); Nils Koenen, Darmstadt (DE); Aurélie Ludemann, Frankfurt am Main (DE)

(73) Assignee: Merck Patent GmbH (DE)

( * ) Notice: Subject to any disclaimer, the term of this patent is extended or adjusted under 35 U.S.C. 154(b) by 340 days.

(21) Appl. No.: 14/434,583

(22) PCT Filed: Sep. 18, 2013

(86) PCT No.: PCT/EP2013/002806
§ 371 (c)(1),
(2) Date: Apr. 9, 2015

(87) PCT Pub. No.: WO2014/056573
PCT Pub. Date: Apr. 17, 2014

(65) Prior Publication Data
US 2015/0270489 A1    Sep. 24, 2015

(30) Foreign Application Priority Data

Oct. 12, 2012 (EP) .................................. 12007076

(51) Int. Cl.
| | | |
|---|---|---|
| H01L 51/00 | (2006.01) | |
| C09K 11/06 | (2006.01) | |
| H05B 33/10 | (2006.01) | |
| H01L 51/50 | (2006.01) | |
| A61N 5/06 | (2006.01) | |
| C08F 212/32 | (2006.01) | |

(52) U.S. Cl.
CPC ........ *H01L 51/0035* (2013.01); *A61N 5/0616* (2013.01); *C08F 212/32* (2013.01); *C09K 11/06* (2013.01); *H01L 51/005* (2013.01); *H01L 51/0043* (2013.01); *H01L 51/0052* (2013.01); *H01L 51/0055* (2013.01); *H01L 51/0056* (2013.01); *H01L 51/0065* (2013.01); *H01L 51/0067* (2013.01); *H01L 51/0068* (2013.01); *H01L 51/5012* (2013.01); *H05B 33/10* (2013.01); *A61N 2005/0653* (2013.01); *A61N 2005/0661* (2013.01); *C09K 2211/1007* (2013.01); *C09K 2211/1029* (2013.01); *C09K 2211/1092* (2013.01); *C09K 2211/1408* (2013.01); *C09K 2211/1416* (2013.01); *H01L 51/5004* (2013.01); *H01L 51/5096* (2013.01); *H01L 2251/5384* (2013.01); *H01L 2251/552* (2013.01)

(58) Field of Classification Search
CPC .................................................. H01L 51/0035
USPC ..................................................... 428/690
See application file for complete search history.

(56) References Cited

U.S. PATENT DOCUMENTS

| | | | |
|---|---|---|---|
| 4,539,507 A | 9/1985 | VanSlyke et al. | |
| 5,151,629 A | 9/1992 | VanSlyke | |
| 5,273,680 A | 12/1993 | Gray et al. | |
| 5,324,449 A | 6/1994 | Kurmeier et al. | |
| 5,487,845 A | 1/1996 | Reiffenrath et al. | |
| 5,648,021 A | 7/1997 | Wingen et al. | |
| 5,840,217 A | 11/1998 | Lupo et al. | |
| 6,217,953 B1 | 4/2001 | Heckmeier et al. | |
| 6,458,909 B1 | 10/2002 | Spreitzer et al. | |
| 7,088,757 B1 | 8/2006 | Yu et al. | |
| 7,297,379 B2 * | 11/2007 | Schmidt ................... | C07C 25/22 252/299.62 |
| 7,345,301 B2 | 3/2008 | Gerhard et al. | |
| 7,807,068 B2 | 10/2010 | Bremer et al. | |
| 7,955,720 B2 | 6/2011 | Ye et al. | |
| 2002/0106531 A1 | 8/2002 | Naito | |
| 2003/0189216 A1 | 10/2003 | Kamatani et al. | |
| 2005/0255258 A1 | 11/2005 | Schmidt et al. | |
| 2006/0255332 A1 * | 11/2006 | Becker ................... | C09K 11/06 257/40 |
| 2010/0179469 A1 * | 7/2010 | Hammond ........... | A61N 5/0603 604/20 |
| 2012/0069289 A1 | 3/2012 | Taugerbeck et al. | |
| 2012/0197179 A1 | 8/2012 | Khan et al. | |
| 2014/0091295 A1 | 4/2014 | Becker et al. | |

FOREIGN PATENT DOCUMENTS

| | | |
|---|---|---|
| DE | 19927627 A1 | 1/2000 |
| DE | 19549741 B4 | 12/2004 |
| DE | 102004023914 A1 | 12/2005 |
| EP | 329752 A1 | 8/1989 |
| EP | 334911 A1 | 10/1989 |
| EP | 440082 A2 | 8/1991 |
| EP | 0441932 A1 | 8/1991 |
| EP | 676461 A2 | 10/1995 |
| EP | 1053578 A1 | 11/2000 |

(Continued)

OTHER PUBLICATIONS

Adamovich, V., et al., "New charge-carrier blocking materials for high efficiency OLEDs", Organic Electronics, 2003, vol. 4, pp. 77-87.
Chao, T.-C., et al., "Highly Efficient UV Organic Light-Emitting Devices Based on Bi(9,9-diarylfluorene)s", Advanced Materials, Advanced Materials, 2005, vol. 17, No. 8, pp. 992-996.
Chinese Office Action for Chinese application No. 201380053137.7, dated Mar. 8, 2017.
Korean Office Action for Korean application No. 10-2015-7012343, dated Apr. 19, 2017.
Ikai, M., et al., "Highly efficient phosphorescence from organic light-emitting devices with an exciton-block layer", Applied Physics Letters, 2001, vol. 79, No. 2, pp. 156-158.
Patel, D., et al., "Conjugated Polymers for Pure UV Light Emission: Poly(meta-phenylenes)", Polymer Physics, 2011, vol. 49, pp. 557-565.

(Continued)

*Primary Examiner* — Doris L Lee
(74) *Attorney, Agent, or Firm* — Drinker Biddle & Reath LLP

(57) ABSTRACT

The invention concerns polymers, electroluminescence devices, compositions and their use.

21 Claims, 11 Drawing Sheets

(56) References Cited

FOREIGN PATENT DOCUMENTS

| | | |
|---|---|---|
| EP | 1160888 A1 | 12/2001 |
| EP | 1220341 A2 | 7/2002 |
| EP | 1223209 A1 | 7/2002 |
| EP | 1223210 A1 | 7/2002 |
| EP | 2033707 A1 | 3/2009 |
| JP | H03162484 A | 7/1991 |
| JP | H06264059 A | 9/1994 |
| JP | H09202878 A | 8/1997 |
| JP | H10081874 A | 3/1998 |
| JP | 2003313547 A | 11/2003 |
| JP | 2005054078 A | 3/2005 |
| JP | 2005054079 A | 3/2005 |
| JP | 2006257168 A | 9/2006 |
| JP | 2011508055 A | 3/2011 |
| JP | 2011176250 A | 9/2011 |
| KR | 20020055425 A | 7/2002 |
| WO | WO-98/27136 A1 | 6/1998 |
| WO | WO 2004/041901 * | 5/2004 |
| WO | WO-2004/041901 A1 | 5/2004 |
| WO | WO-2004093207 A2 | 10/2004 |
| WO | WO-2004/113412 A2 | 12/2004 |
| WO | WO-2005003253 A2 | 1/2005 |
| WO | WO-2006/043087 A1 | 4/2006 |
| WO | WO-2010/133278 A1 | 11/2010 |
| WO | WO-2011/015265 A2 | 2/2011 |
| WO | WO-2011110277 A1 | 9/2011 |

OTHER PUBLICATIONS

Ran, X-Q, et al., "Theoretical studies on the electronic and optical properties of arene-versus fluroarene-thiophene co-oligomer", Journal of Physical Organic Chemistry, 2009, vol. 22, pp. 680-690.

International Search Report for PCT/EP2013/002806 dated May 14, 2014.

Office Action (English translation) for corresponding Chinese Patent Application No. 201380053137.7 dated Jun. 29, 2016.

Burrows, P.E., et al., "Ultraviolet electroluminescence and blue-green phosphorescence using an organic diphosphine oxide charge transporting layer", Applied Physics Letters, 2006, vol. 88, pp. 183503-3.

Japanese Office Action for Japanese Application No. 2015-536007, dated Aug. 22, 2017.

English Translation of Korean Office Action for Korean Application No. 2015-7012343, dated Nov. 22, 2017.

Otsuka, K., et al., "A Light-emitting Liquid Crystal Containing r-Terphenyl and an Alkylsiyl Group", Chem. Lett., 2012, vol. 41, pp. 307-309.

* cited by examiner

EMITTER AND HOSTS WITH AROMATIC UNITS

CROSS-REFERENCE TO RELATED APPLICATIONS

This application is a national stage application (under 35 U.S.C. § 371) of PCT/EP2013/002806, filed Sep. 18, 2013, which claims benefit of European Application No. 12007076.8, filed Oct. 12, 2012, both of which are incorporated herein by reference in their entirety.

The present invention relates to organic electroluminescent devices comprising aromatic, non-condensed emitter materials and to the use thereof.

The structure of organic light-emitting diodes (OLEDs), an organic electroluminescent devices in which organic semiconductors are employed as functional materials, is described, for example, in U.S. Pat. No. 4,539,507, U.S. Pat. No. 5,151,629, EP 0676461 and WO 98/27136. The emitting materials employed here, besides fluorescent emitters, are increasingly organometallic complexes which exhibit phosphorescence (M. A. Baldo et al., Appl. Phys. Lett. 1999, 75, 4-6). OLEDs represent a very highly promising technology for display screen and lighting applications. To this end, OLEDs are necessary which emit light in the visible region of the spectrum, i.e. typically red, green and blue light.

Furthermore, there are many applications which require light or radiation having even shorter wavelengths. Thus, for example, in the area of life science and medicine, 280 to 400 nm are necessary for cell imaging or for biosensors. Furthermore, in the electronics industry, 300 to 400 nm are required for solid-state lighting and 300 to 365 nm, for example, for the curing of polymers and printing ink. Also of major importance are phototherapeutic applications in the medical or cosmetics sector. Many undesired skin changes and skin diseases can be treated by means of phototherapy. Wavelengths in the region of ultraviolet (UV) radiation are often required for this purpose. An example thereof is the treatment of the skin of psoriatic patients, for which purpose a radiation source which emits UV radiation of a wavelength of 311 nm is typically employed.

Mercury, deuterium, excimer and xenon lamps are typical, conventional UV radiation sources. However, they are unwieldy and some contain toxic substances which may cause soiling and may represent health risks. The conventional lamps therefore have disadvantages regarding safety, usability, handling ability and portability, which in turn results in limited possible applications. In addition, UV-LEDs are also commercially available. However, most of these LEDs are either at the research stage, only emit radiation having a wavelength greater than 365 nm or are very expensive. In addition, LEDs have the disadvantage that they are point emitters, which require relatively thick and rigid devices. Another class of radiation sources or light sources are the organic electroluminescent devices (for example OLEDs or OLECs—organic light-emitting electrochemical cells). In contrast to the other light and radiation sources, these are area emitters. Furthermore, the organic electroluminescent devices allow the production of flexible equipment, such as displays, lighting devices and irradiation devices. These devices are also particularly suitable for many applications owing to their efficiency and the simple and space-saving structure.

However, only very little is known to date about organic electroluminescent devices which emit radiation in the UV region. The emission of most organic electroluminescent devices is usually limited to wavelengths greater than 350 nm. In addition, the performance data of these devices are very poor.

Chao et al. report (Adv. Mater. 17[8], 992-996. 2005.) on UV OLEDs based on fluorene polymers having an electroluminescence emission wavelength greater than 360 nm;

Wong et al. report (Org. Lett. 7[23], 5131-5134. 2005) on UV OLEDs based on spirobifluorene polymers having an electroluminescence emission wavelength at 360 nm or greater;

Zhou et al. report (Macromolecules 2007, 40 (9), 3015-3020) on UV OLEDs comprising emitting polymers based on fluorene and tetraphenylsilane derivatives having an electroluminescence emission wavelength at 350 nm;

Shinar et al. report (Applied Surface Science 2007, 254 (3), 749-756) on UV OLEDs using Bu-PBD as emitter having an electroluminescence emission wavelength of 350 nm.

Burrows reports (Applied Physics Letters 2006, 88 (18), 183503) on an OLED comprising 4,4'-bis(diphenylphosphine oxide) biphenyl as emitter. The device emits at 337 nm.

Sharma et al., reports (Applied Physics Letters 2006, 88 (14), 143511-143513) on a UV OLED which emits at 357 nm. The emitter used is based on polysilane.

There is therefore a very great need to develop organic electroluminescent devices which emit radiation in the UV region, in particular in the lower UV-A region (315 to 380 nm) and in the UV-B region (280 to 315 nm). A particular challenge here is the provision of suitable organic emitter materials and the provision of organic electroluminescent devices comprising these emitters.

SUMMARY OF THE INVENTION

The object of the present invention is therefore to overcome the said disadvantages of the prior art by the provision of organic electroluminescent devices having the best-possible physical properties which exhibit an emission in the UV region.

Surprisingly, it has been found that certain compounds, described in greater detail below, achieve these objects and result in organic electroluminescent device having unexpectedly good properties. The present invention therefore relates to organic electroluminescent devices which comprise compounds of this type.

The present invention relates to an electroluminescent device, preferably an organic electroluminescent device, which emits radiation of a wavelength of less than or equal to 350 nm and preferably emits UV-B radiation, i.e. radiation having a wavelength in the range from 280 to 315 nm. The device comprises at least two electrodes and at least one emitting layer, where the emitting layer comprises at least one compound of the general formula (1) shown below.

The present invention therefore relates to an electroluminescent device comprising at least two electrodes and at least one emitting layer between the electrodes which comprises at least one compound of the general formula (1)

$$Ar^1\text{—}Ar^2\text{—}(Ar^3)_n \qquad \text{formula (1)}$$

where the device emits radiation having a wavelength in the range from 280 nm and 380 nm
and where the following applies to the symbols and indices used:

$Ar^1$, $Ar^2$ and $Ar^3$
are, identically or differently, five- or six-membered aromatic and/or heteroaromatic rings, which may in each case be substituted by one or more radicals $R^1$, which may be independent of one another;

n
  is 0 or 1;
$R^1$
  is, identically or differently on each occurrence, H, D, F, $N(R^2)_2$, CN, $Si(R^2)_3$, $B(OR^2)_2$, $P(R^2)_2$, $S(=O)R^2$, a straight-chain alkyl, alkoxy or thioalkoxy group having 1 to 40 C atoms or a branched or cyclic alkyl, alkoxy, alkylalkoxy or thioalkoxy group having 3 to 40 C atoms, each of which may be substituted by one or more radicals $R^2$, where one or more non-adjacent $CH_2$ groups, may be replaced by $Si(R^2)_2$, $Ge(R^2)_2$, $Sn(R^2)_2$, C=O, C=S, C=Se, $C=NR^2$, SO, $SO_2$, $NR^2$, O, S or $CONR^2$, which is not bonded directly to ring of the formula (I), by $R^2C=CR^2$, C≡C or $P(=O)(R^2)$ and where one or more H atoms may be replaced by D, F, Cl, or CN, or an aromatic or heteroaromatic ring having 5 to 18 aromatic ring atoms, which may in each case be substituted by one or more radicals $R^2$, or a combination of two or more of these groups, two or more substituents $R^1$ here may also form a non-aromatic ring system with one another;
$R^2$
  is, identically or differently on each occurrence, H, D, F, Cl, $N(R^3)_2$, CN, $Si(R^3)_3$, $B(OR^3)_2$, $C(=O)R^3$, $P(=O)(R^3)_2$, $S(=O)R^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals $R^3$, where one or more non-adjacent $CH_2$ groups may be replaced by $R^3C=CR^3$, C≡C, $Si(R^3)_2$, $Ge(R^3)_2$, $Sn(R^3)_2$, C=O, C=S, C=Se, $C=NR^3$, $P(=O)(R^3)$, SO, $SO_2$, $NR^3$, O, S or $CONR^3$ and where one or more H atoms may be replaced by D, F, Cl or CN, or an aromatic or heteroaromatic ring having 5 to 18 aromatic ring atoms, which may in each case be substituted by one or more radicals $R^3$, or a combination of two or more of these groups; two or more adjacent radicals $R^2$ here may form a non-aromatic ring system with one another;
$R^3$
  is, identically or differently on each occurrence, H, D, F or an aliphatic, aromatic and/or heteroaromatic hydrocarbon radical having 1 to 18 C atoms, in which, in addition, one or more H atoms may be replaced by F; two or more substituents $R^3$ here may also form a non-aromatic mono- or polycyclic, aliphatic ring system with one another.
with the proviso that the compound of the formula (1) contains no condensed aromatic or condensed heteroaromatic ring systems, and with the proviso that the compound of the formula (1) contains no conjugated moiety containing more than 18 conjugated π (pi) electrons.

A DETAILED DESCRIPTION OF THE INVENTION

Figure 1:
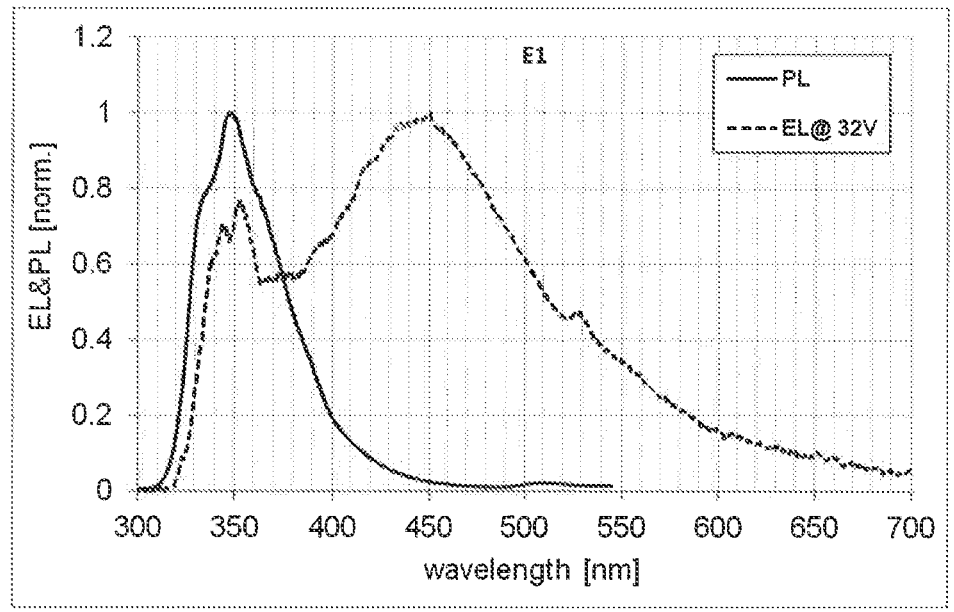
FIGS. 1 to 4 and 6 to 15 show the electroluminescence (EL) and corresponding photoluminescence (PL) of OLEDs 1 to 16.
Figure 2:
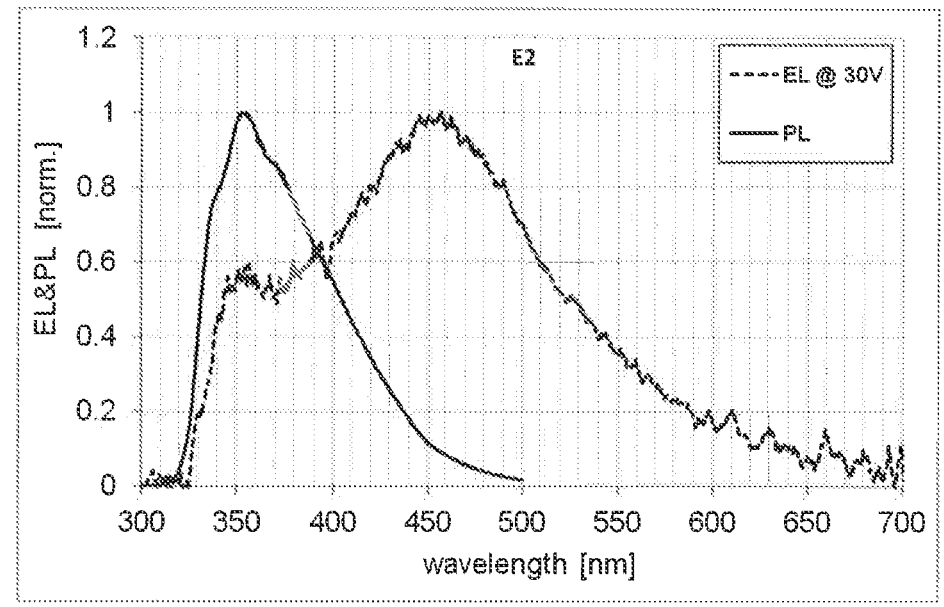
Figure 3:
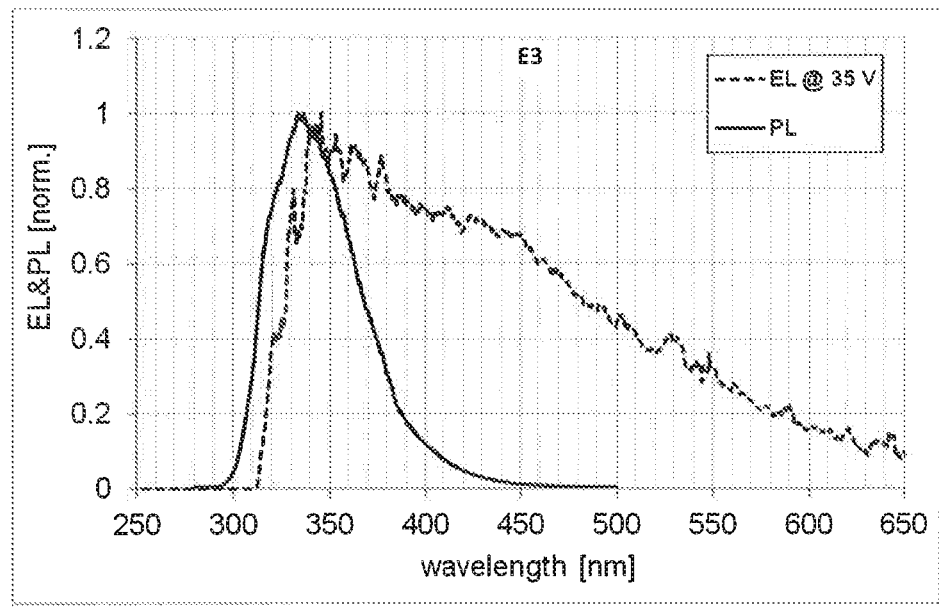
Figure 4:
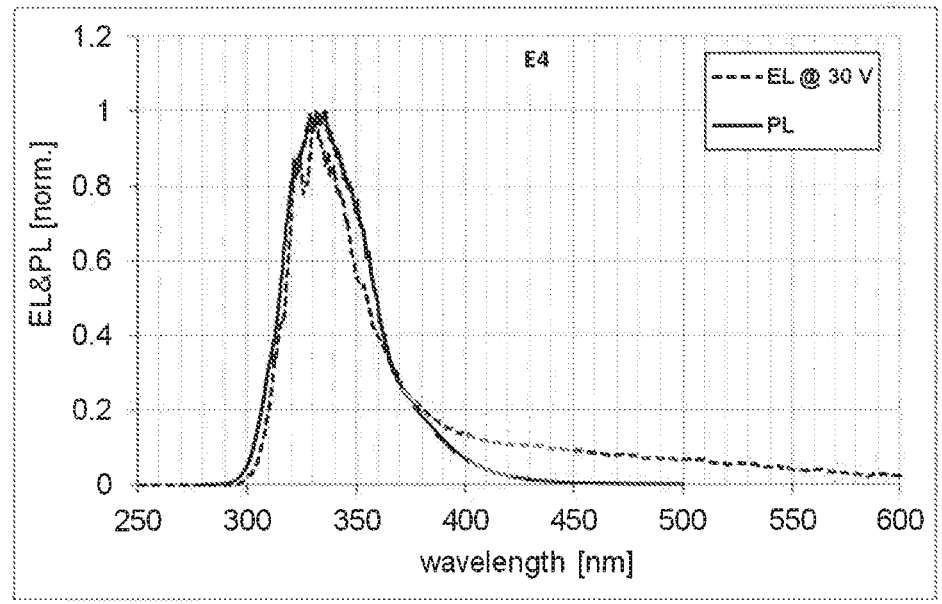
Figure 5:
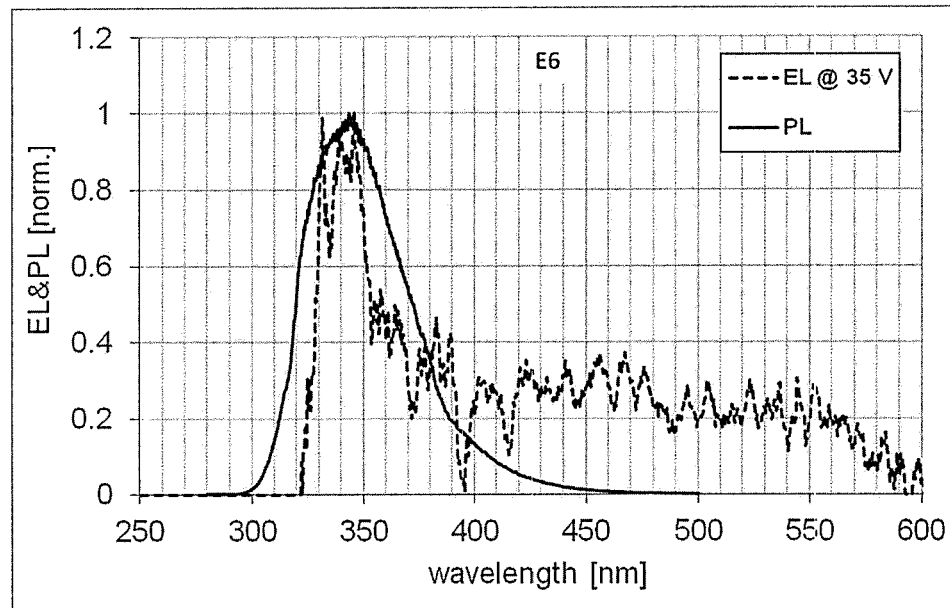
Figure 6:
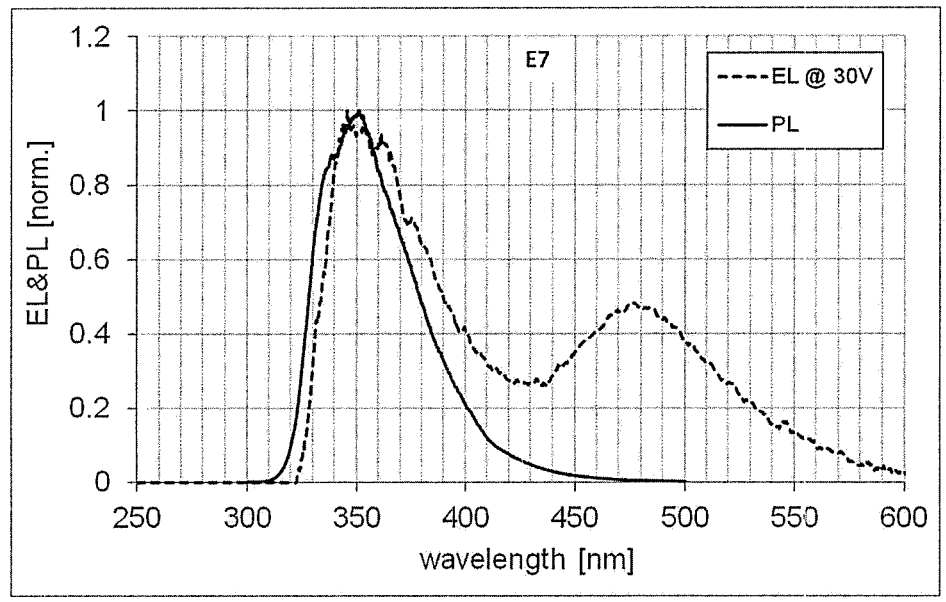
Figure 7:
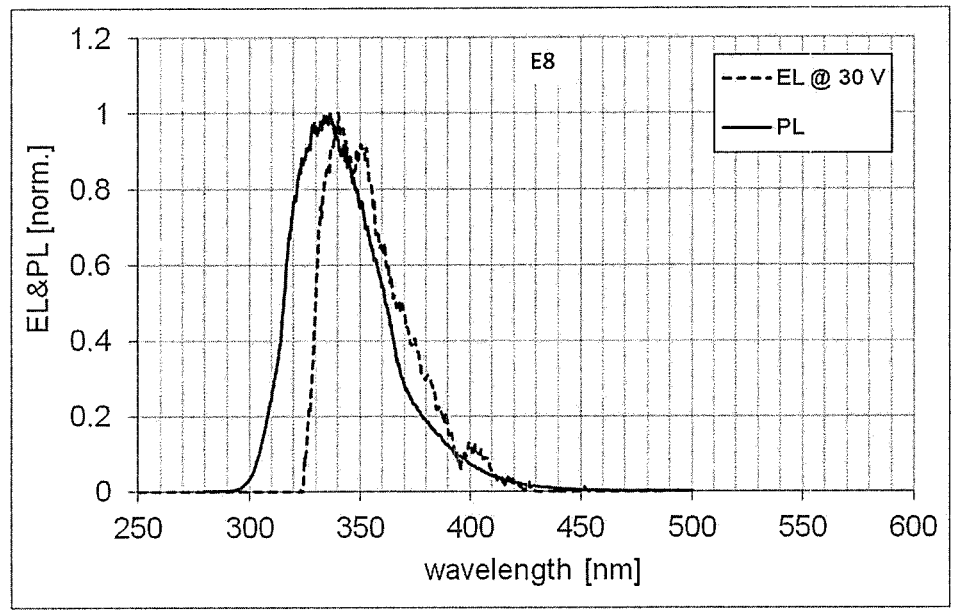
Figure 8:
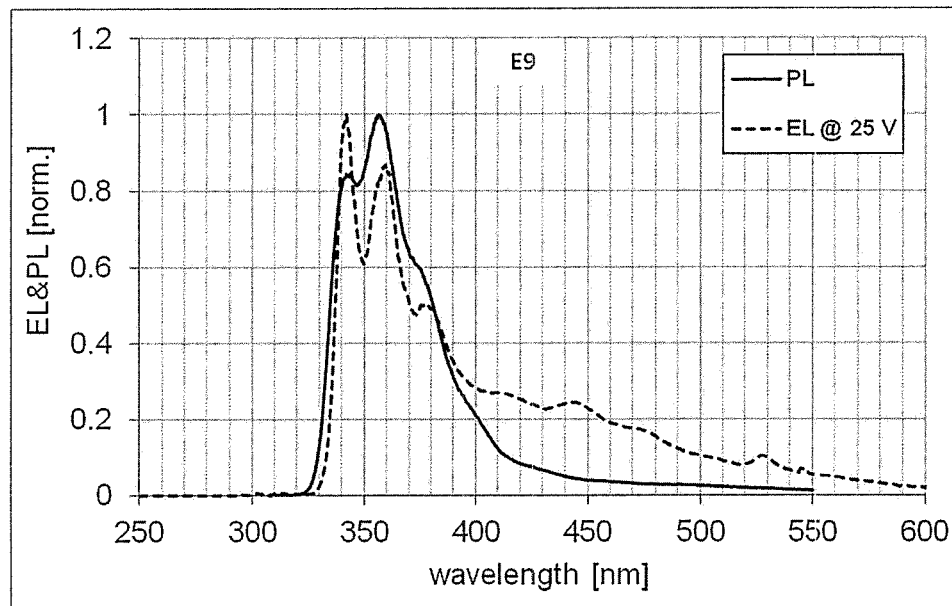
Figure 9:
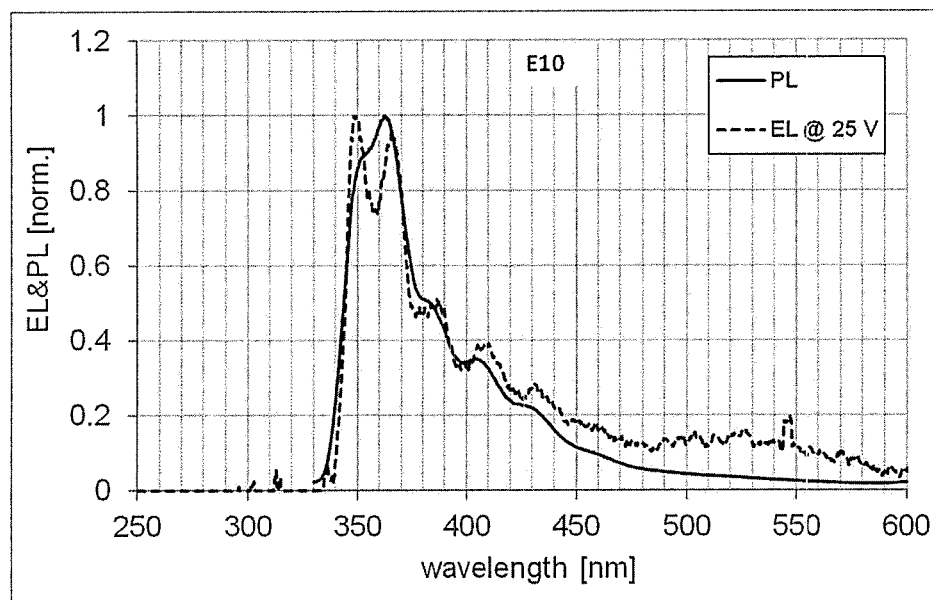
Figure 10:
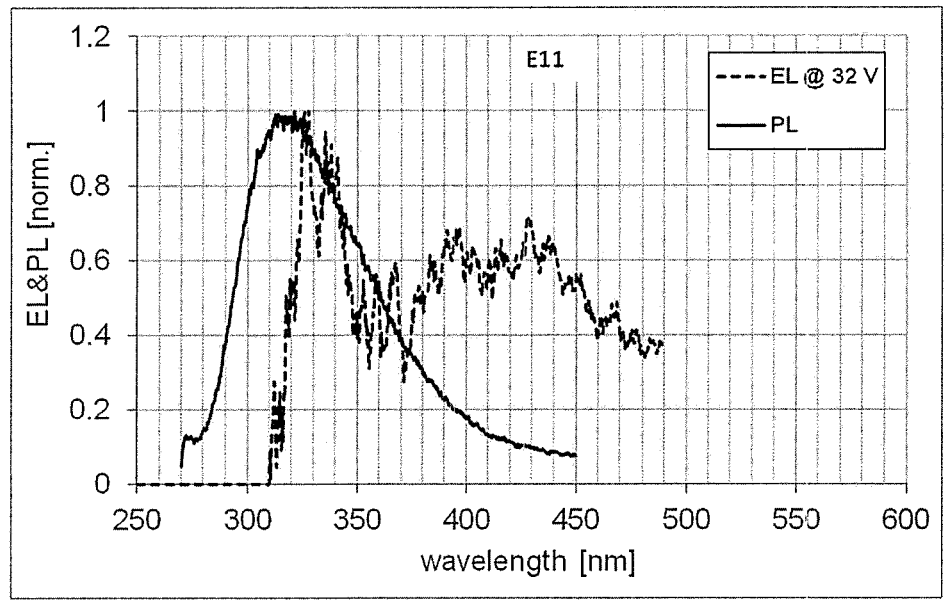
Figure 11:
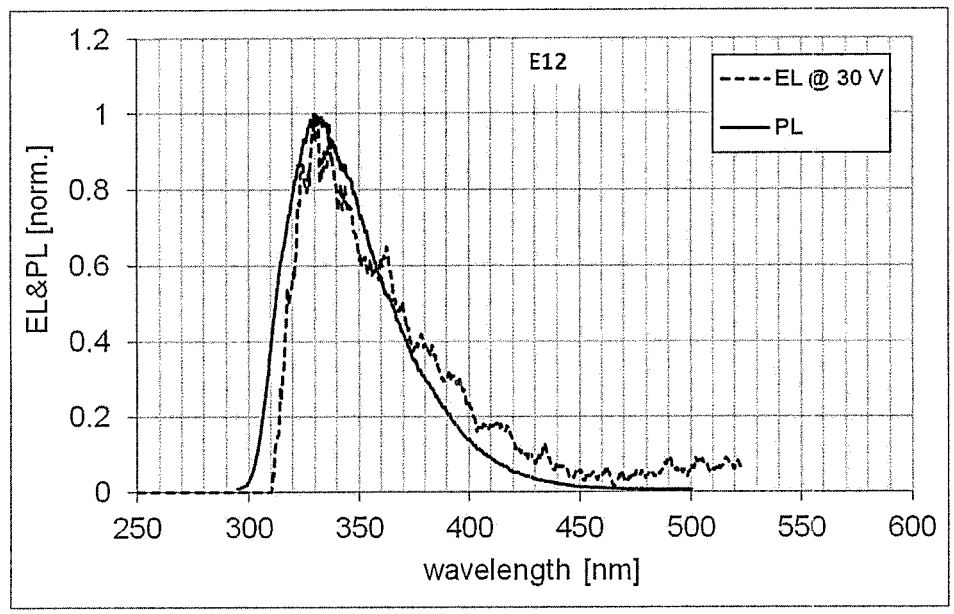
Figure 12:
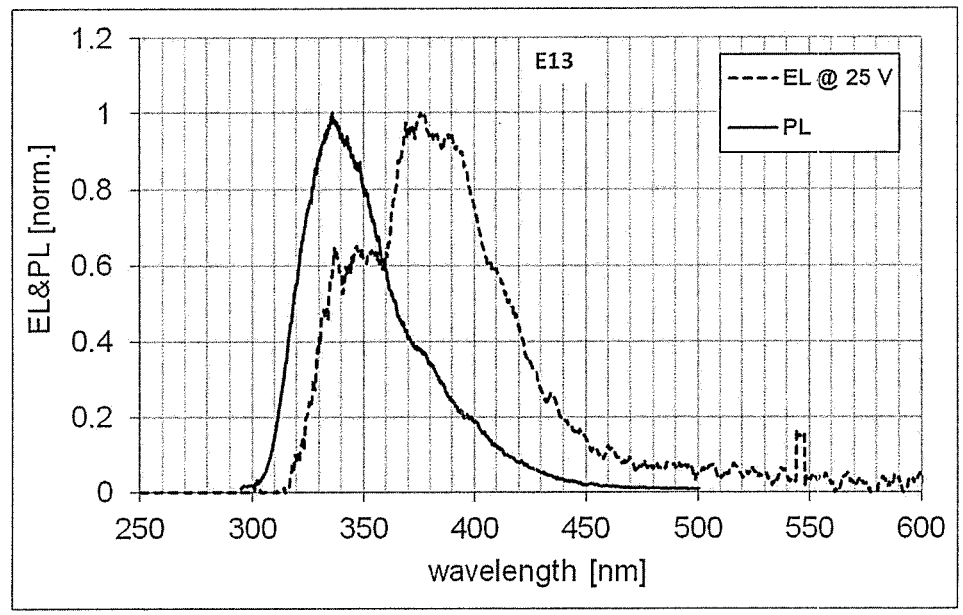
Figure 13:
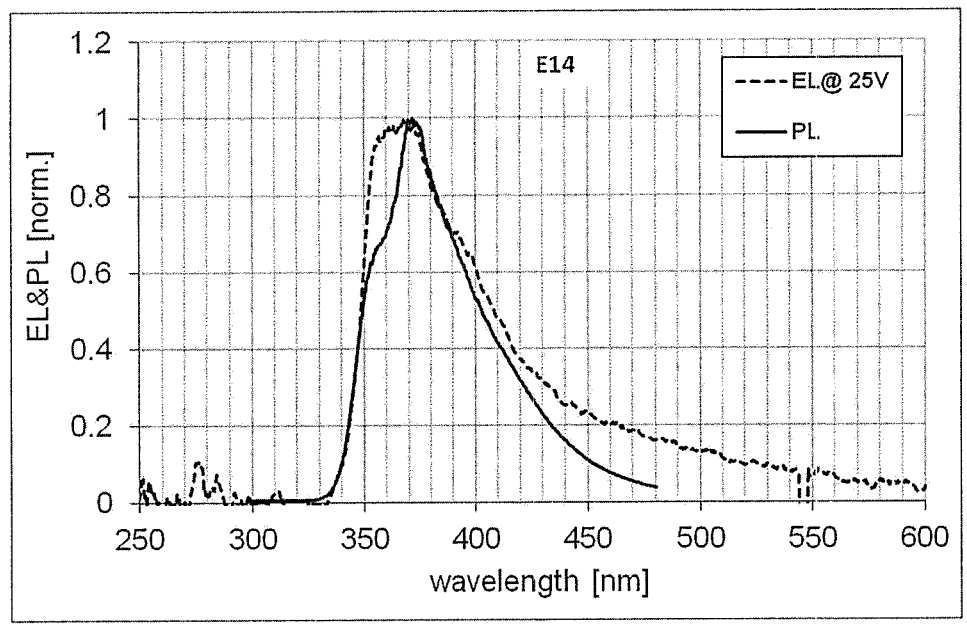
Figure 14:
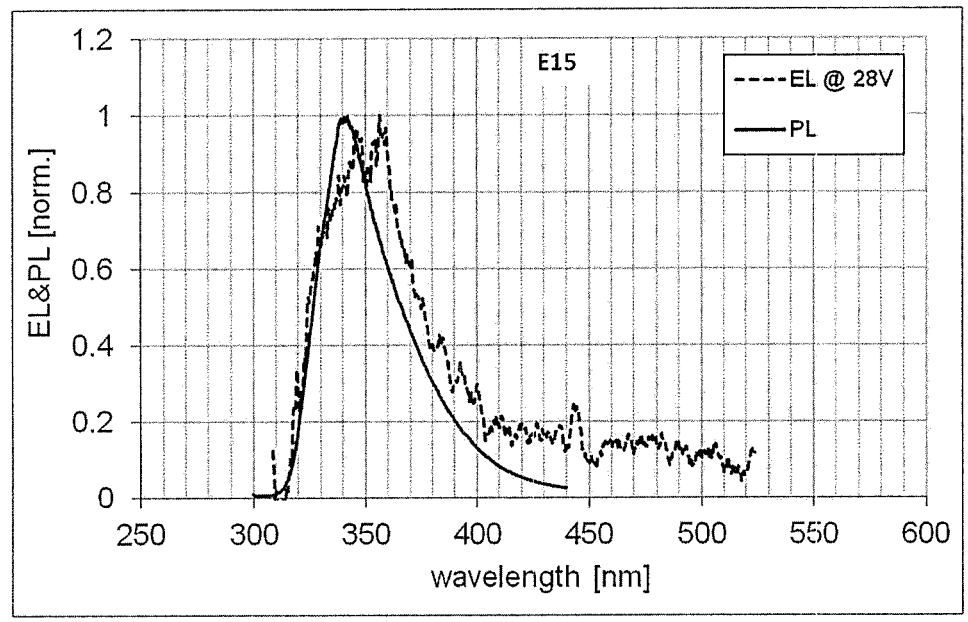
Figure 15:
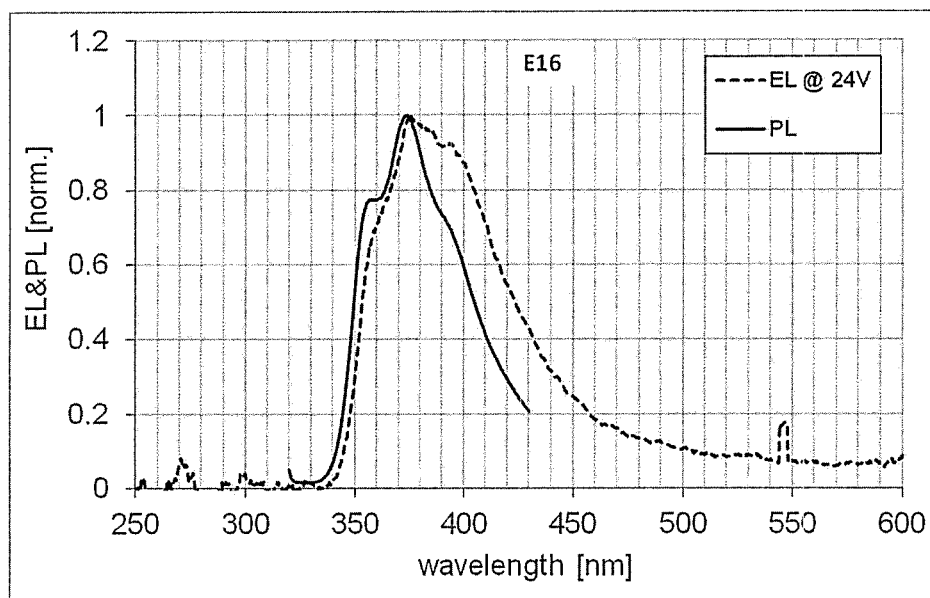
Figure 16:
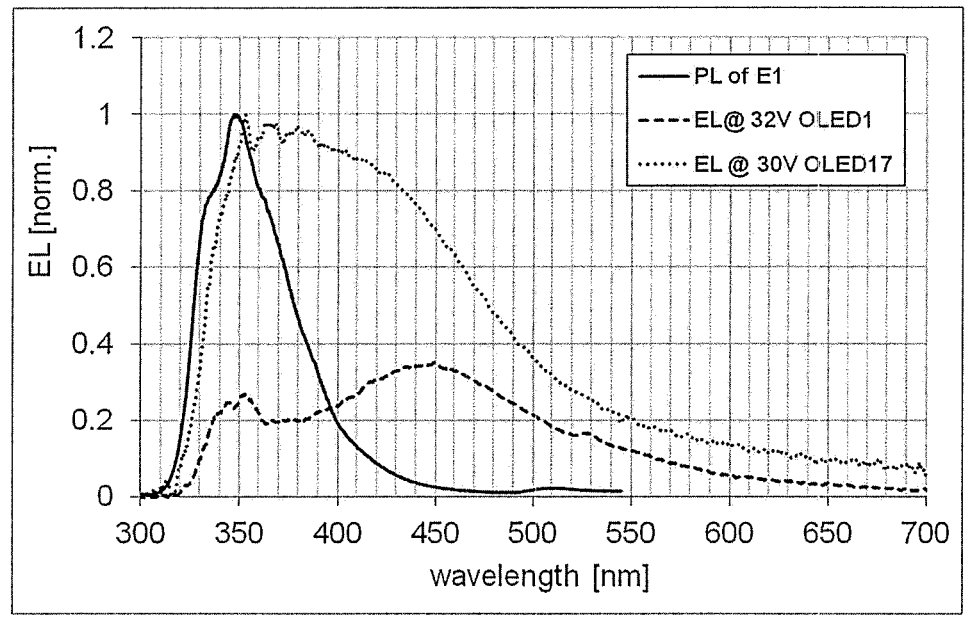
FIG. 16 shows the EL spectra and operating voltages of OELD1 and OLED17 in comparison.

The groups $Ar^1$, $Ar^2$ and $Ar^3$ are any desired aromatic and/or heteroaromatic rings having 5 or 6 ring atoms.

The groups $Ar^1$, $Ar^2$ and $Ar^3$ in the compound of the general formula (1) are preferably, identically or differently on each occurrence, a compound of the general formula (2), where the bonding between $Ar^1$ and $Ar^2$ and between $Ar^2$ and $Ar^3$ can take place at any desired site of the compound of the formula (2);

formula (2)

where the following applies to the symbols used:
X
  is on each occurrence, identically or differently, $CR^1$ or N;
Q
  is on each occurrence, identically or differently, X=X, $NR^1$, O, S, Se, preferably, X=X, $NR^1$ and S and very preferably X=X and $NR^1$.

Furthermore, the groups $Ar^1$, $Ar^2$ and $Ar^3$ in the compound of the formula (1) are preferably, identically or differently on each occurrence, one of the following groups, where the bonding between the groups can take place at any desired and chemically possible site, and where the groups may be substituted by one or more radicals $R^1$ which are independent of one another, where the radicals $R^1$ are defined as indicated above.

formula (3)

formula (4)

formula (5)

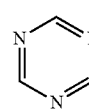

formula (6)

-continued

formula (7)

formula (8)

formula (9)

formula (10)

formula (11)

formula (12)

formula (13)

formula (14)

formula (15)

formula (16)

formula (17)

The electroluminescent device preferably comprises at least one compound of the formula (18a) or (18b) in the emitting layer

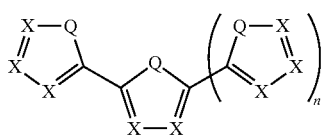
formula (18a)

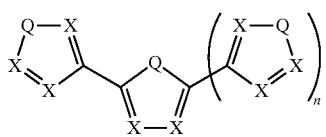
formula (18b)

where the above definitions apply to the symbols and the index.

The compounds of the general formula (1) are preferably fluorescent emitters, i.e. the compounds emit radiation from an electronically excited singlet state.

Furthermore, the compound of the formula (1) in the electroluminescent device preferably contains no condensed rings.

In a further preferred embodiment, the present invention relates to the said electroluminescent device comprising the compound of the general formula (1) in the emitting layer, where at least one non-aromatic bridge occurs between $Ar^1$, $Ar^2$ and $Ar^3$, preferably conforming to the following general formulae (19) to (26)

formula (19)

formula (20)

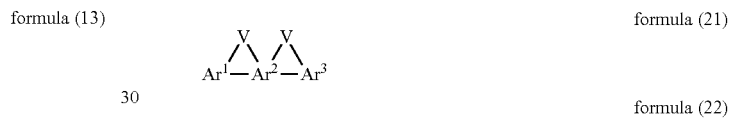
formula (21)

formula (22)

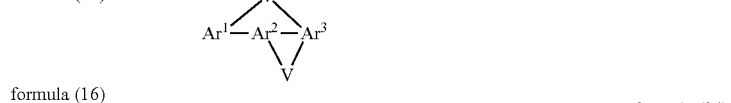
formula (23)

formula (24)

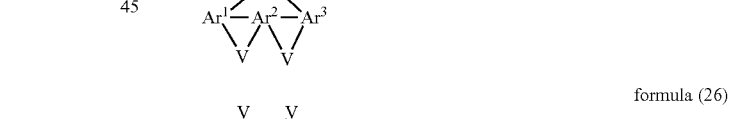
formula (25)

formula (26)

where the above definitions apply to $Ar^1$, $Ar^2$ and $Ar^3$ and where V is identical or different on each occurrence and stands for a non-aromatic bridge of the aromatic groups $Ar^1$ to $Ar^3$ and contains O, S, Se, N, Si, B, P and/or at least one $C(R^2)_2$ group.

Bridged structures have the advantage that the efficiency and stability of the devices according to the invention are increased further. With respect to the desired UV emission, however, it should be ensured that the conjugated pi systems, as indicated above, present in the compounds of the formula (1) is kept sufficiently small.

In a preferred embodiment, the non-aromatic bridging takes place through V, where V is equal to $C(R^2)_2$ or $Si(R^2)_2$.

Further very preferred embodiments for V are summarised in the following overview.

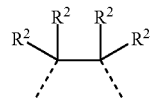

formula (27)

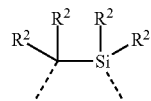

formula (28)

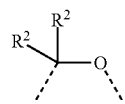

formula (29)

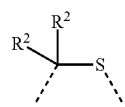

formula (30)

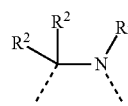

formula (31)

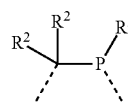

formula (32)

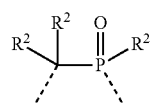

formula (33)

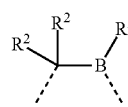

formula (34)

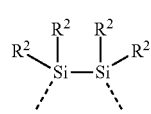

formula (35)

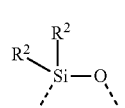

formula (36)

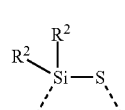

formula (37)

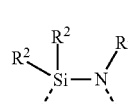

formula (38)

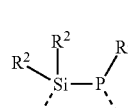

formula (39)

-continued

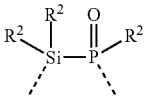

formula (40)

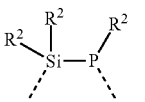

formula (41)

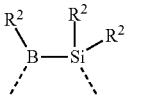

formula (42)

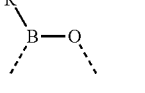

formula (43)

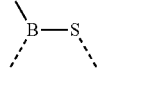

formula (44)

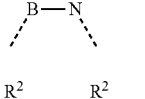

formula (45)

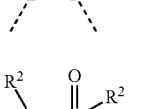

formula (46)

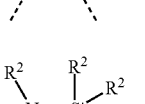

formula (47)

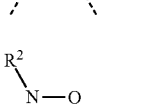

formula (48)

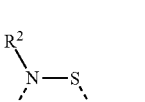

formula (49)

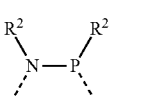

formula (50)

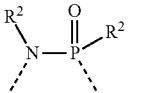

formula (51)

formula (52)

formula (53)

-continued

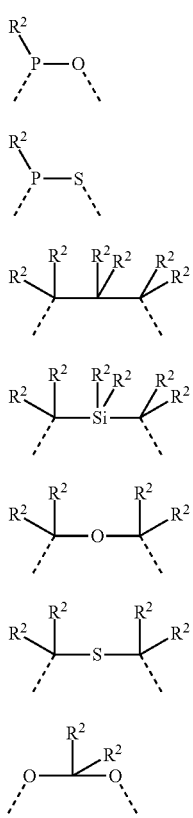

where the radicals R² are defined as indicated above and where the dashed lines denote the bonds to the groups Ar¹, Ar² or Ar³.

In a very preferred embodiment, the present invention relates to an electroluminescent device comprising the compound in the emitting layer selected from the compounds having the formulae (61) to (68)

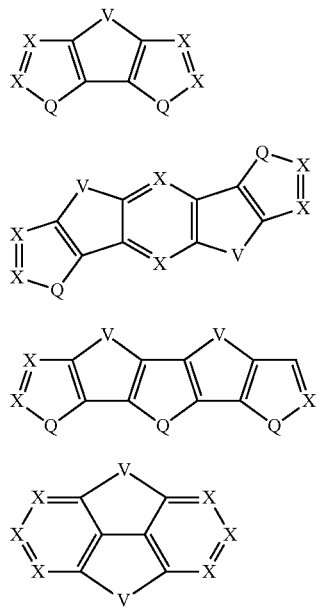

formula (54)
formula (55)
formula (56)
formula (57)
formula (58)
formula (59)
formula (60)

formula (61)
formula (62)
formula (63)
formula (64)

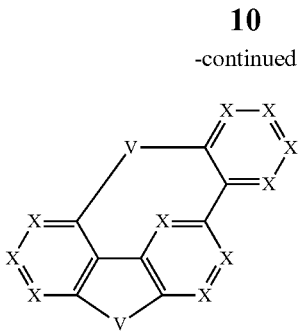

formula (65)

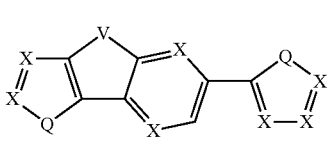

formula (66)

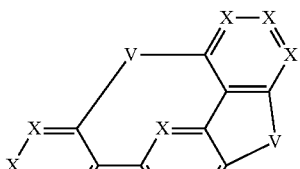

formula (67)

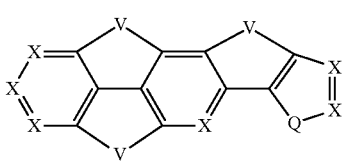

formula (68)

where X, Q and V are defined as indicated above.

It is very particularly preferred for Q to be equal to X=X.

It is furthermore very particularly preferred if X=CR¹.

It is especially preferred if Ar² in the compound of the formula (1) is selected from the formulae (69) to (86)

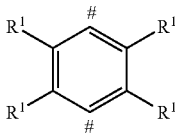

formula (69)

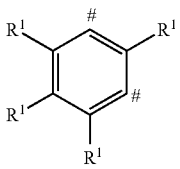

formula (70)

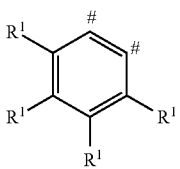

formula (71)

formula (72)
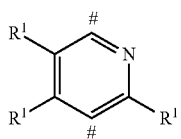

formula (73)
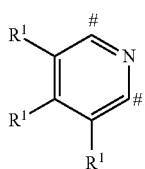

formula (74)
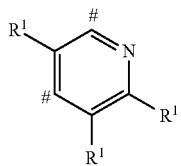

formula (75)
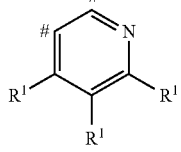

formula (76)
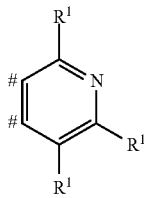

formula (77)
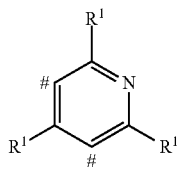

formula (78)
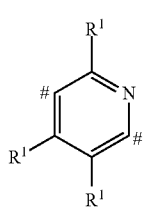

formula (79)
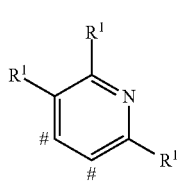

formula (80)
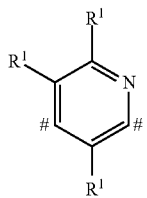

formula (81)
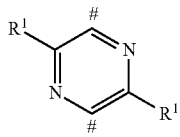

formula (82)
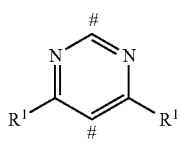

formula (83)
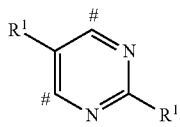

formula (84)
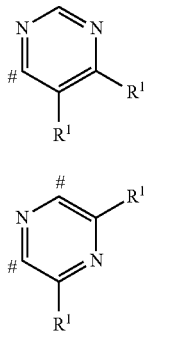

formula (85)
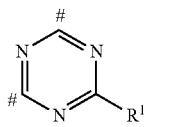

formula (86)
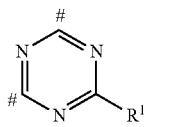

where # stands for the linking positions to $Ar^1$ and $Ar^3$ and where, in the case where n=0, one of the two C atoms denoted by # is substituted by the radical $R^1$.

It is even more preferred if $Ar^2$ in the compound of the formula (1) is equal to the formula (87)

formula (87)
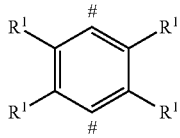

where the above comments apply to the positions denoted by #.

The groups $Ar^1$ and $Ar^3$, which may be identical to or different from one another, are furthermore preferably equal to a compound of the general formula (88)

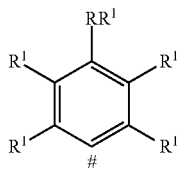

formula (88)

where $RR^1$ is either equal to $R^1$ or alternatively equal to H, F, Cl, a linear or branched or cyclic alkyl, alkoxy, alkylalkoxy or thioalkoxy group having 1 to 40 C atoms, where the groups may be unsubstituted or may be monosubstituted by $CF_3$, halogen, CN and where one or more $CH_2$ groups may be substituted by —O—, —S—, —$CF_2$O—, —O$CF_2$—, —OC—O— or —O—CO— in such a way that the O atoms are not connected directly to one another.

In a furthermore especially preferred embodiment, the compound in the emitting layer has one of the following general formulae (89-1) to (89-6)

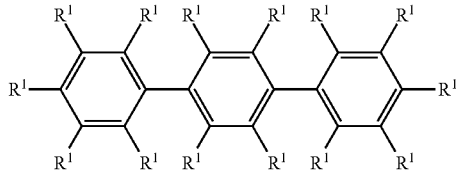

formula (89-1)

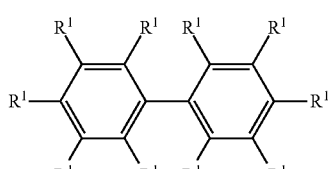

formula (89-2)

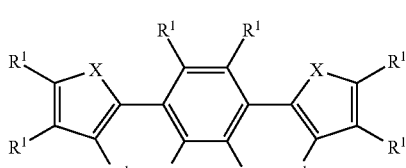

formula (89-3)

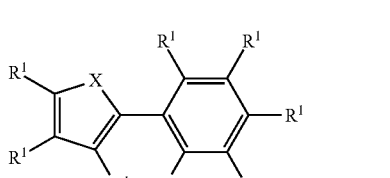

formula (89-4)

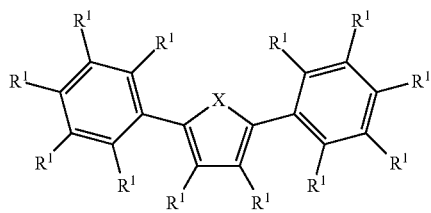

formula (89-5)

formula (89-6)

where preferably a maximum of 6 of the radicals $R^1$ are not equal to H and where the above definitions apply to the radicals $R^1$.

The emitters in the emission layer here are very particularly preferably the compounds of the general formulae (89-1) and/or (89-2).

In a furthermore preferred embodiment, $R^1$ is selected, identically or differently on each occurrence, from the group consisting of H, F, CN, $CF_3$, $CHF_2$ and an alkyl, alkoxy, alkylalkoxy group having 1 to 15 C atoms.

In a further preferred embodiment, more than one radical $R^1$ in the above-mentioned formulae which contain $R^1$ is equal to F, very preferably more than 2 of the radicals $R^1$ are equal to F and very particularly preferably more than 3 radicals $R^1$ are equal to F.

In a further preferred embodiment, the compound in the emitting layer is selected from the compound of the formula (89-1a)

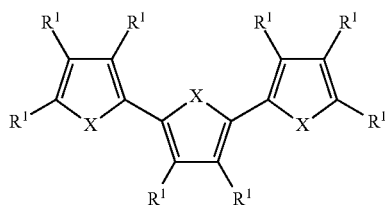

formula (89-1a)

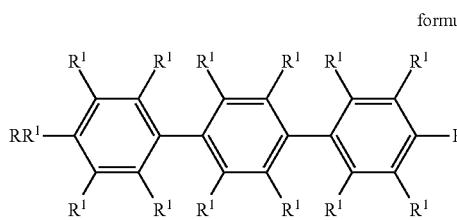

where preferably a maximum of 4 of the radicals $R^1$ are not equal to H and RR1 is defined as indicated above.

Examples of preferred compounds in accordance with the embodiments indicated above are the emitter compounds of the following structures.

formula (90)

formula (91)

formula (92)

formula (93)

formula (94)

formula (95)

formula (96)

formula (97)

formula (98)
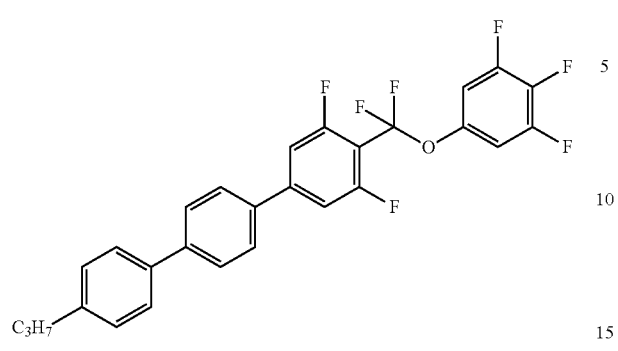
formula (99)
formula (100)
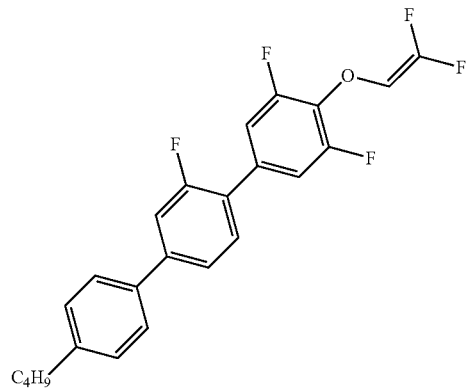
formula (101)
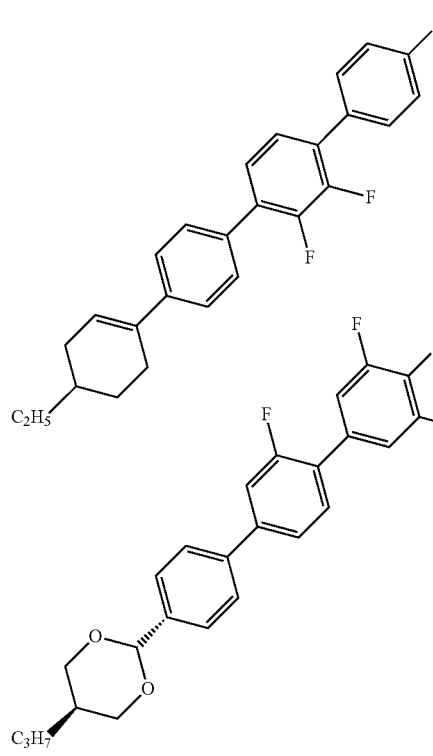
formula (102)
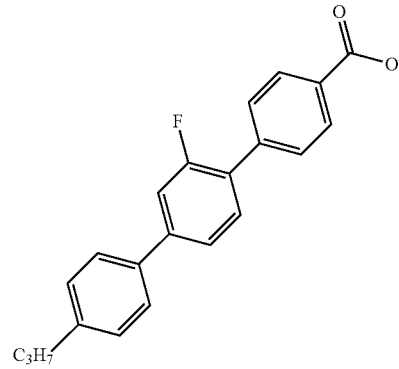
formula (102a)
formula (103)
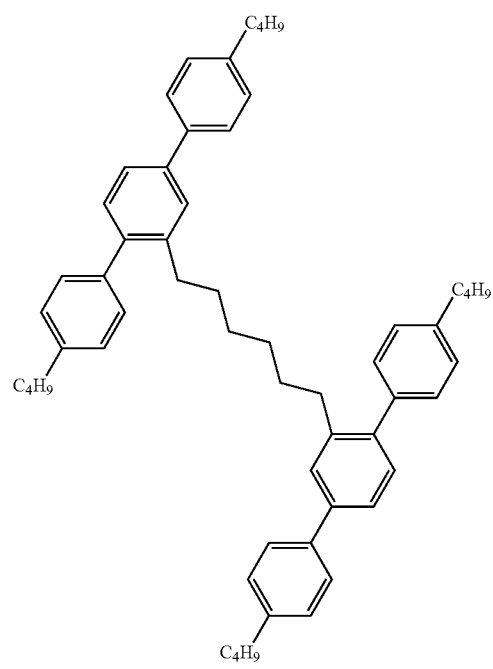

formula (104)
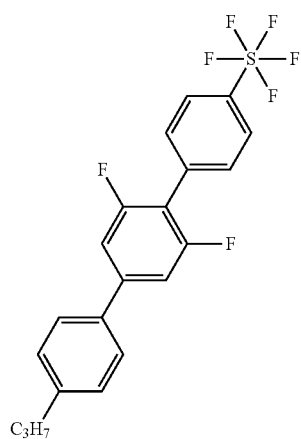
formula (105)
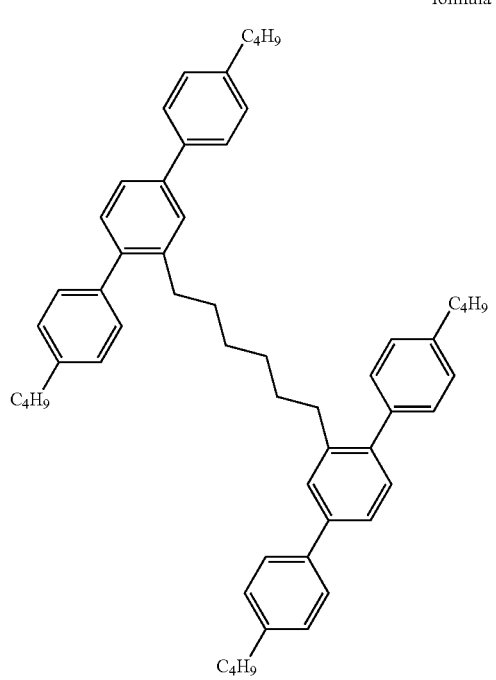
formula (106)
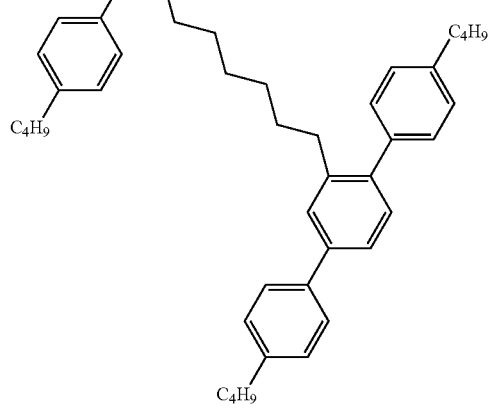
formula (107)
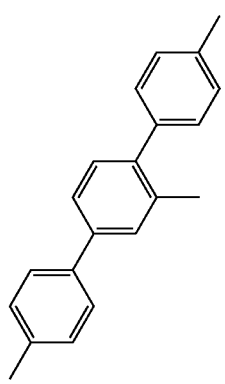
formula (108)
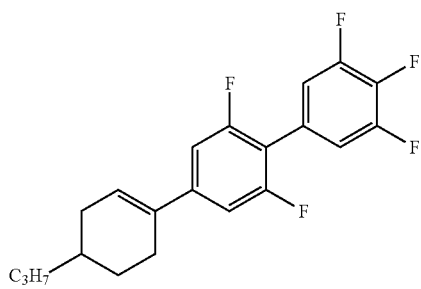
formula (109)
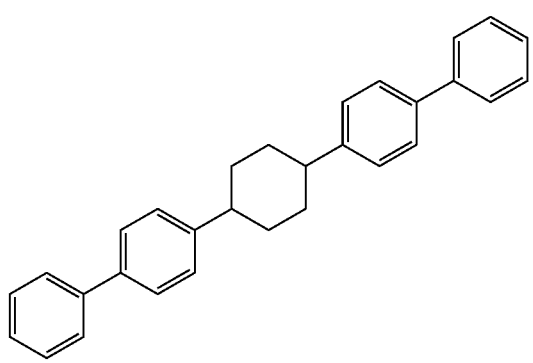
formula (110)
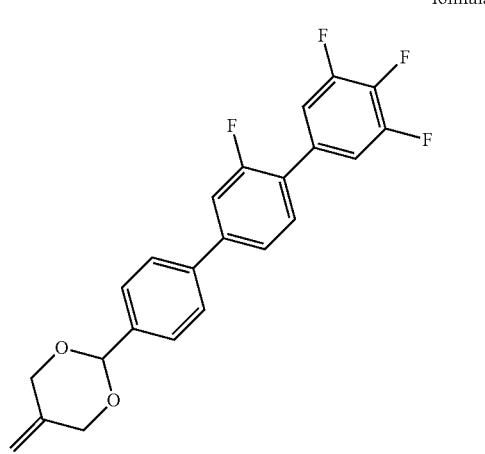
formula (111)
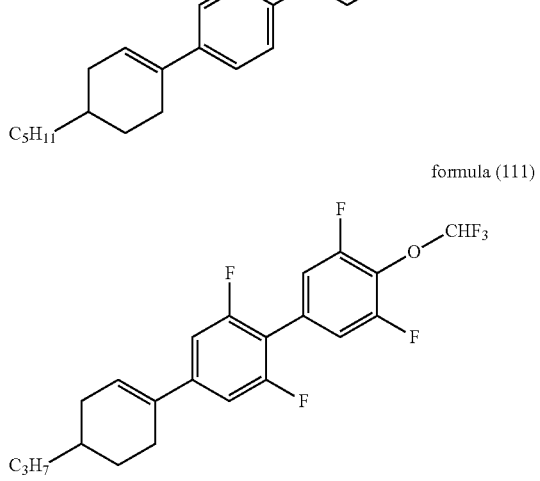

formula (112)
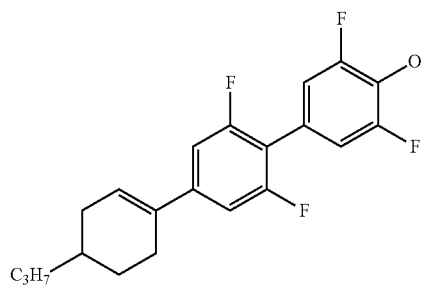
formula (113)
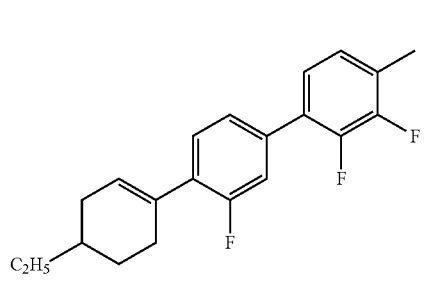
formula (114)
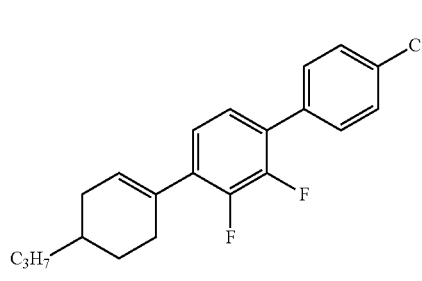
formula (115)
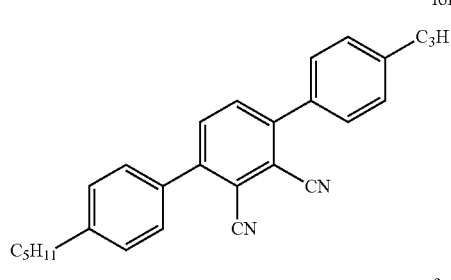
formula (116)
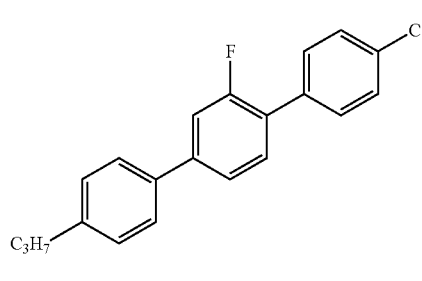
formula (117)
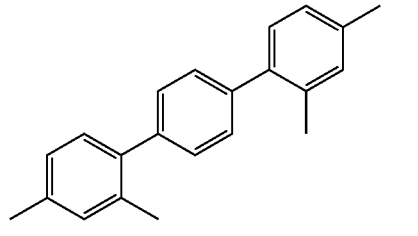
formula (118)
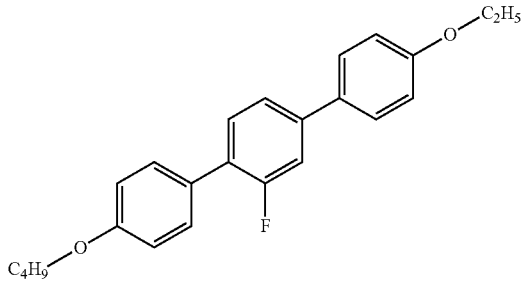
formula (119)
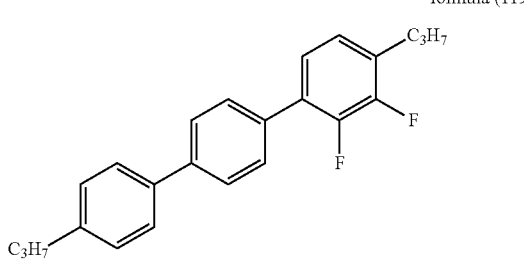
formula (120)
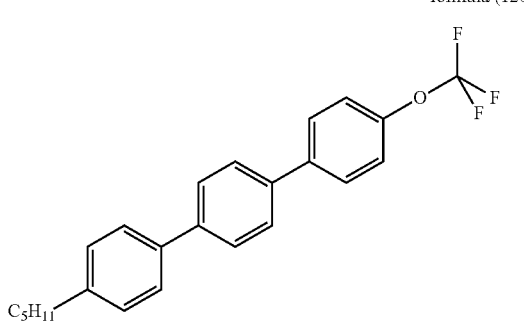
formula (121)
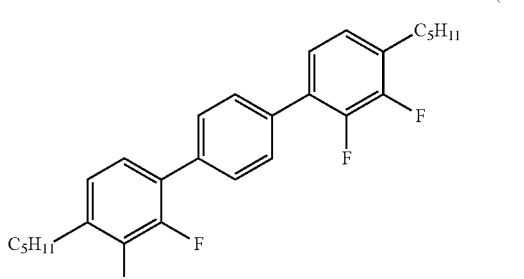
formula (122)
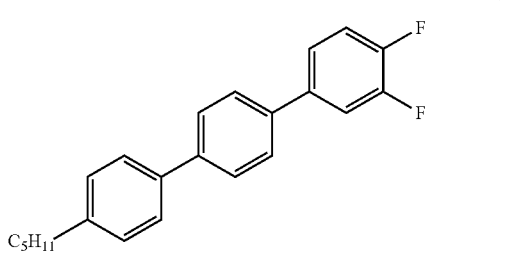

formula (123)
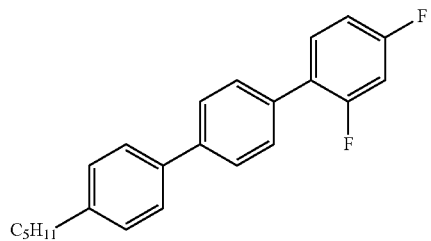
formula (124)
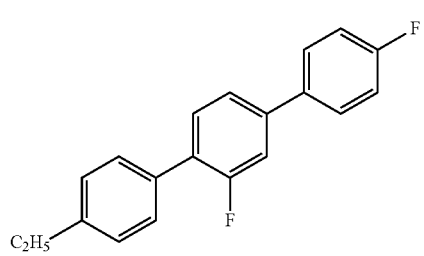
formula (125)
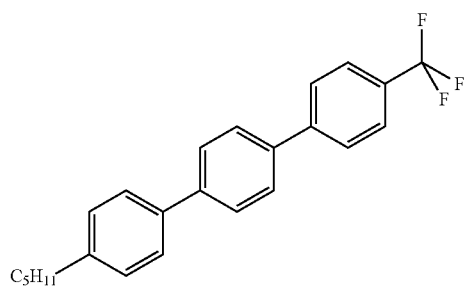
formula (126)
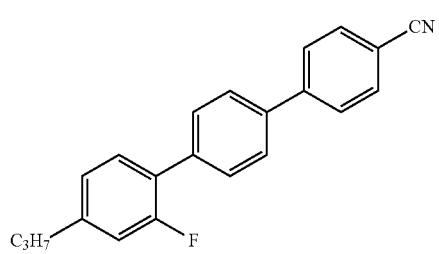
formula (127)
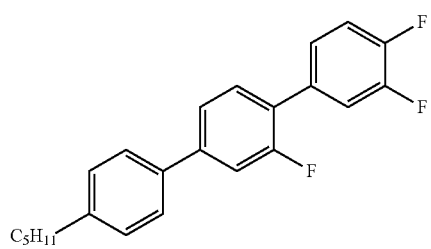
formula (128)
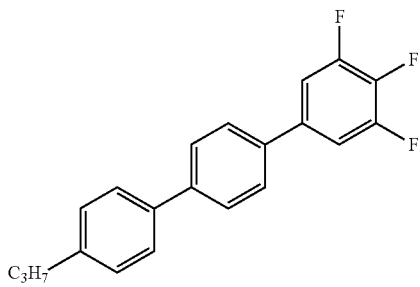
formula (129)
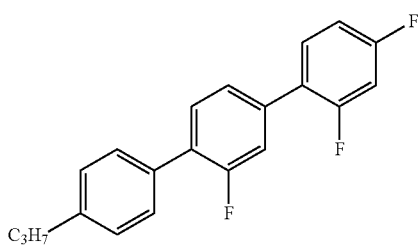
formula (130)
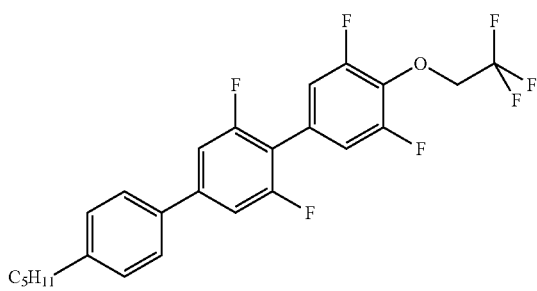
formula (131)
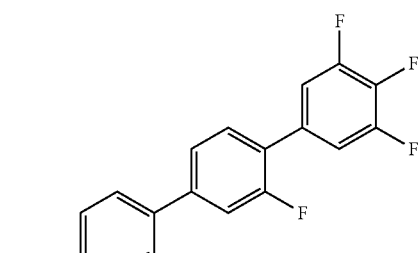
formula (132)
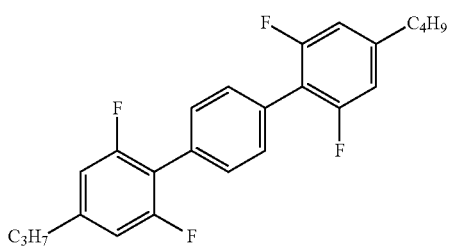

formula (133)
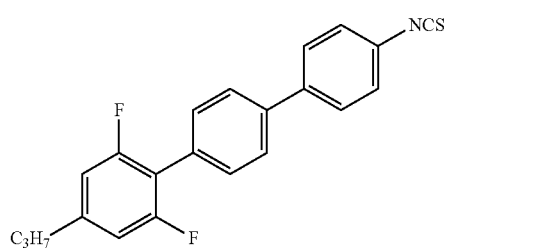
formula (134)
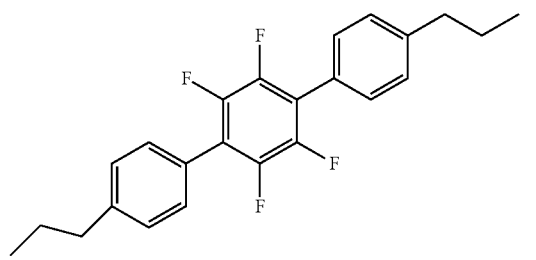
formula (135)
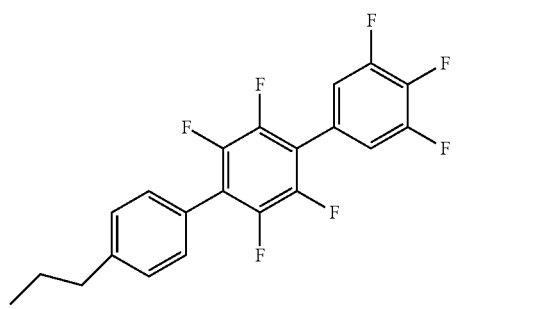
formula (136)
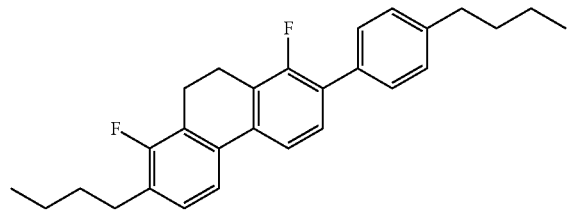
formula (137)
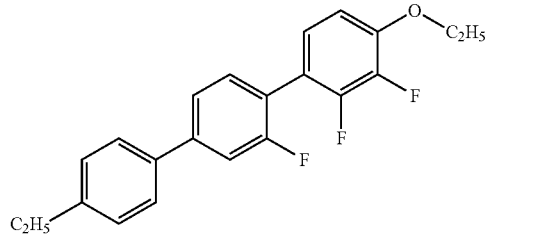
formula (138)
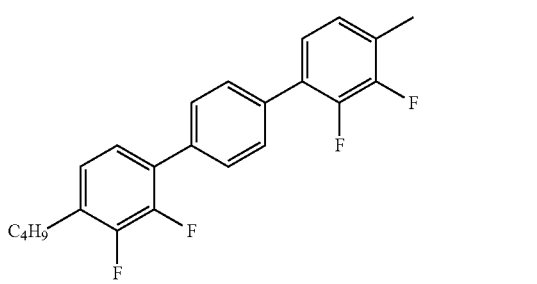
formula (139)
formula (140)
formula (141)
formula (142)

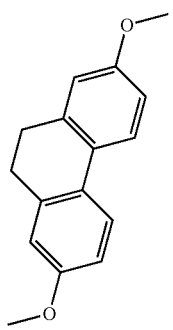
formula (143)
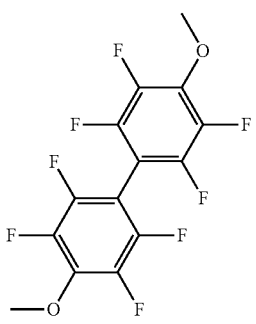
formula (144)
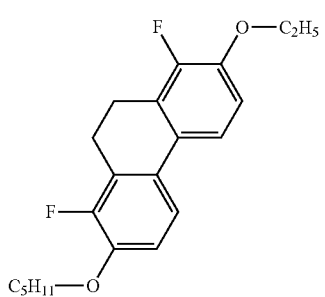
formula (147)
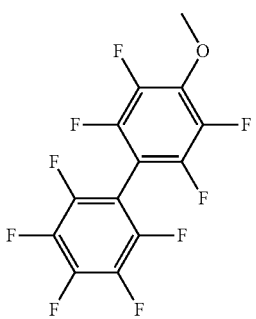
formula (148)
formula (145)
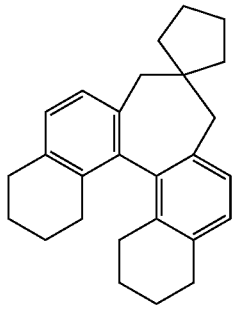
formula (149)
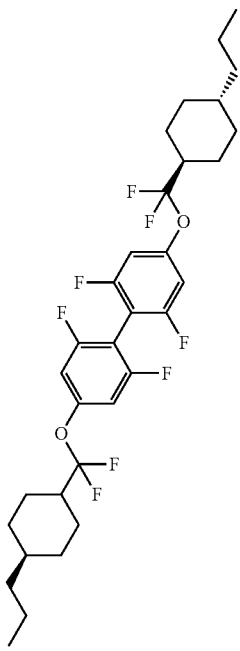
formula (146)
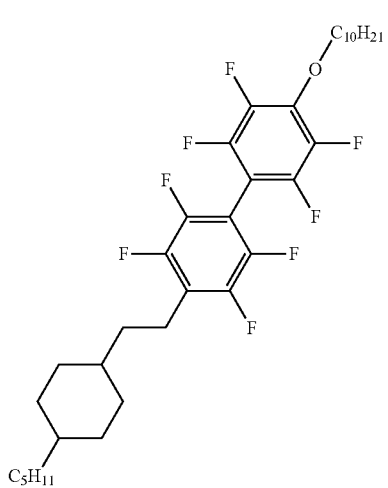
formula (150)
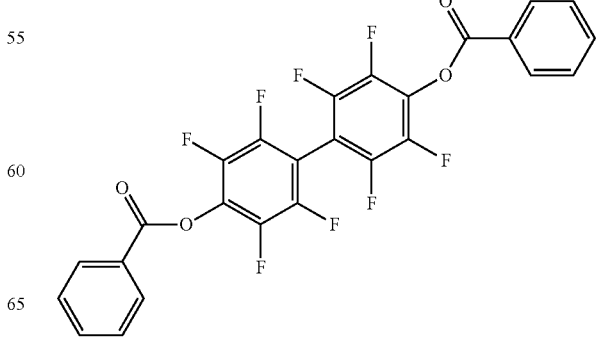

-continued
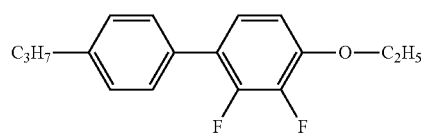
formula (151)
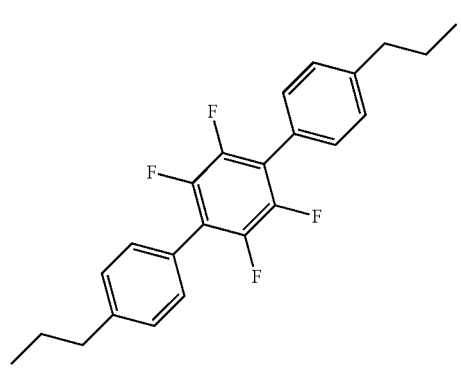
formula (152)
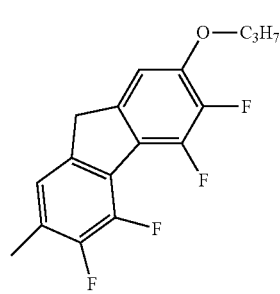
formula (153)
formula (154)
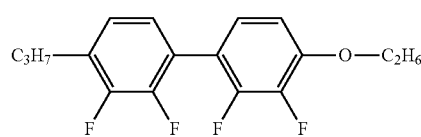
formula (155)
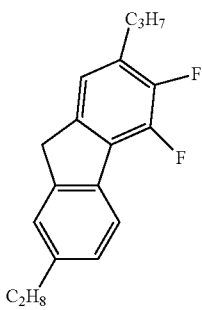
formula (156)
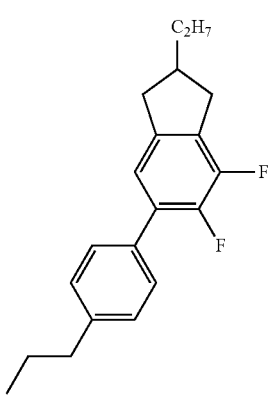
formula (157)
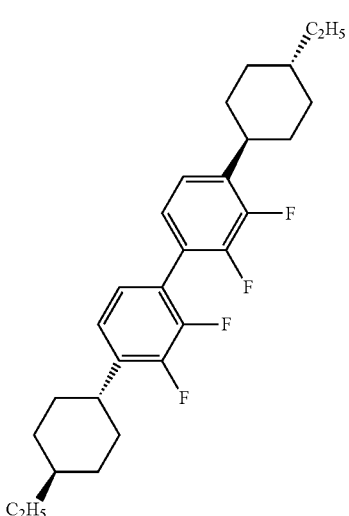
formula (158)
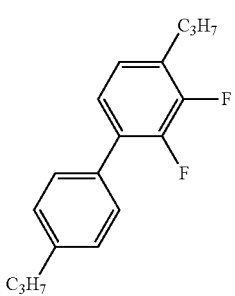
formula (159)

formula (160) 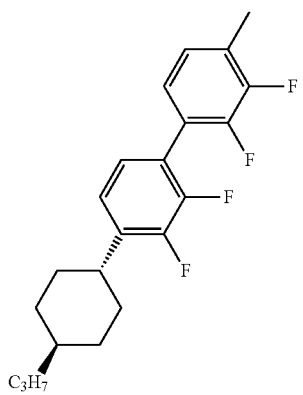
formula (161) 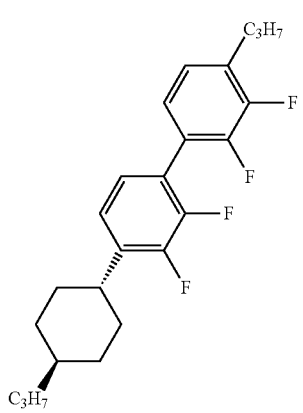
formula (162) 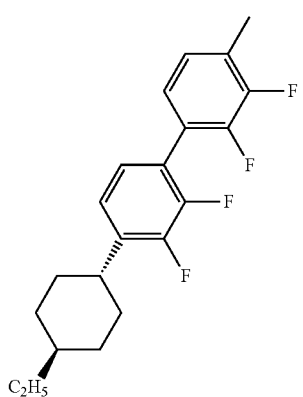
formula (163) 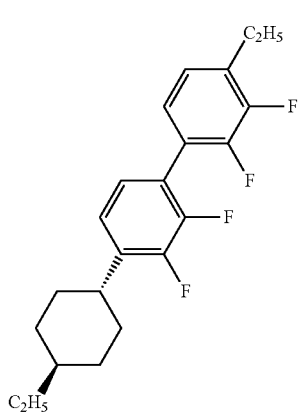
formula (164) 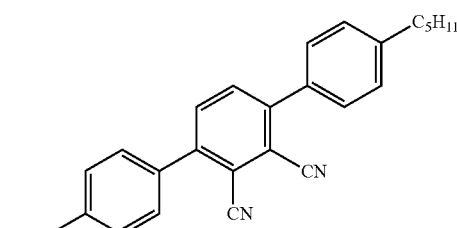
formula (165) 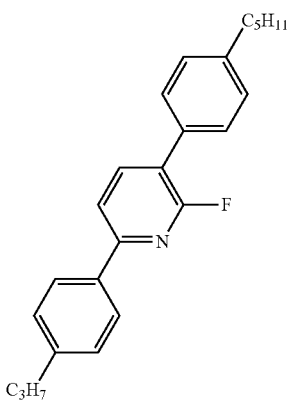
formula (166) 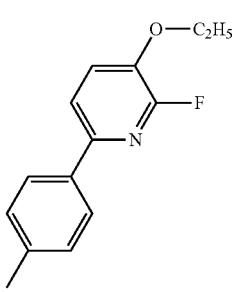
formula (167) 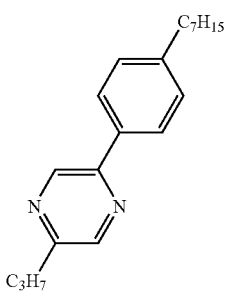

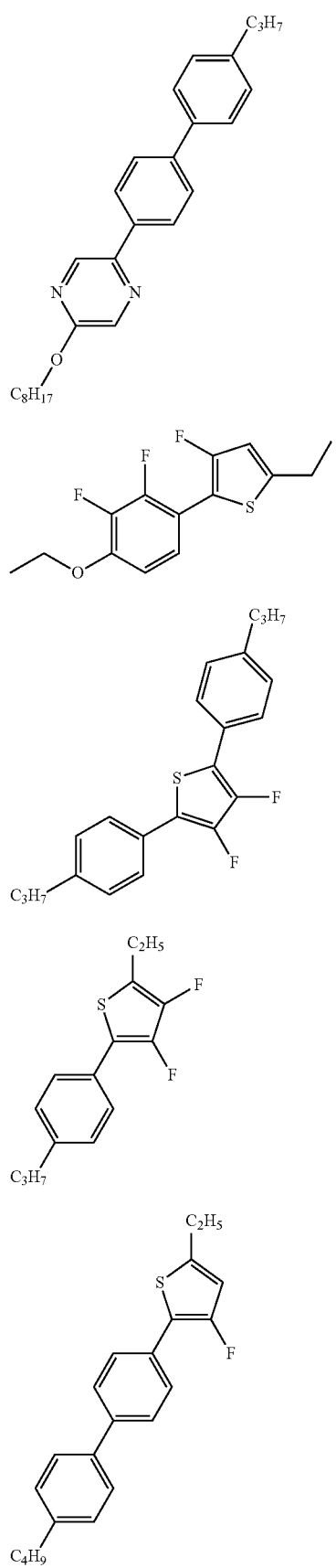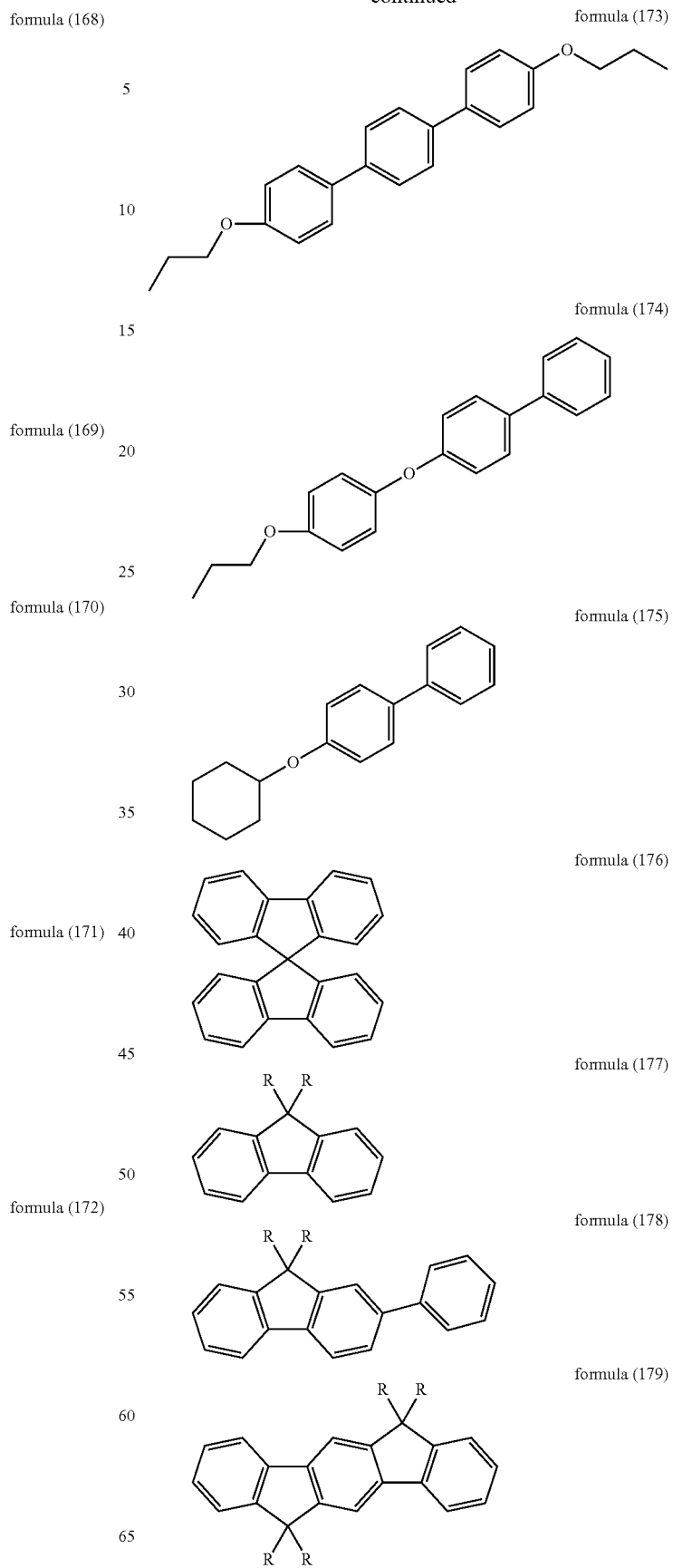
formula (168)
formula (169)
formula (170)
formula (171)
formula (172)
formula (173)
formula (174)
formula (175)
formula (176)
formula (177)
formula (178)
formula (179)

formula (180)
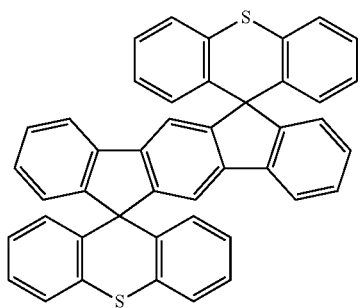
formula (181)
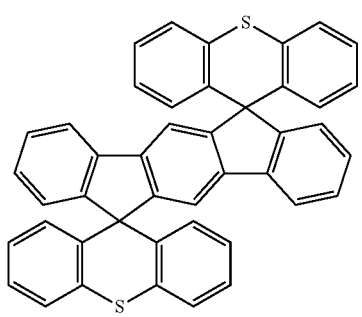
formula (182)
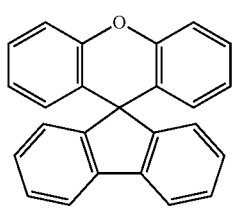
formula (183)
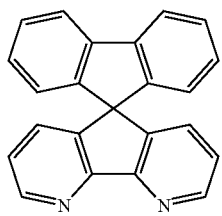
formula (184)
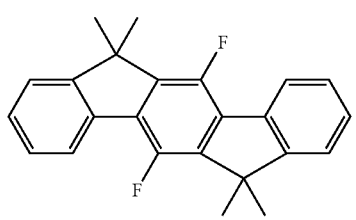
formula (185)
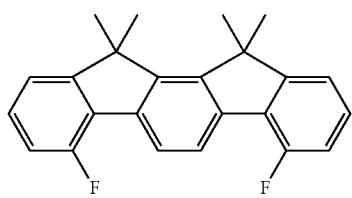
formula (186)
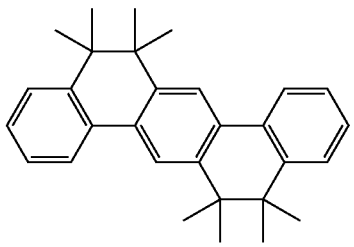
formula (187)
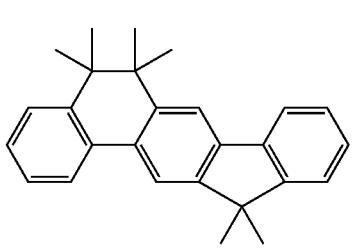
formula (188)
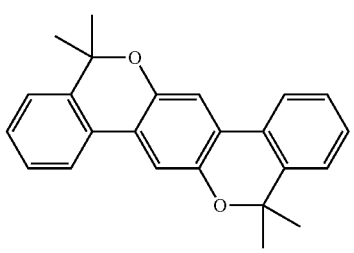
formula (189)
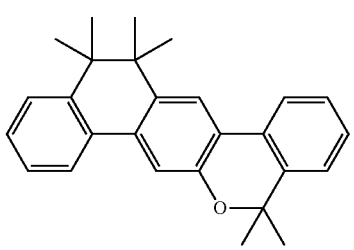
formula (190)
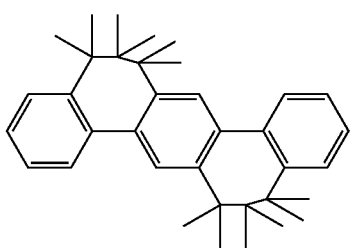
formula (191)
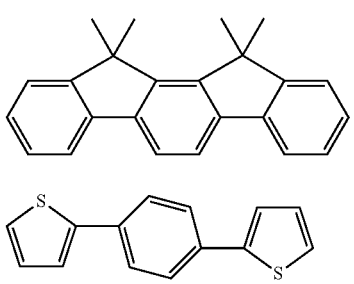
formula (192)

formula (193)

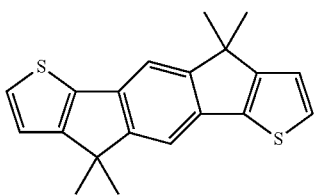

formula (194)

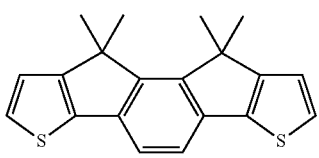

formula (195)

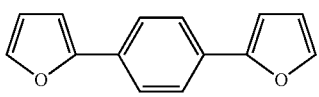

formula (196)

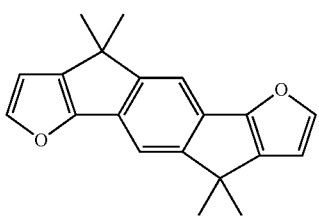

formula (197)

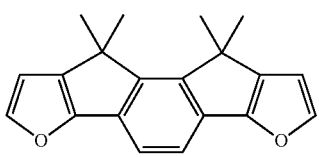

formula (198)

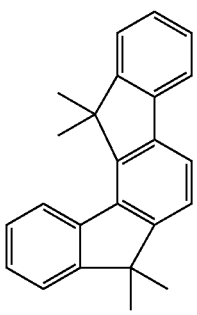

formula (199)

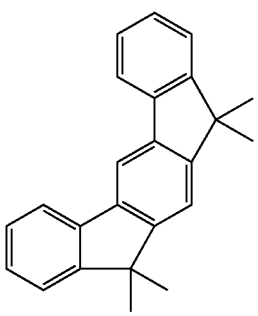

formula (200)

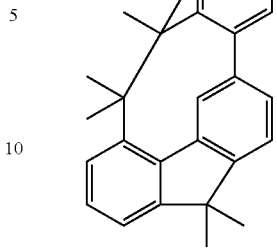

formula (201)

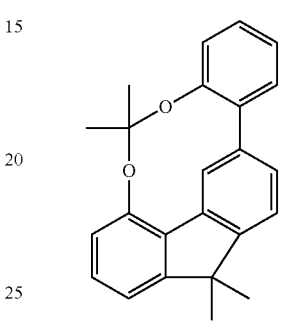

formula (202)

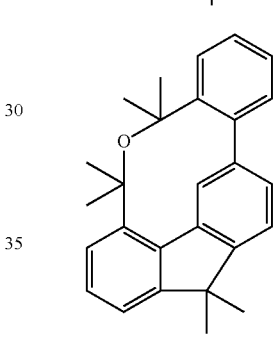

where R is defined like $R^1$.

In an embodiment, the emitting layer of the device according to the invention comprises an emitter of the formula (1) and at least one host material. The host material here has a larger band gap (=separation between valence band (LUMO—lowest unoccupied molecular orbital) and conduction band (HOMO—highest occupied molecular orbital)) or a higher excited electronic state. The host material consequently has a higher $S_1$ or $T_1$ level, preferably the $S_1$ level of the host material is higher than that of the emitter. $S_1$ here is the first electronically excited singlet level. $T_1$ is the first electronically excited triplet level.

The emitting layer preferably comprises an emitter of the formula (1) or (18), where n is equal to 1, or an emitter of the formulae (19) to (26).

The above-mentioned materials can be employed as emitters in the emission layer. However, the materials of the formula (1) can also be employed as host materials. The host compound of the formula (1) can be doped either with at least one dopant (emitter) of any desired type or with at least one emitter of the formula (1). The present invention therefore also relates to an electroluminescent device which is characterised in that the emission layer comprises at least one compounds of the formula (1) as host material in the emission layer.

The present invention therefore also relates to an electroluminescent device which is characterised in that the emission layer comprises at least one compound of the formula (1) as host material and at least one compound of the formula (1) as emitter in the emission layer.

Furthermore preferably, the emitting layer comprises a host material of the formula (1) or (18), where n is equal to 0.

In a very preferred embodiment, the emitting layer comprises an emitter of the formula (1) or (18), where n is equal to 1, or formula (19) to (26), and at least one host compound of the formula (1) or (18), where n is equal to 0.

Preference is furthermore given in the sense of the present invention to the use of polystyrene or of derivatives of polystyrene as host material.

In a further embodiment, the emitting layer comprises at least one further UV emitter and/or at least one further host material.

Suitable materials for the emitting layer, either as emitter or as host, are compiled by way of example in the following table with the corresponding references.

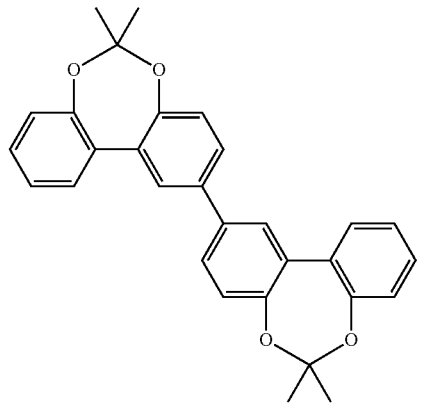

formula (205)

Zhang et al., J. Phys. Chem. B, 108, 9571, 2004

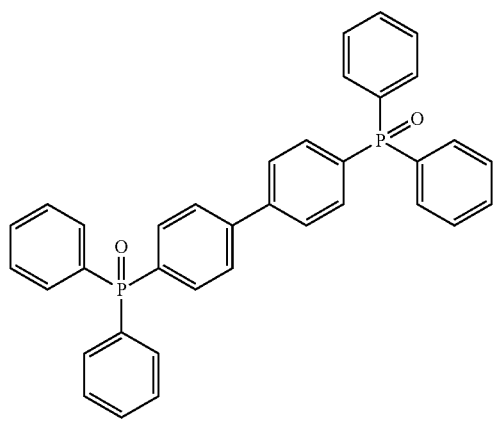

formula (203)

Burrows et al., Appl. Phys. Lett., 88, 183503, 2006

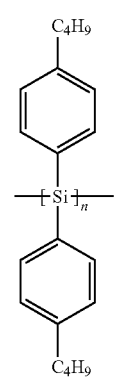

formula (206)

Hoshino et al., J. Appl. Phys., 88, 2892, 2000

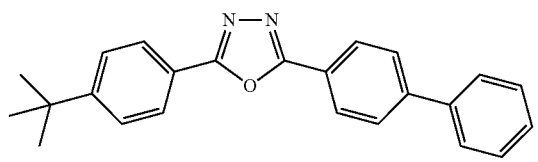

formula (207)

Zou et al., Appl. Phys. Lett., 79, 2282, 2001

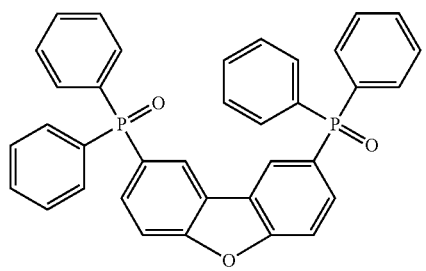

formula (204)

Vecchi et al., Organic Letters, 8, 4211, 2006

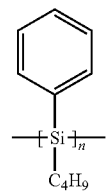

formula (208)

Sharma et al., Appl. Phys. Lett., 88, 143511, 2006 formula (209)
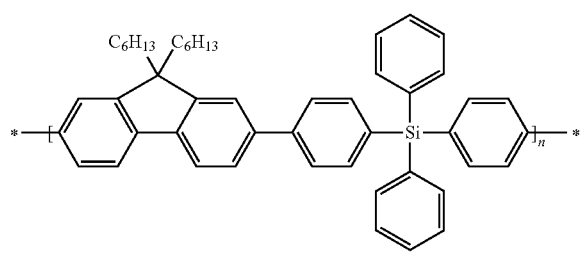
Zhou et al., Macromolecules, 40, 3015, 2007
formula (210)
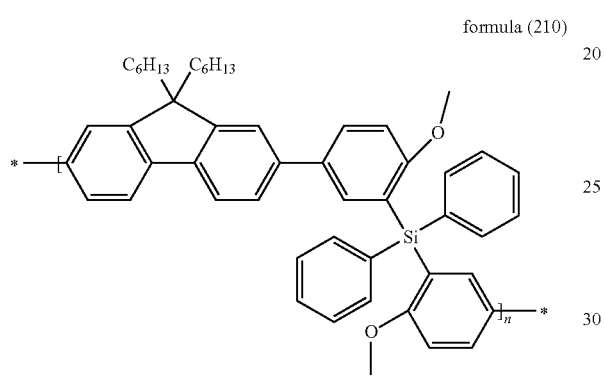
Zhou et al., Macromolecules, 40, 3015, 2007
formula (211)
Zhou et al., Macromolecules, 40, 3015, 2007
formula (212)
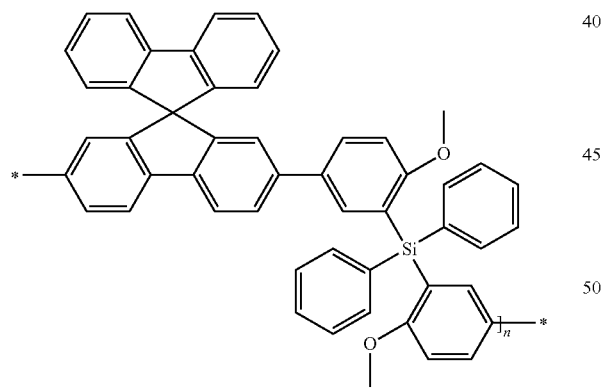
Wong et al., Organic Letters, 7, 5131, 2005
formula (213)
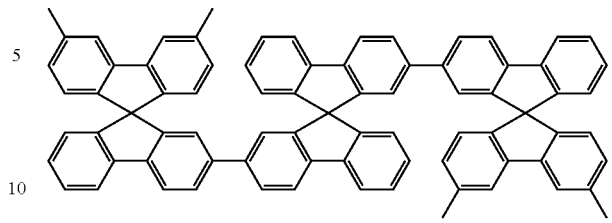
Wong et al., Organic Letters, 7, 5131, 2005
formula (214)
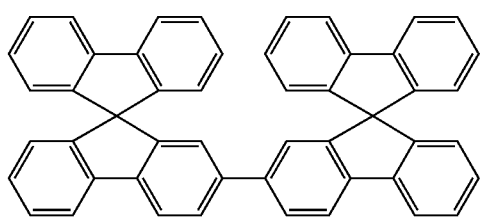
Chao et al., Adv. Mater., 17, 992, 2005
formula (215)
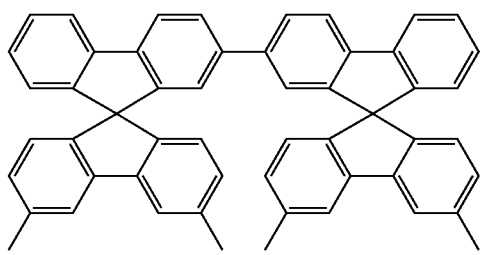
Chao et al., Adv. Mater., 17, 992, 2005
formula (216)
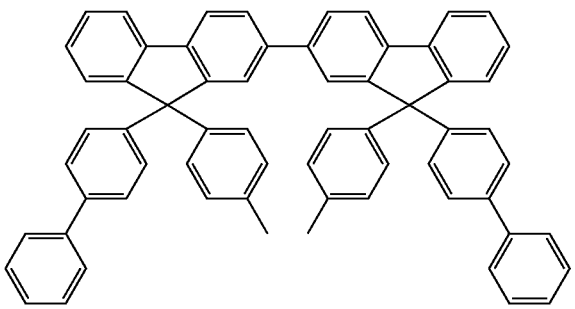
Chao et al., Adv. Mater., 17, 992, 2005
formula (217)
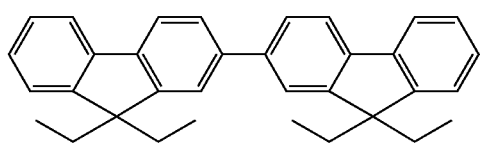
Chao et al., Adv. Mater., 17, 992, 2005 formula (218)
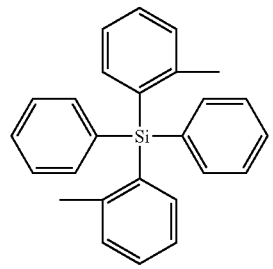
Ren et al., Chem. Mater., 16, 4743, 2004
formula (219)
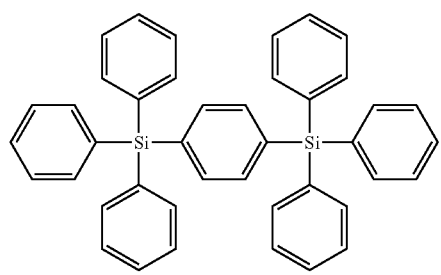
Ren et al., Chem. Mater., 16, 4743, 2004
formula (220)
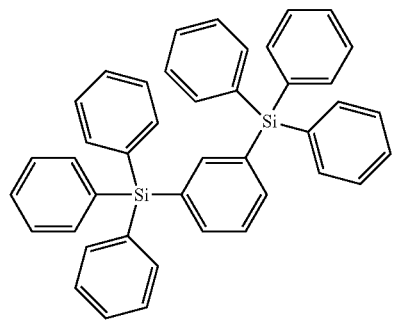
Ren et al., Chem. Mater., 16, 4743, 2004
formula (221)
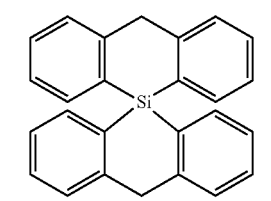
Ren et al., Chem. Mater., 16, 4743, 2004
formula (222)
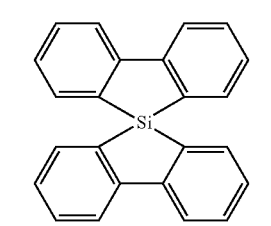
Ren et al., Chem. Mater., 16, 4743, 2004
formula (223)
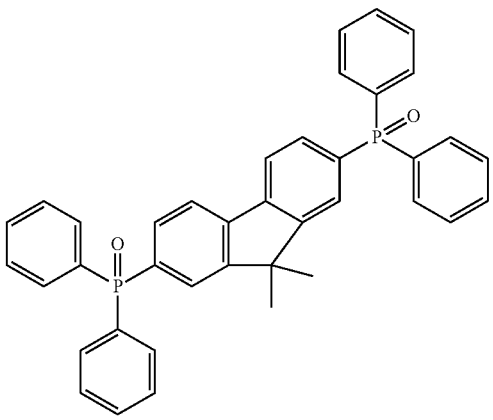
Padmaperuma et al., Chem. Mater., 18, 2389, 2006
formula (224)
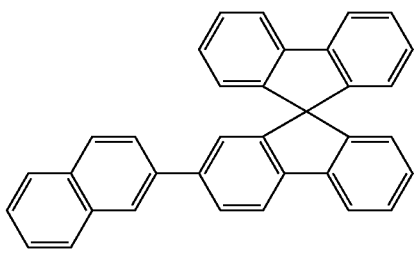
Etori et al., Jpn. J. Appl. Phys., 46, 5071, 2007
formula (225)
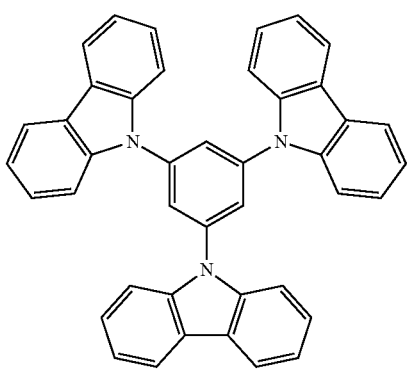
Etori et al., Jpn. J. Appl. Phys., 46, 5071, 2007

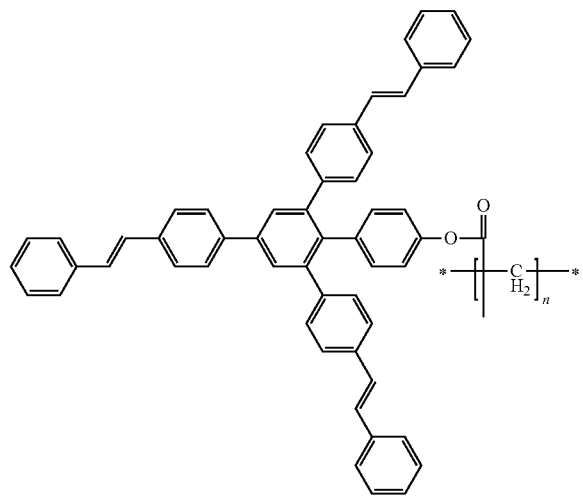

formula (226)

Spiliopoulos et al.,
Macromolecules, 35, 7254, 2002

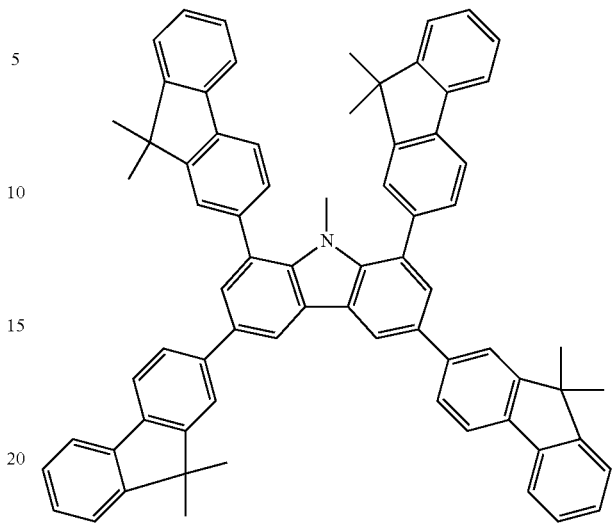

formula (230)

Niu et al., RSC Adv., 1, 415, 2011

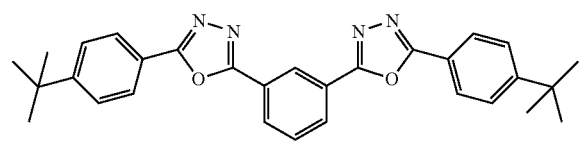

formula (227)

Ichikawa et al., Thin Solid Films, 515, 3932, 2007

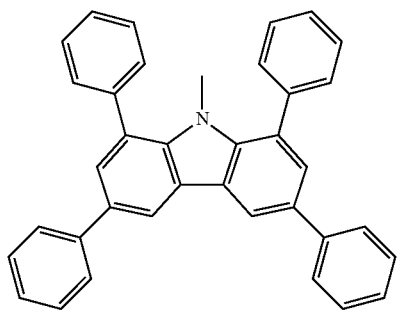

formula (228)

Niu et al., RSC Adv., 1, 415, 2011

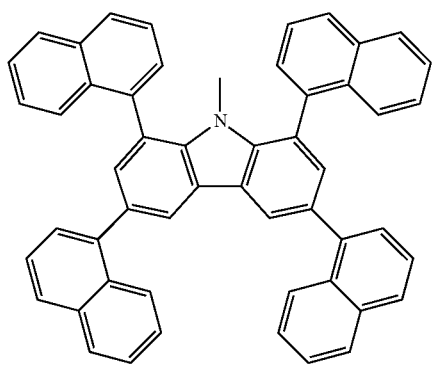

formula (229)

Niu et al., RSC Adv., 1, 415, 2011

The performance data of the devices according to the invention can be improved further in various ways.

As already mentioned, at least one host material is usually used in the emission layer of organic electroluminescent devices besides the emitter or emitters. However, particularly good results can be achieved on use of a mixed-host system in the device according to the invention.

In a further preferred embodiment, a mixed host is used in the emission layer of the device according to the invention. This enables the radiation intensities of the devices to be significantly increased and the operating voltages to be significantly reduced. Mixed host means that the host consists of at least 2 different compounds. The mixed host preferably comprises at least one compound of the formula (1). In addition, the mixed host comprises a further host compound of any desired type. The person skilled in the art will be able to fall back here without difficulties on a multiplicity of host compounds known in the prior art. In a very preferred embodiment, the mixed host comprises at least one compound of the formula (1), where n is equal to 0, or at least one compound of the formulae (19) or (22).

In a further embodiment, further layers are introduced between the emitting layer and one of the two electrodes.

It is advantageous if at least one blocking layer is used between EML and one of the electrodes. This enables, in particular, the operating voltage to be reduced and the absolute radiation intensities to be increased. Suitable blocking layers can block excitons, electrons or holes.

The present invention therefore also relates to a device, as disclosed herein, which comprises a further layer between the emitting layer and one of the two electrodes, characterised in that the additional layer comprises an exciton-blocking material (blocking material) having a band gap of 3.4 eV or higher, preferably 3.6 eV or higher, very preferably 3.8 eV or higher and very particularly preferably 4.0 eV or higher.

The present invention also relates to a device, as disclosed herein, which comprises a further layer between the emitting layer and one of the two electrodes, characterised in that the additional layer comprises a hole-blocking material (blocking material) having an HOMO of lower than −5.9 eV, preferably lower than −6.0 eV, very preferably lower than −6.2 eV and very particularly preferably lower than −6.3 eV.

The present invention also relates to a device, as disclosed herein, which comprises a further layer between the emitting layer and one of the two electrodes, characterised in that the additional layer comprises an electron-blocking material (blocking material) having an LUMO of higher than −2.2 eV, preferably higher than −2.1 eV.

In a very preferred embodiment, the device according to the invention comprises a blocking layer which blocks both excitons and also holes.

In a further very preferred embodiment, the device according to the invention comprises a blocking layer which blocks both excitons and also electrons.

The blocking material employed in the blocking layer can be all materials which satisfy the above-mentioned criteria. These also include the compounds of the general formula (1). The present invention furthermore relates to an electroluminescent device comprising at least two electrodes, at least one emitting layer between the electrodes, and at least one blocking layer between the emitting layer and one of the two electrodes which comprises at least one compound of the general formula (1), where n=0, with the proviso that the compound of the formula (1) contains no condensed aromatic or heteroaromatic ring systems and with the proviso that the compound of the formula (1) contains no conjugated moiety containing more than 16, preferably more than 14 and very preferably more than 12 conjugated π (pi) electrons.

The blocking material is preferably a compound of the general formulae (19) or (22).

In a very preferred embodiment, the blocking layer is formed by crosslinking one or more compounds containing at least 2 or more crosslinkable group (hereafter precursor). Especial preference is given to a blocking layer which is formed by precursor of the compound of the formula (1), where n=0, or formula (19) or formula (22), which furthermore contain at least 2 or more crosslinkable group.

A crosslinkable group is a group containing a crosslinkable reagent which results in a crosslinking reaction with the aid of heat, radiation or both. The radiation source can be an electron beam and UV radiation. The preferred UV radiation source emits radiation of a wavelength of 200 to 400 nm, very preferably a radiation of 300 to 400 nm. Suitable sources for UV radiation are, for example, mercury UV fluorescent lamps, UV LEDs and UV laser diodes.

Suitable crosslinkable groups are, for example, the acrylate group (for example Scheler et al., In Macromol. Symp. 254, 203-209 (2007)), the vinyl or styrene group (for example WO 2006/043087) and the oxetane group (for example Mueller et al., In Nature 421, 829-833 (2003)).

In a preferred embodiment, the precursor compound for the blocking layer is a compound of the general formula (231).

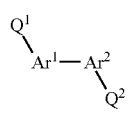

formula (231)

where $Ar^1$ and $Ar^2$ are defined as above, and $Q^1$ and $Q^2$ is each, independently of one another, a crosslinkable group, which is preferably selected from the following formula (232) to (255):

formula (232)

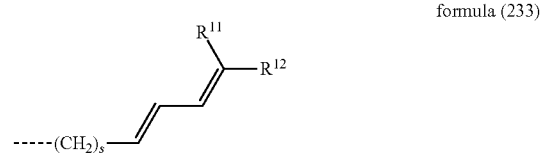

formula (233)

formula (234)

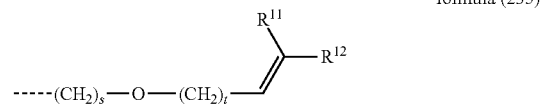

formula (235)

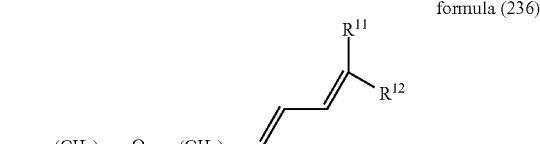

formula (236)

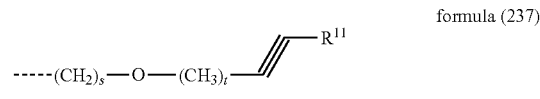

formula (237)

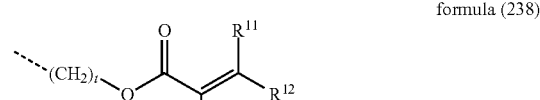

formula (238)

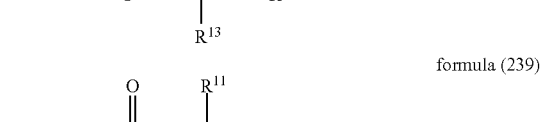

formula (239)

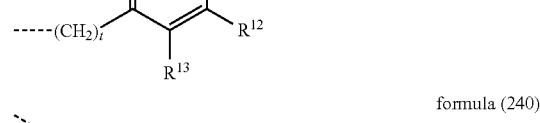

formula (240)

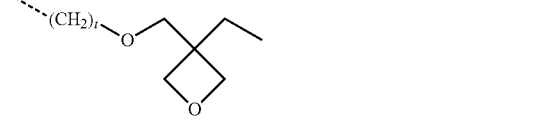

formula (241)

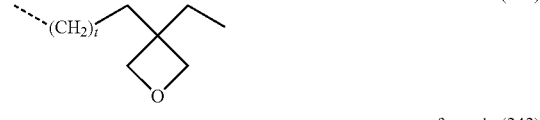

formula (242)

formula (243)

formula (244)

-continued

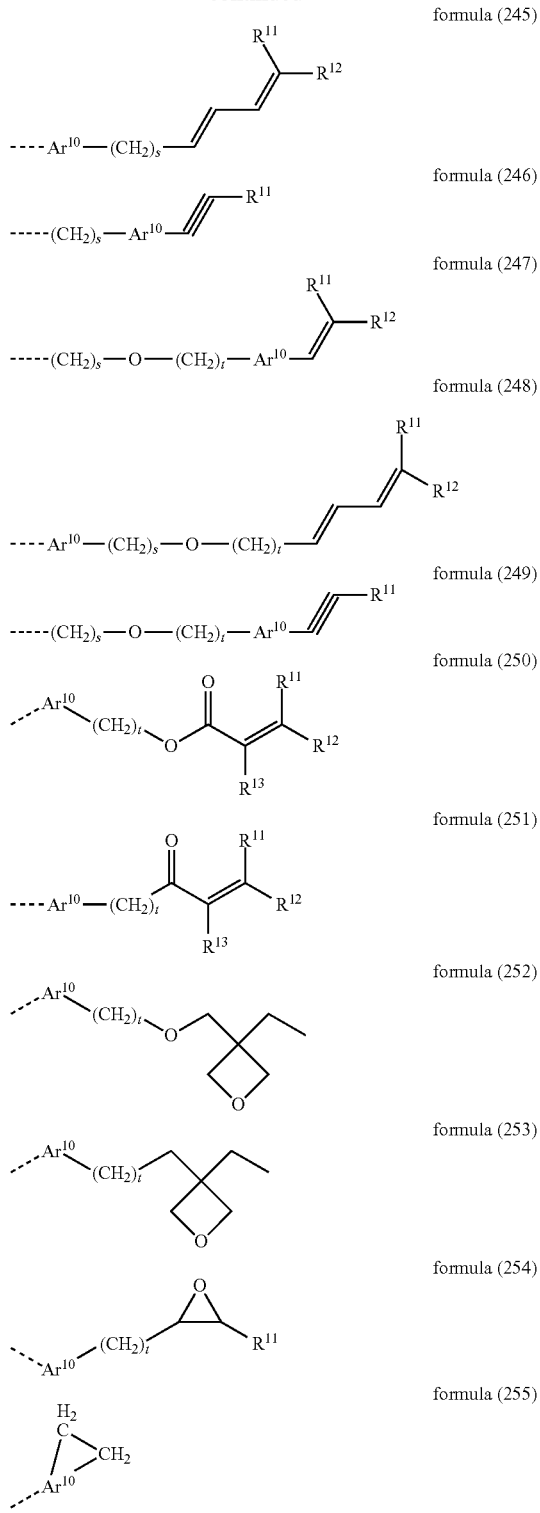

formula (245)
formula (246)
formula (247)
formula (248)
formula (249)
formula (250)
formula (251)
formula (252)
formula (253)
formula (254)
formula (255)

where
the radicals $R^{11}$, $R^{12}$ and $R^{13}$ are on each occurrence, identically or differently, H, a straight-chain or branched alkyl group having 1 to 6 C atoms;
$Ar^{10}$ in the formulae (244) to (255) is a mono- or polycyclic, aromatic or heteroaromatic ring system having 5 or 6 ring atoms, which may be substituted by one or more radicals R, where R is on each occurrence, identically or differently, H, D, F or an aliphatic, aromatic and/or heteroaromatic hydrocarbon radical having 1 to 20 C atoms, in which, in addition, one or more H atoms may be replaced by F; where two or more substituents R may also form a mono- or polycyclic, aliphatic or aromatic ring system with one another;
s is an integer from 0 to 8;
t is an integer from 1 to 8;
and where the dashed bond represent the linking of the crosslinkable group to one of the mono- or polycyclic, aromatic or heteroaromatic ring systems $Ar^1$ or $Ar^2$ in formula (231).

In the group of the formula (243), the two dashed lines mean that $Ar^1$ and/or $Ar^2$ in the compound of the formula (231) are connected in the ortho position to the two carbon atoms of the ethylene group, so that a four-membered ring forms. Analogously, $Ar^{10}$ in the group of the formula (255) is connected to the two carbon atoms of the ethylene group in the ortho position, so that a four-membered ring forms.

Examples of preferred precursor compounds for the blocking layer in accordance with the embodiments indicated above are the compounds of the following structures.

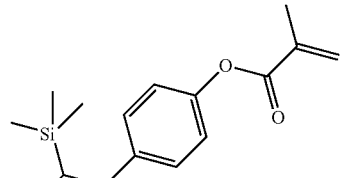

formula (256)

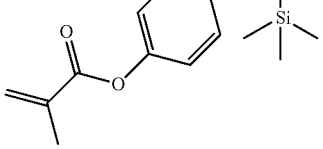

formula (257)

formula (258)
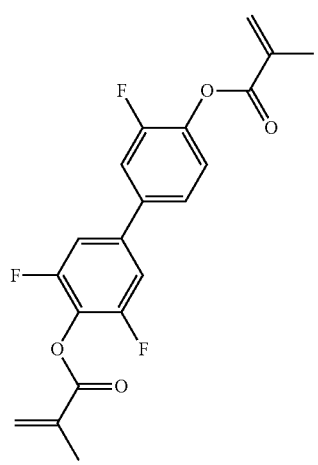
formula (259)
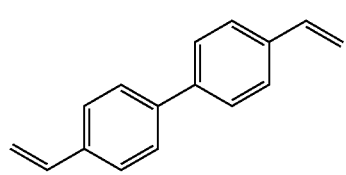
formula (260)
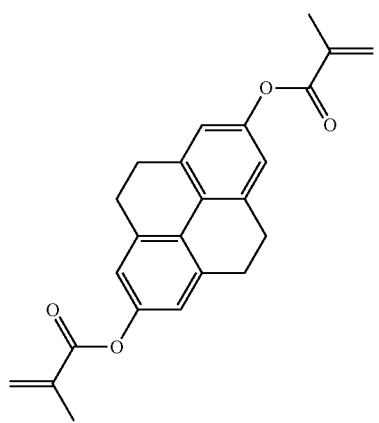
formula (261)
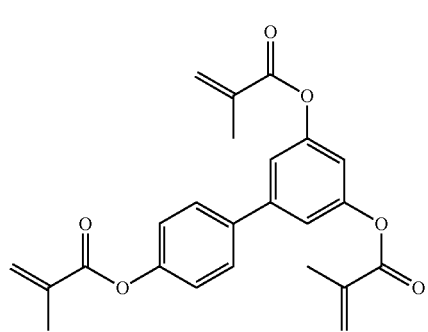
formula (262)
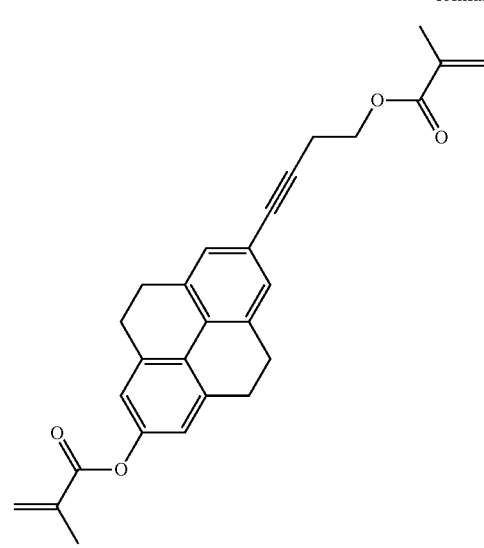
formula (263)
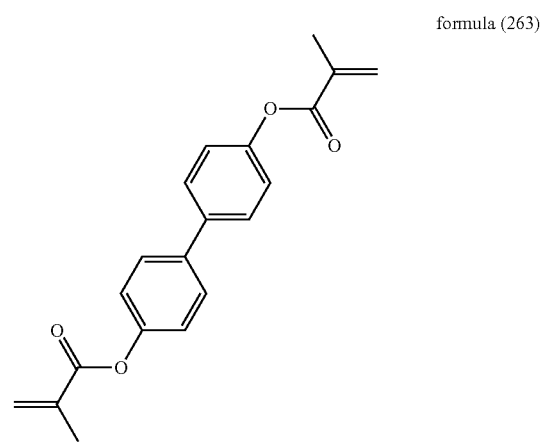
formula (264)
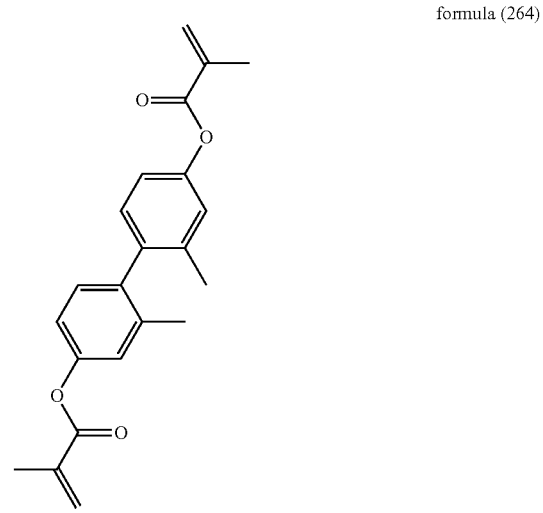

formula (265)
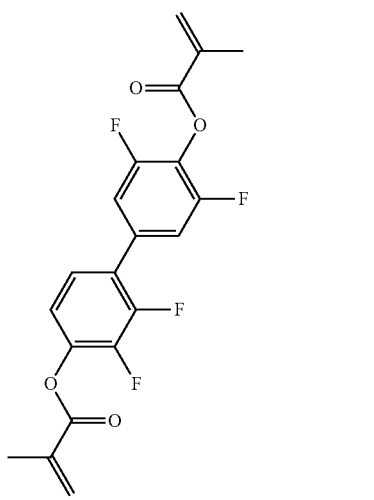
formula (266)
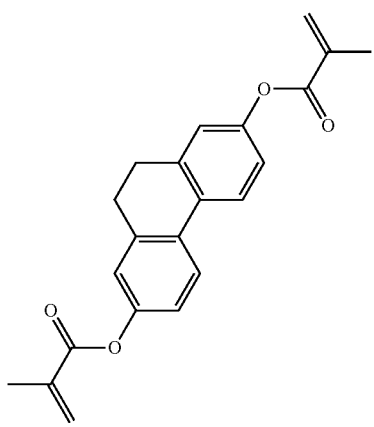
formula (267)
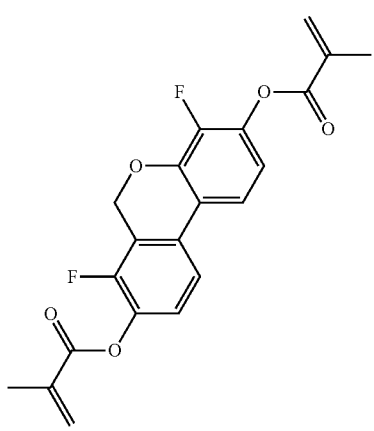
formula (268)
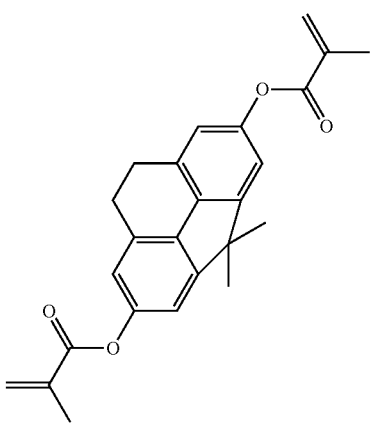
formula (269)
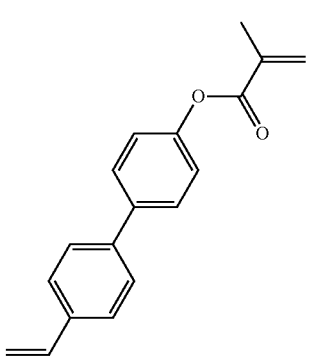
formula (270)
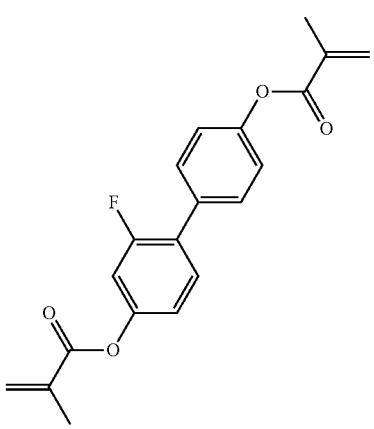
formula (271)
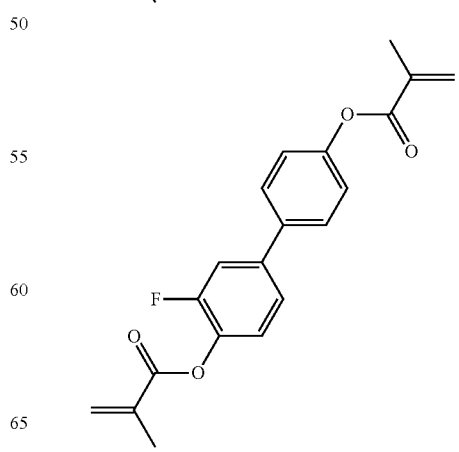

formula (272)

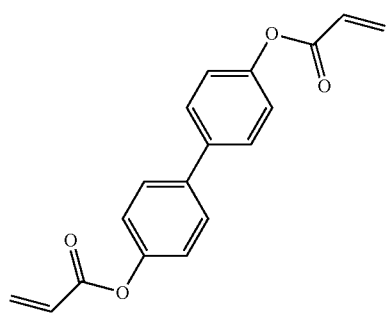

formula (273)

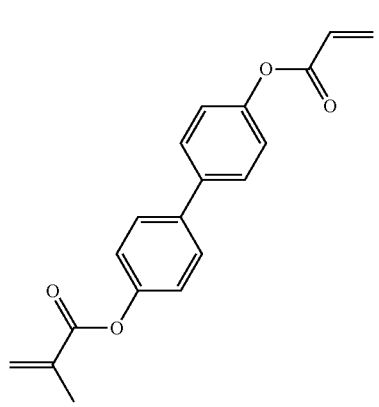

formula (274)

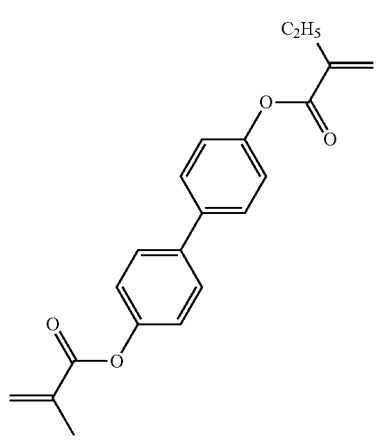

formula (275)

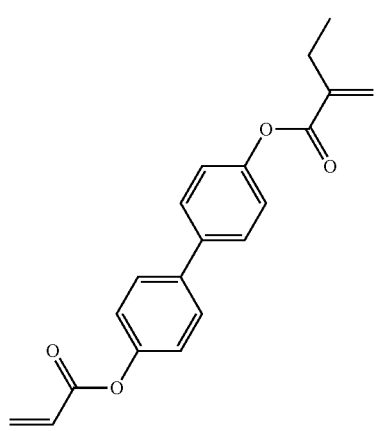

formula (276)

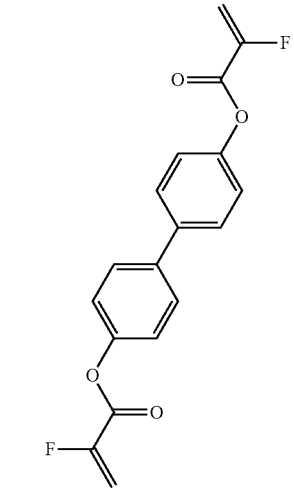

formula (277)

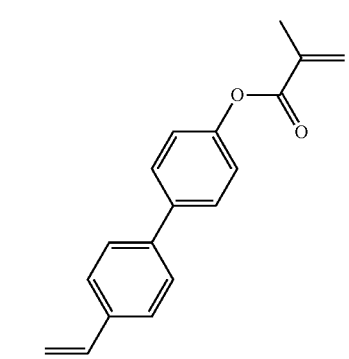

formula (278)

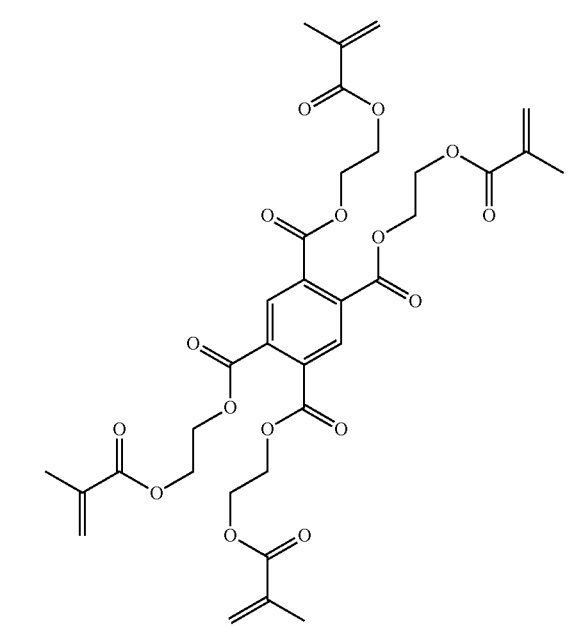

Processes for the preparation of the said precursor compounds are well known to the person skilled in the art from the prior art (for example WO 2010/133278 and U.S. Pat. No. 7,807,068).

The electroluminescent device can be any electroluminescent device. The person skilled in the art will be able to make a selection here without difficulties from a large number of devices known to him. The electroluminescent device is preferably an organic light-emitting diode (OLED), polymeric light-emitting diode (PLED), organic light-emitting electrochemical cell (OLEC, LEC or LEEC), an organic light-emitting transistor (O-LETs) and an organic light-emitting electrochemical transistor. In a very preferred embodiment, the present invention relates to OLEDs or PLEDs. In a furthermore very preferred embodiment, the present invention relates to OLECs.

The electroluminescent device comprises cathode, anode and at least one emitting layer. Apart from these layers, it may also comprise further layers, for example in each case one or more hole-injection layers, hole-transport layers, hole-blocking layers, electron-transport layers, electron-injection layers, exciton-blocking layers and/or charge-generation layers. Interlayers, which have, for example, an exciton-blocking function, may likewise be introduced between two emitting layers. However, it should be pointed out that each of these layers does not necessarily have to be present. The electroluminescent device may comprise one emitting layer, or it may comprise a plurality of emitting layers, where it is preferred if it comprises one emitting layer.

In a preferred embodiment, the electroluminescent device according to the invention comprises a hole-injection layer, which is also called buffer layer. The work function of the hole-injection layer is greater than 5.0 eV, preferably greater than 5.4 eV, very preferably greater than 5.8 eV and very particularly preferably greater than 6.0 eV. In a further embodiment, the hole-injection layer comprises conductive, conjugated polymers, such as, for example, polythiophene, polyaniline and polypyrrole and derivatives thereof. Such polymers are in some cases also commercially available, such as, for example, CLEVIOS™ P VP AI 4083, CLEVIOS™ HIL 1.3, and CLEVIOS™ HIL 1.3N from Heraeus Precious Metals GmbH & Co. KG.

The compounds of the formula (1) may also be incorporated into the side chain of polymers. The incorporation of the compounds into the side chain of polymers has various advantages, which are shown below.
1) The polymers have improved solubility in organic solvents and thus also improved processability.
2) The polymers have improved layer-formation properties.
3) The polymers have higher glass transition temperatures (Tg) compared with small molecules.
4) The polymers have a broader process window and improved performance data.

The invention therefore also relates to a polymer of the general formula (279)

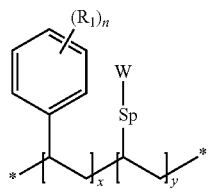

formula (279)

where the following applies to the indices and symbols used:
Sp is a single bond or a non-conjugated spacer;
W is, identically or differently on each occurrence, a structural unit of the formula (1), where the bonding between Sp and the compound of the formula (1) can take place at any desired and chemically possible position;
x is a number between 0 and 80 and stands for mol % of the respective unit;
y is a number from 2 to 100 and stands for mol % of the respective unit, where x+y=100 mol %;
n is an integer from 0 to 5;
$R^1$ is defined like $R^3$ in formula (1);
where the polymer preferably has a photoluminescence and/or electroluminescence emission in the wavelength range from 280 and 380 nm.

In a further preferred embodiment of the present invention, the polymer according to the invention emits both radiation in the wavelength range from 280 to 380 nm and also radiation in the wavelength range from 400 to 500 nm.

In a preferred embodiment, the spacer is a hydrocarbon radical having 1 to 20 C atoms, where alkyl and alkylalkoxy radicals are preferred.

In a preferred embodiment, the polymer according to the invention has the general formula (280)

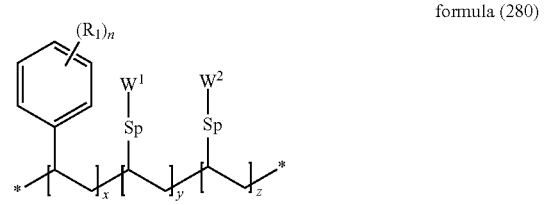

formula (280)

where the following applies to the indices and symbols used:
x is a number between 0 and 80 mol %;
y is a number from 19 to 80 mol %;
z is a number from 1 to 20 mol %, where x+y+z=100 mol %;
$W^1$ is selected from the compounds of the formulae (19), (22), (61), (64), (89-2), (89-4);
$W^2$ is selected from the compounds of the formulae (20), (21), (23), (24), (25), (26), (62), (63), (65), (66), (67), (68), (89-1), (89-3), (89-5) and (89-6);
and where the other symbols and indices are defined as indicated in formula (279).

In a preferred embodiment, Sp is a single bond. It is very preferred if the aromatic or heteroaromatic rings of W, $W^1$ or $W^2$ are bonded directly to the polymer backbone.

In a very particularly preferred embodiment, the polymer is one of the following general compounds.

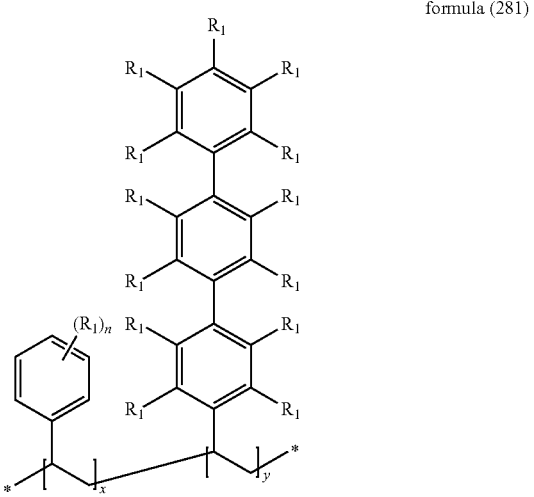

formula (281)

formula (282)

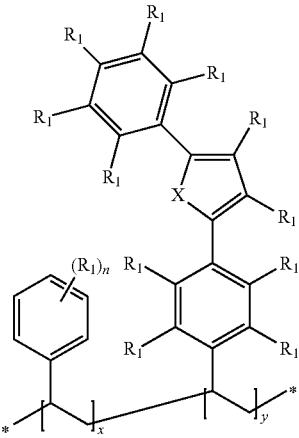

formula (283)

formula (284)

formula (285)

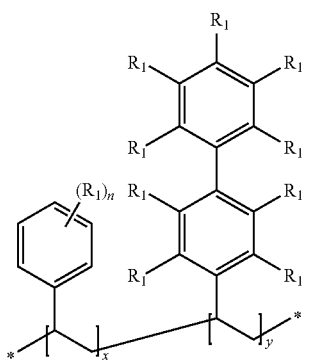

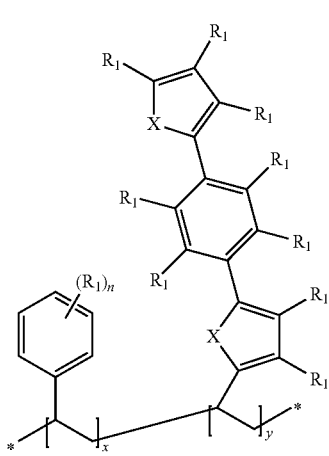

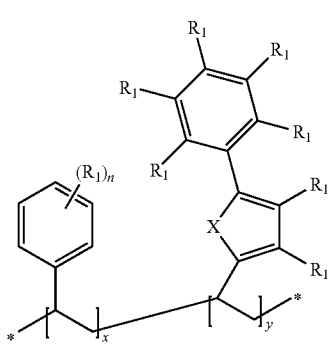

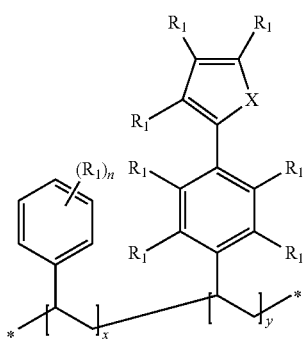

formula (286)

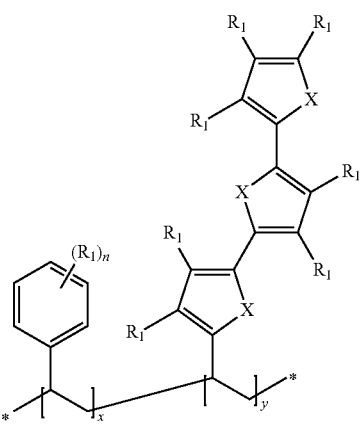

formula (287)

where X and $R^1$ are defined as in formula (89-1) to (89-6) and where the preferred embodiments for $R^1$ indicated in connection with the compound of the formula (1) also represent preferred embodiments for $R^1$ in connection with the polymer according to the invention.

The following general synthetic procedures can be used for the preparation of polymers of the formula (279):

Synthesis Route 1

Free-Radical Polymerisation for Polymers of the Formulae (281) to (287)

The monomers are weighed out in the desired ratio into a flask and carefully rendered inert. 10 equivalents of toluene relative to the total amount of monomer are added, and the solution is rendered inert again. In a second flask, 0.01 equivalents of AIBN relative to the total amount of monomer are weighed out and dissolved in ten times the molar amount of toluene with gentle warming. The monomer solution is heated to 70° C., and one percent of the toluene/AIBN solution is added rapidly by means of a syringe. The solution is stirred at 70° C. for 72 hours with exclusion of light, then cooled to room temperature and stirred for a further 24 hours. The polymer is precipitated twice from toluene in ethanol, filtered off and dried in a high vacuum for 24 hours.

Synthesis Route 2

Anionic Polymerisation for Polymers of the Formulae (281) to (287)

32 equivalents of freshly dried and distilled cyclohexane relative to the total amount of monomer are added to a dried flask, and 0.002 equivalents of 2-butyllithium in hexane (1.4 M) relative to the total amount of monomer is added. The solution is warmed to 45° C., and the monomers are added rapidly in the desired ratio. The reaction mixture is stirred at the temperature for between 4 minutes and 10 hours, then added dropwise to a solution of degassed methanol. The polymer is precipitated twice from toluene in ethanol, filtered off and dried in a high vacuum for 24 hours.

Synthesis Route 3

Cationic Polymerisation for Polymers of the Formulae (281) to (287)

The monomers 1-phenylethyl chloride (0.043 eq) and dibutyl ether (0.34 eq) are initially introduced in a flask, and ten times the volume of a mixture of 1,2-dichloroethane and n-hexane (55:45 v/v) is added. The reaction mixture is cooled to −15° C., and a solution of titanium(IV) chloride in 1,2-dichloroethane (4 M, 0.172 eq) is added. The reaction mixture is stirred at the temperature for between 4 minutes and 10 hours, then added dropwise to a solution of degassed ethanol. The solid is washed a number of times with 0.5 M nitric acid and deionised water. The polymer is precipitated twice from toluene in ethanol, filtered off and dried in a high vacuum for 24 hours.

The invention furthermore relates to a formulation comprising at least one polymer according to the invention and at least one solvent.

The invention also relates to a composition comprising at least one polymer according to the invention and at least one organic functional material or an organic semiconductor, as described below.

The invention furthermore relates to an electroluminescent device comprising at least one of the polymers according to the invention. The preferred electroluminescent devices here are the devices described above, where the OLEDs/PLEDs and OLECs are also very particularly preferred here.

The present invention also relates to compositions comprising at least one of the compounds of the formula (1) or at least one polymer of the general formula (279) and at least one organically functional material or an organic semiconductor selected from the group of the emitters, host materials, matrix materials, electron-transport materials (ETM), electron-injection materials (EIM), hole-transport materials (HTM), hole-injection materials (HIM), electron-blocking materials (EBM), hole-blocking materials (HBM), exciton-blocking materials (ExBM), where the definitions from Claim 1 apply to the symbols indicated and the index n. The emitters can be both fluorescent and phosphorescent emitters. The person skilled in the art will be able to make a selection here without difficulties from a multiplicity of known organic functional materials having the said functions. The definitions and examples of various organic functional materials can be obtained, for example, from the disclosure content of WO 2011/015265.

For the purposes of the present invention, the composition according to the invention preferably comprises at least one host material as organically functional material besides at least one compound of the formula (1) or at least one polymer of the formula (279) as emitter. The composition very preferably comprises two host materials besides the at least one compound of the formula (1) or besides the at least one polymer of the formula (279) as emitter. The composition very particularly preferably comprises precisely one compound of the formula (1) or precisely one polymer of the formula (279) as emitter and two host materials. The composition furthermore very particularly preferably comprises precisely one compound of the formula (1) or polymer of the formula (279) as emitter and precisely one host material.

In a furthermore preferred embodiment, the composition according to the invention, besides at least one compound of the formula (1) or at least one polymer of the formula (279) as host, comprises at least one emitter as organically functional material. The composition very preferably comprises an emitter besides the at least two compound of the formula (1) or besides the at least two polymers of the formula (279) as host. The composition very particularly preferably comprises precisely one compound of the formula (1) or precisely one polymer of the formula (279) as host and an emitter material of the formula (1) or of the formula (279). The composition furthermore very particularly preferably comprises precisely two compounds of the formula (1) or (279) as mixed host and an emitter of the formula (1) or (279).

The concentration of emitter(s) in the composition is 2 to 50 wt % (percent by weight), preferably 5 to 40 wt % and very preferably 7 to 30 wt %. The total concentration of the host or host materials is 50 to 98 wt %, preferably 95 to 60 wt % and very preferably 93 to 70 wt %.

The devices according to the invention can be produced by various processes. One or more of the layers of the electroluminescent device can be applied by means of a sublimation process, in which the materials are applied by vapour deposition in vacuum sublimation units at an initial pressure less than $10^{-5}$ mbar, preferably less than $10^{-6}$ mbar. However, it is also possible for the initial pressure to be even lower, for example less than $10^{-7}$ mbar.

A preferred process for the application of one or more layers of the electroluminescent device is the OVPD process (organic vapour phase deposition) or a process with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., Appl. Phys. Lett. 2008, 92, 053301).

One or more of the layers of the electroluminescent device can also be applied from solution, such as, for example, by spin coating, or by means of any desired printing process, such as, for example, screen printing, flexographic printing, offset printing, LITI (light induced thermal imaging, thermal transfer printing), ink-jet printing or nozzle printing. Soluble compounds, which are obtained, for example, by suitable substitution, are necessary for this purpose. These processes are also suitable for the application of layers comprising oligomers, dendrimers and polymers.

Likewise possible are hybrid processes, in which, for example, one or more layers are applied from solution and one or more other layers are applied by vacuum vapour deposition.

The present invention therefore also relates to a process for the production of the electroluminescent devices according to the invention by means of sublimation processes and/or by means of processes from solution.

The present invention furthermore relates to a formulations comprising a composition according to the invention and one or more solvents.

Suitable and preferred solvents are, for example, toluene, anisole, xylenes, methyl benzoate, dimethylanisoles, trimethylbenzenes, tetralin, veratrols, tetrahydrofuran, chlorobenzene or dichlorobenzenes and mixtures thereof.

Electroluminescent devices which emit blue light and/or UV radiation can be employed in a versatile manner. Applications which require light or radiation having very short wavelengths and thus represent areas of application for the devices according to the invention are found, for example, in the area of life science and medicine (for example for cell imaging) or in the area of biosensors. The devices according to the invention are furthermore used in the electronics industry, solid-state lighting and for the curing of polymers and printing ink. The present invention therefore also relates to the use of the electroluminescent devices according to the invention in the said areas.

The devices according to the invention can also be employed for the light therapy (phototherapy) of humans and/or animals. The present invention therefore furthermore relates to the use of the devices according to the invention for the treatment, prophylaxis and diagnosis of diseases by means of phototherapy. The present invention still furthermore relates to the use, of the devices according to the invention for the treatment and prophylaxis of cosmetic conditions by means of phototherapy.

Phototherapy or light therapy is used in many areas of medicine and/or cosmetics. The devices according to the invention can therefore be employed for the therapy and/or prophylaxis and/or diagnosis of all diseases and/or in cosmetic applications for which the person skilled in the art considers using phototherapy. Besides irradiation, the term phototherapy also includes photodynamic therapy (PDT) as well as preservation, disinfection and sterilisation in general. It is not only humans or animals that can be treated by means of phototherapy or light therapy, but also any other type of living or non-living materials. These include, for example, fungi, bacteria, microbes, viruses, eukaryotes, prokaryotes, foods, drinks, water, drinking water, cutlery, medical instruments and equipment and other devices.

The term phototherapy also includes any type of combination of light therapy and other types of therapy, such as, for example, treatment with active compounds. Many light therapies have the aim of irradiating or treating exterior parts of an object, such as the skin of humans and animals, wounds, mucous membranes, the eye, hair, nails, the nail bed, gums and the tongue. In addition, the treatment or irradiation according to the invention can also be carried out inside an object in order, for example, to treat internal organs (heart, lung, etc.) or blood vessels or the breast.

The therapeutic and/or cosmetic areas of application according to the invention are preferably selected from the group of skin diseases and skin-associated diseases or changes or conditions, such as, for example, psoriasis, skin ageing, skin wrinkling, skin rejuvenation, enlarged skin pores, cellulite, oily/greasy skin, folliculitis, actinic keratosis, precancerous actinic keratosis, skin lesions, sun-damaged and sun-stressed skin, crows' feet, skin ulcers, acne, acne rosacea, scars caused by acne, acne bacteria, photomodulation of greasy/oily sebaceous glands and their surrounding tissue, jaundice, jaundice of the newborn, vitiligo, skin cancer, skin tumours, Crigler-Najjar, dermatitis, atopic dermatitis, diabetic skin ulcers, and desensitisation of the skin.

Particular preference is given for the purposes of the invention to the treatment and/or prophylaxis of psoriasis, acne, cellulite, skin wrinkling, skin ageing, jaundice and vitiligo.

Further areas of application according to the invention for the devices are selected from the group of inflammatory diseases, rheumatoid arthritis, pain therapy, treatment of wounds, neurological diseases and conditions, oedema, Paget's disease, primary and metastasising tumours, connective-tissue diseases or changes in the collagen, fibroblasts and cell level originating from fibroblasts in tissues of mammals, irradiation of the retina, neovascular and hypertrophic diseases, allergic reactions, irradiation of the respiratory tract, sweating, ocular neovascular diseases, viral infections, particularly infections caused by herpes simplex or HPV (human papillomaviruses) for the treatment of warts and genital warts.

Particular preference is given for the purposes of the invention to the treatment and/or prophylaxis of rheumatoid arthritis, viral infections and pain.

Further areas of application according to the invention for the devices are selected from winter depression, sleeping sickness, irradiation for improving the mood, the reduction in pain particularly muscular pain caused by, for example, tension or joint pain, elimination of the stiffness of joints and the whitening of the teeth (bleaching).

Further areas of application according to the invention for the devices are selected from the group of disinfections. The devices can be used for the treatment of any type of objects (non-living materials) or subjects (living materials such as, for example, humans and animals) for the purposes of disinfection, sterilisation or preservation. This includes, for example, the disinfection of wounds, the reduction in bacteria, the disinfection of surgical instruments or other articles, the disinfection or preservation of foods, of liquids, in particular water, drinking water and other drinks, the disinfection of mucous membranes and gums and teeth. Disinfection here is taken to mean the reduction in the living microbiological causative agents of undesired effects, such as bacteria and germs.

The devices according to the invention emit, in particular, in the UV and blue region of the spectrum. The precise wavelength can be adjusted towards longer wavelengths without difficulties by the person skilled in the art depending on the respective application.

In a particularly preferred embodiment of the present invention, the device is an organic light-emitting diode (OLED) or an organic light-emitting electrochemical cell (OLEC) which are employed for the purposes of phototherapy. Both the OLED and the OLEC can have a planar or fibre-like structure having any desired cross section (for example round, oval, polygonal, square) with a single- or multilayered structure. These OLECs and/or OLEDs can be installed in other devices which comprise further mechanical, adhesive and/or electronic elements (for example battery and/or control unit for adjustment of the irradiation times, intensities and wavelengths). These devices comprising the OLECs and/or OLEDs according to the invention are preferably selected from the group comprising plasters, pads, tapes, bandages, sleeves, blankets, hoods, sleeping bags, textiles and stents.

The use of the said devices for the said therapeutic and/or cosmetic purpose is particularly advantageous compared with the prior art, since homogeneous irradiation in the high-energy blue region and/or in the UV region of lower irradiation intensities is possible at virtually any site and at any time of day with the aid of the devices according to the invention using the OLEDs and/or OLECs. The irradiation can be carried out as an inpatient, as an outpatient and/or by the patient themselves, i.e. without introduction and/or guidance by medical or cosmetic specialists. Thus, for example, plasters can be worn under clothing, so that irradiation is also possible during working hours, in leisure time or during sleep. Complex inpatient/outpatient treatments can in many cases be avoided or their frequency reduced. The devices according to the invention may be intended for re-use or be disposable articles, which can be disposed of after use once, twice or more times.

Further advantages over the prior art are, for example, lower evolution of heat and emotional aspects. Thus, newborn being treated owing to jaundice typically have to be irradiated blindfolded in an incubator without physical contact with the parents, which represents an emotional stress situation for parents and newborn. With the aid of a blanket according to the invention comprising the OLEDs and/or OLECs according to the invention, the emotional stress can be reduced significantly. In addition, better temperature control of the child is possible due to reduced heat production of the devices according to the invention compared with conventional irradiation equipment.

The present invention therefore also relates, in particular, to the device according to the invention for use in medicine for phototherapy.

The present invention also relates to the device according to the invention for use for the treatment of the skin by means of phototherapy.

The present invention also relates to the device according to the invention for use for the treatment of psoriasis by means of phototherapy.

The present invention also relates to the device according to the invention for use for the treatment of jaundice by means of phototherapy.

The present invention also relates to the device according to the invention for use for the treatment of jaundice of the newborn by means of phototherapy.

The present invention also relates to the device according to the invention for use for the treatment of acne by means of phototherapy.

The present invention also relates to the device according to the invention for use for the treatment of inflammation by means of phototherapy.

The present invention also relates to the device according to the invention for use for the treatment of atopic eczema by means of phototherapy.

The present invention also relates to the device according to the invention for use for the treatment of skin ageing by means of phototherapy The present invention furthermore relates to the use of the devices according to the invention in the cosmetics area for phototherapy.

In particular, the present invention relates to the use of the devices according to the invention for the phototherapeutic reduction and/or for the phototherapeutic prevention of the formation of skin wrinkles and skin ageing.

The present invention also relates to a method for the treatment of the skin by phototherapy using a device according to the invention.

An aryl group in the sense of this invention contains 6 to 40 C atoms; a heteroaryl group in the sense of this invention contains 1 to 39 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (anellated) aryl or heteroaryl group, for example naphthalene, anthracene, phenanthrene, quinoline, isoquinoline, etc. Aromatic groups which are linked to one another by a single bond, such as, for example, biphenyl, are, by contrast, not referred to as aryl or heteroaryl group, but instead as aromatic ring system.

An aromatic ring system in the sense of this invention contains 6 to 60 C atoms in the ring system. A heteroaromatic ring system in the sense of this invention contains 1 to 59 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be linked by a non-aromatic unit, such as, for example, a C, N or O atom. Thus, for example, systems such as fluorene, 9,9'-spirobifluorene, 9,9-diarylfluorene, triarylamine, diaryl ether, stilbene, etc., are also intended to be taken to be aromatic ring systems for the purposes of this invention, as are systems in which two or more aryl groups are interrupted, for example, by a short alkyl group. Furthermore, systems in which a plurality of aryl and/or heteroaryl groups are linked to one another by a single bond, such as, for example, biphenyl, terphenyl or bipyridine, are intended to be taken to be an aromatic or heteroaromatic ring system.

For the purposes of the present invention, an aliphatic hydrocarbon radical or an alkyl group or an alkenyl or alkynyl group, which may typically contain 1 to 40 or also 1 to 20 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenyithio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent $CH_2$ groups may be replaced by $R^1C=CR^1$, $C\equiv C$, $Si(R^1)_2$, $Ge(R^1)_2$, $Sn(R^1)_2$, $C=O$, $C=S$, $C=Se$, $C=NR^1$, $P(=O)(R^1)$, SO, $SO_2$, $NR^1$, O, S or $CONR^1$; furthermore, one or more H atoms may also be replaced by D, F, Cl, Br, I, CN or $NO_2$, preferably F, Cl or CN, further preferably F or CN, particularly preferably CN.

An aromatic or heteroaromatic ring system having 5-60 aromatic ring atoms, which may also in each case be substituted by the above-mentioned radicals $R^1$ or a hydrocarbon radical and which may be linked to the aromatic or heteroaromatic ring system via any desired positions, is taken to mean, in particular, groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aryloxy group in accordance with the definition of the present invention is taken to mean an aryl group, as defined above, which is bonded via an oxygen atom. An analogous definition applies to heteroaryloxy groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The devices, compositions and formulations according to the invention are distinguished by the following surprising advantages over the prior art:
1. The devices according to the invention emit in the UV-A and UV-B region.
2. The emitter compounds required for the preferred emission are readily accessible.
3. The use of mixed hosts enables the operating voltage to be reduced and the radiation intensity to be increased.
4. The use of blocking layers enables the operating voltage to be significantly reduced and the radiation intensity to be increased.
5. The devices according to the invention can easily be processed from solution.

These above-mentioned advantages are not accompanied by an impairment in the other electronic properties.

It should be pointed out that variations of the embodiments described in the present invention fall within the scope of this invention. Each feature disclosed in the present invention can, unless explicitly excluded, be replaced by alternative features which serve the same, an equivalent or a similar purpose. Thus, each feature disclosed in the present invention should, unless stated otherwise, be regarded as an example of a generic series or as an equivalent or similar feature.

All features of the present invention can be combined with one another in any way, unless certain features and/or steps are mutually exclusive. This applies, in particular, to preferred features of the present invention. Equally, features of non-essential combinations can be used separately (and not in combination).

It should furthermore be pointed out that many of the features, and in particular those of the preferred embodiments of the present invention, should be regarded as inventive themselves and not merely as part of the embodiments of the present invention. Independent protection may be granted for these features in addition or as an alternative to each invention claimed at present.

The teaching regarding technical action disclosed with the present invention can be abstracted and combined with other examples.

The invention is explained in greater detail by the following examples and FIGS. 1 to 20 without wishing to restrict it thereby.

EXAMPLES

Example 1

Materials

Ref1

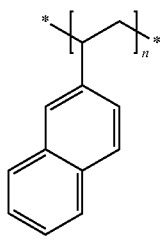

Ref2

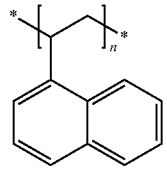

E1

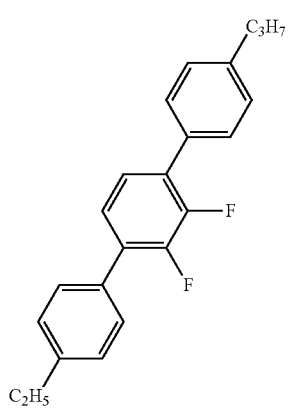

E2

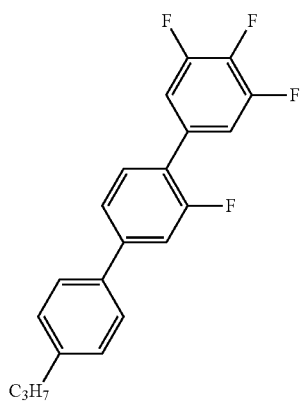

E3

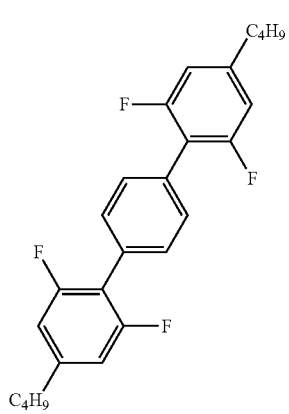

-continued
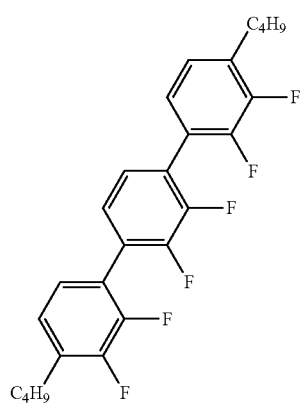
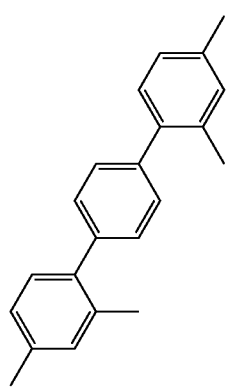
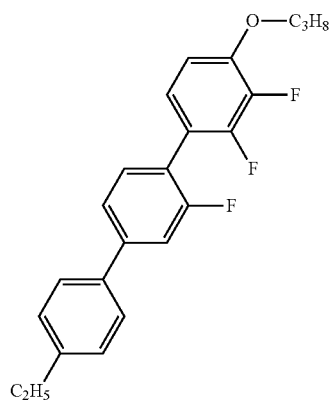
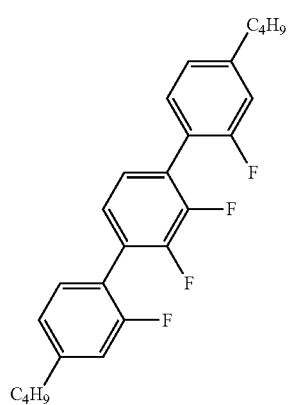
-continued
E4
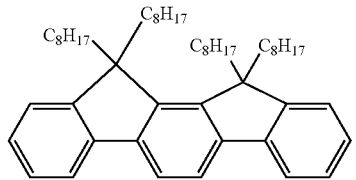
E6
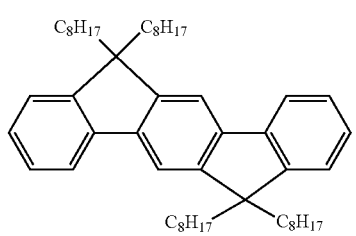
E7
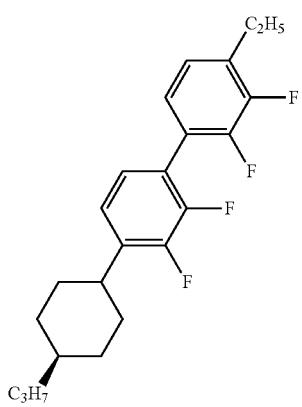
E8
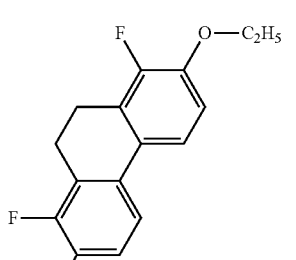
E9
E10
E11
E12
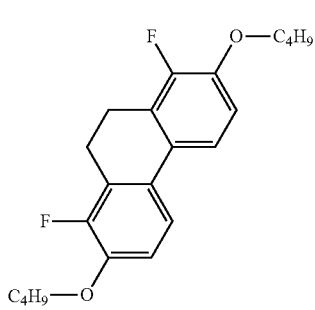
E13

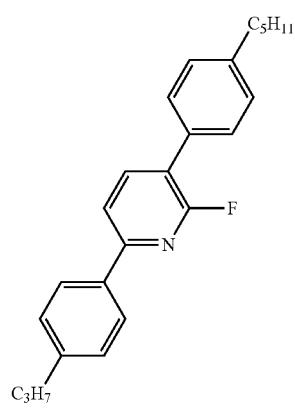
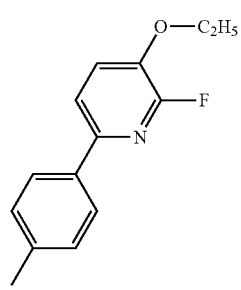
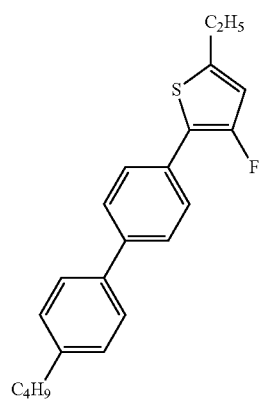
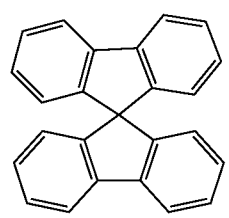
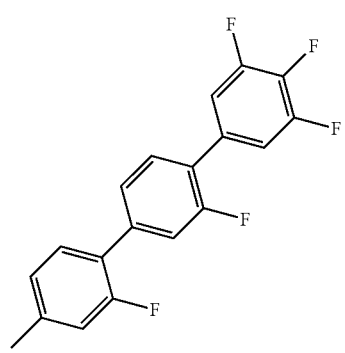
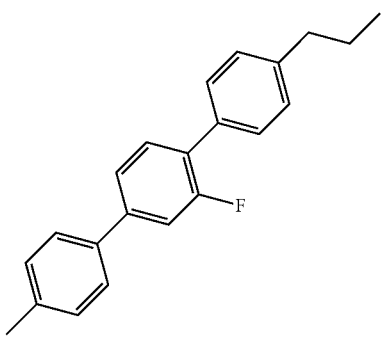
E14
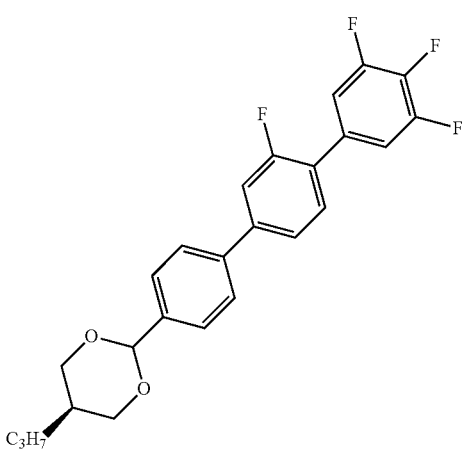
E15
E16
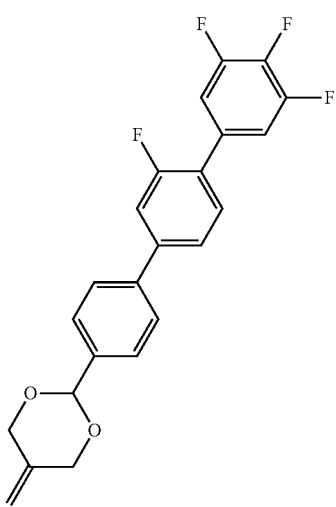
E17
E20
E21
E22
E23

-continued
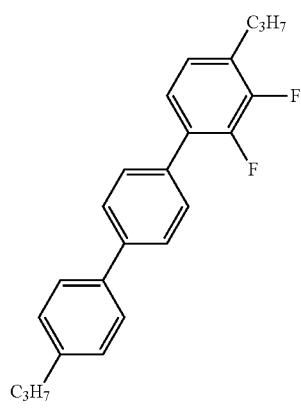
E24
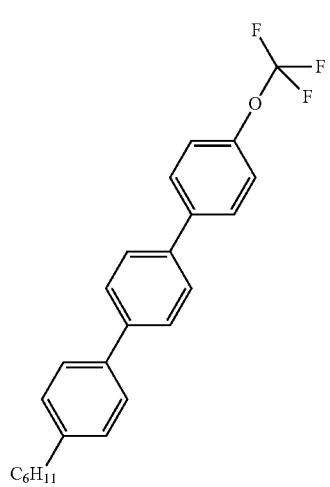
E25
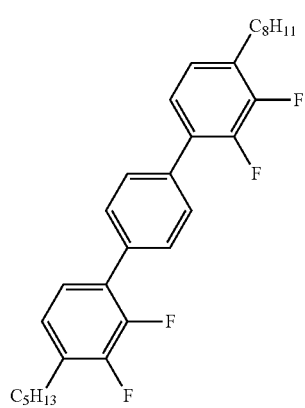
E26
-continued
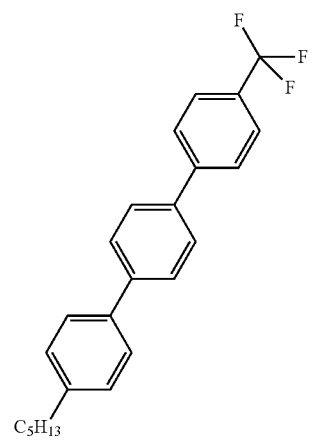
E27
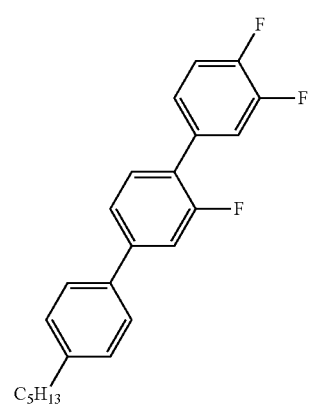
E28
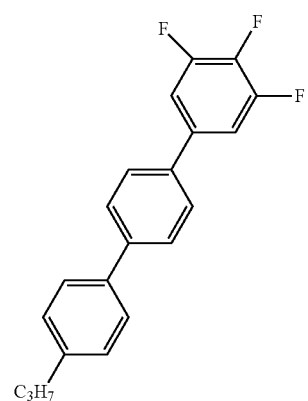
E29
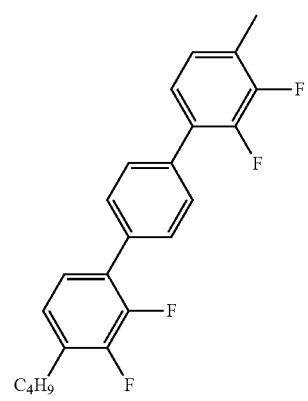
E30

-continued

E31 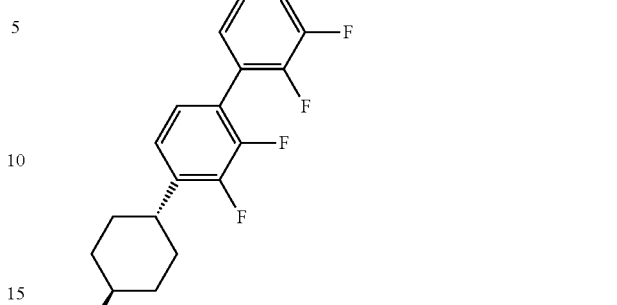 H1

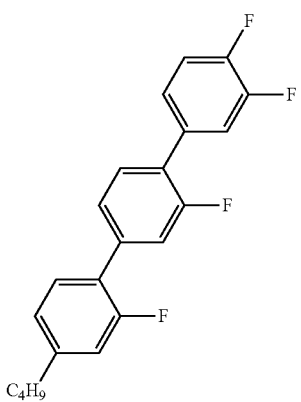

E32 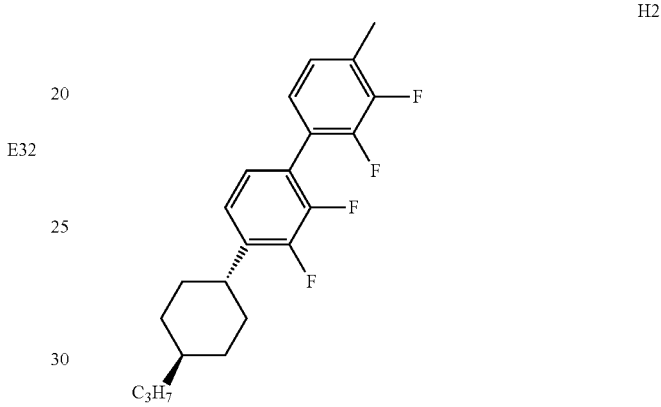 H2

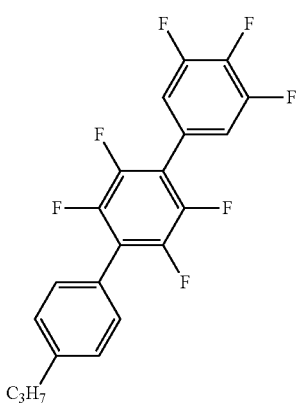

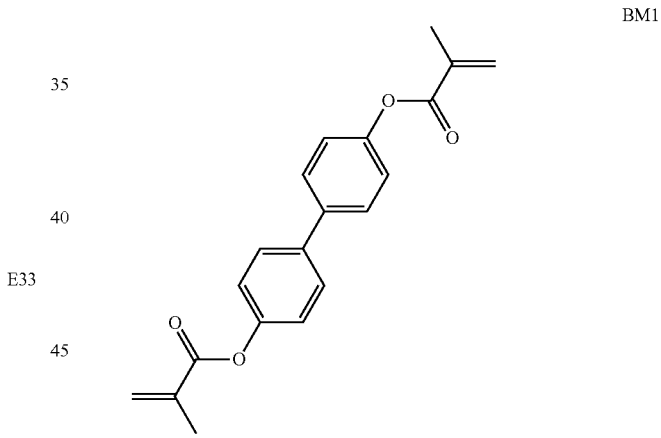 BM1

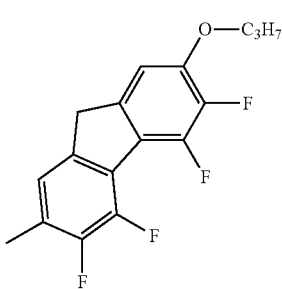

E33

E34 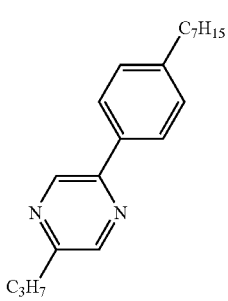

E1 to E34 are compounds of the formula (1). Ref1 (poly(2-vinylnaphthalene)) and Ref2 (poly(1-vinylnaphthalene)) are reference compounds and can be purchased from Sigma-Aldrich. H1 and H2 are host compounds. BM1 is a blocking material.

In addition, polystyrene (PS) from Fulka having a molecular weight Mw of 200 k Daltons is used.

Compounds E9, E10, E12, E13, E17, E33 and BM1 can be prepared in accordance with the following disclosures.

E9 Setayesh et al., Macromolecules, 33, 2016 (2000) and WO 2004/041901

E10 WO 2004/113412

E12 DE 19549741

E13 DE19549741

E33 EP 1223209, DE 10200040223914, U.S. Pat. No. 7,297,379, EP 1223210

BM1 EP 2033707 Wesslau, Makromolekulare Chemie 93, 55(1966)

The synthesis of other terphenyls or biphenyls are familiar to the person skilled in the art from the prior art. Compounds of the formula (89-1) to (89-6) can be synthesised, for example, by Suzuki coupling as follows:

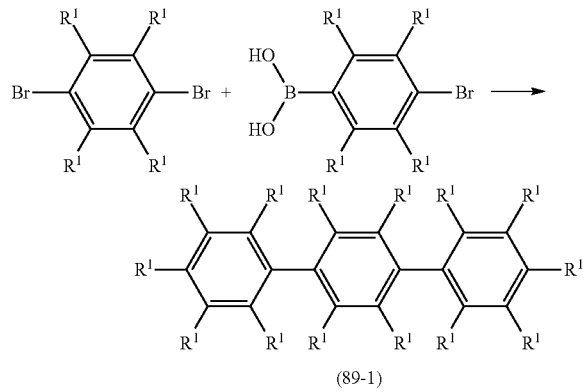

(89-1)

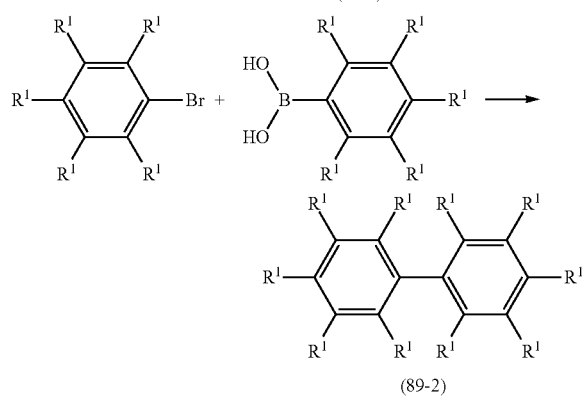

(89-2)

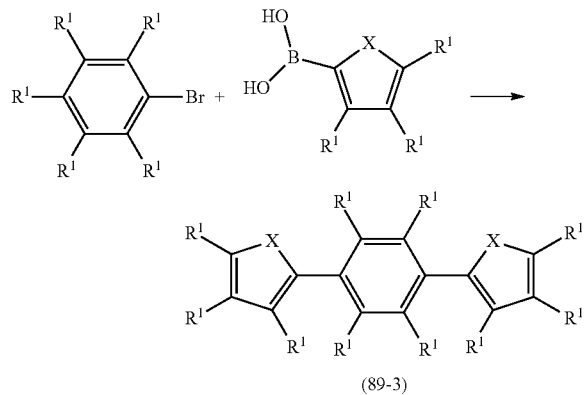

(89-3)

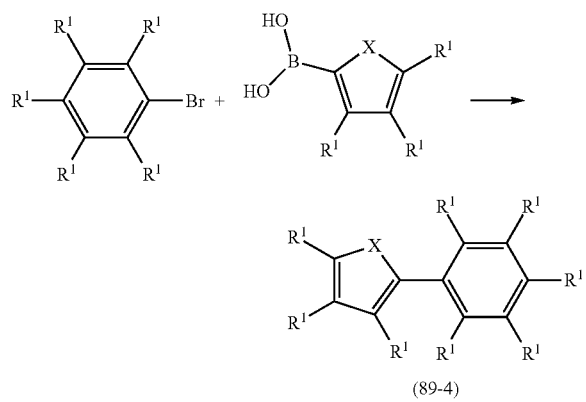

(89-4)

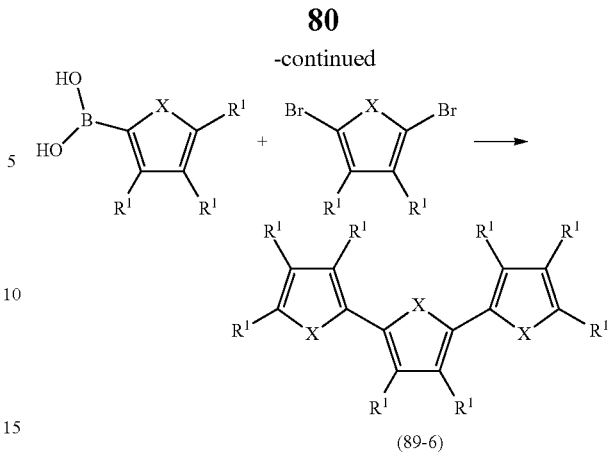

(89-6)

where $R^1$ and X have the same meaning as indicated above.

The following overview contains further procedures for the said compounds.

E1 EP 329752
E2 EP 4419932 B1 or WO 9103450 A1
E17 EP 1053578
E20 EP 440082
E24 EP 329752
E25 DE 3878450 and EP 334911
E28 JP H 06-264059 (A)
E29 EP 441932
E31 JP H 06-264059 (A)
H1 DE 19927627
H2 DE 19927627

Example 2

Quantum-Chemical Calculations

The HOMO (highest occupied molecular orbital) and LUMO (lowest unoccupied molecular orbital) positions as well as the triplet/singlet level and oscillator strength of organic compounds are determined via quantum-chemical calculations. To this end, the "Gaussian03W" program package (Gaussian Inc.) is used. In order to calculate organic substances without metals, firstly a geometry optimisation is carried out by means of the semi-empirical "Ground State/Semi-empirical/Default Spin/AM1" method (Charge 0/Spin Singlet). An energy calculation is subsequently carried out on the basis of the optimised geometry. In this, the "TD-SCF/DFT/Default Spin/B3PW91" method with the "6-31G (d)" base set (Charge 0/Spin Singlet) is used. The most important results are HOMO/LUMO levels, energies for the triplet and singlet ($S_1$) excited states and the oscillator strength (f). The first excited states ($S_1$ and $T_1$) are the most important here. S stands for the first excited singlet level and $T_1$ stands for the first excited triplet level. The energy calculation gives the HOMO HEh or LUMO LEh in hartree units. The HOMO and LUMO values in electron volts (eV) are determined therefrom as follows, where these relationships arise from the calibration with reference to cyclic voltammetry measurements (CV):

$$\text{HOMO(eV)}=((HEh*27.212)-0.9899)/1.1206$$

$$\text{LUMO(eV)}=((LEh*27.212)-2.0041)/1.385$$

For the purposes of this application, these values are to be regarded as the energetic position of the HOMO level or LUMO level of the materials. As an example, an HOMO of −0.21401 hartrees and an LUMO of −0.03463 hartrees are obtained from the calculation for compound Ref1 (see also Table 1), which a calibrated HOMO of −6.06 eV, a calibrated LUMO of −2.19 eV.

It is known to the person skilled in the art that the quantum-chemical calculations, as described here, can be employed very well for the said purposes. The calculations give results which correlate very well with experimentally determined data.

TABLE 1

Energy levels of Ref1, Ref2, E1-E34 and H1-H2

| Material | HOMO [eV] | LUMO [eV] | S1 [eV] | f |
|---|---|---|---|---|
| Ref1 | −6.06 | −2.19 | 4.31 | 0.08 |
| Ref2 | −6.08 | −2.13 | 4.24 | 0.03 |
| E1 | −6.15 | −2.27 | 4.11 | 1.00 |
| E2 | −6.38 | −2.49 | 4.20 | 0.90 |
| E3 | −6.21 | −2.24 | 4.30 | 1.05 |
| E4 | −6.47 | −2.48 | 4.04 | 0.93 |
| E6 | −6.01 | −2.00 | 4.24 | 0.73 |
| E7 | −6.30 | −2.25 | 4.26 | 0.82 |
| E8 | −6.48 | −2.14 | 4.22 | 0.56 |
| E9 | −5.73 | −2.32 | 3.91 | 0.74 |
| E10 | −5.73 | −2.34 | 3.90 | 0.82 |
| E11 | −6.51 | −2.20 | 4.24 | 0.35 |
| E12 | −6.04 | −2.17 | 4.18 | 0.58 |
| E13 | −5.81 | −2.05 | 4.17 | 0.65 |
| E14 | −6.17 | −2.42 | 3.92 | 0.92 |
| E15 | −6.09 | −2.12 | 4.42 | 0.35 |
| E16 | −5.73 | −2.27 | 3.98 | 1.14 |
| E17 | −5.99 | −2.11 | 4.06 | 0.05 |
| E20 | −6.46 | −2.52 | 4.19 | 0.80 |
| E21 | −6.04 | −2.21 | 4.20 | 1.00 |
| E22 | −6.47 | −2.53 | 4.19 | 0.94 |
| E23 | −6.49 | −2.55 | 4.18 | 0.94 |
| E24 | −6.09 | −2.25 | 4.23 | 1.08 |
| E25 | −6.15 | −2.33 | 4.20 | 1.04 |
| E26 | −6.25 | −2.34 | 4.21 | 1.11 |
| E27 | −6.27 | −2.52 | 4.17 | 0.92 |
| E28 | −6.28 | −2.38 | 4.21 | 0.94 |
| E29 | −6.27 | −2.42 | 4.20 | 0.93 |
| E30 | −6.28 | −2.35 | 4.21 | 1.00 |
| E31 | −6.33 | −2.41 | 4.20 | 0.88 |
| E32 | −6.68 | −2.68 | 3.82 | 0.61 |
| E33 | −6.01 | −2.18 | 4.14 | 0.23 |
| E34 | −6.39 | −2.49 | 3.88 | 0.30 |
| H1 | −6.51 | −2.19 | 4.26 | 0.02 |
| H2 | −6.51 | −2.19 | 4.26 | 0.02 |

Example 3

Solutions and Compositions

Solutions, as summarised in Table 2, are prepared as follows: firstly, the mixtures of host and emitter are dissolved in 10 ml of toluene and stirred until the solution is clear. The solution is filtered using a Millipore Millex LS, hydrophobic PTFE 5.0 μm filter.

TABLE 2

Composition of the solutions

| | Composition | Ratio (based on weight) | Concentration |
|---|---|---|---|
| Solution-Ref1 | Ref1 | 100% | 16 mg/ml |
| Solution-Ref2 | Ref2 | 100% | 16 mg/ml |
| Solution x* | PS:Ex | 70%:30% | 16 mg/ml | x is 1, 2, 3, . . . 34;
PS stands for polystyrene;

The solutions are used in order to coat the emitting layer of OLEDs. The corresponding solid composition can be obtained by evaporating the solvent from the solutions. This can be used for the preparation of further formulations.

Example 4

Production of the OLEDs

OLED-Ref1, OLED-Ref2, OLED1-OLED16 have the following structure: ITO/PEDOT/EML/cathode, where EML stands for the emission layer and ITO stands for the anode (indium tin oxide).

The OLEDs are produced using the corresponding solutions, as summarised in Table 2, in accordance with the following procedure:
1) Coating of 80 nm of PEDOT (Clevios™ P VP AI 4083) onto an ITO-coated glass substrate by spin coating; drying by heating at 180° C. for 10 min.
2) Coating of an 80 nm emitting layer by spin coating of one of the solution in accordance with Table 2.
3) Drying of the device by heating: 10 min at 180° C. for OLED-Ref1 and OLEd-Ref2; 30 min at 50° C. and then 30 min in vacuo for OLED1-16.
4) Vapour deposition of a Ba/Al cathode (3 nm/150 nm).
5) Encapsulation of the device.

Example 5

Characterisation of the OLEDs

Firstly photoluminescence spectra of the emission layer (EML) and subsequently electroluminescence spectra (EL) of the OLEDs obtained in this way are measured, since the EL spectrum gives the most important indications of a functioning electroluminescent device.

The EL spectra are measured by means of Ocean Optics UBS2000.

The EL spectra of OLED1-16 are summarised in FIG. 1-16. For the OLEDs comprising Ref1 and Ref2 as emitter, no EL spectra can be measured, even if the voltage is increased to 40 V. However, the OLEDs comprising emitters E1 to E16 according to the invention exhibit a clear EL spectrum having a significant proportion between 280 to 380 nm.

It is in fact very surprising that the emitters according to the invention have emitted in the UV region in an OLD having the simple layer structure indicated and comprising polystyrene as host. It is apparent that the person skilled in the art will be able to carry out further optimisations on the basis of the present invention and without inventive step.

Further improvements according to the invention are disclosed in the following examples.

Example 6

OLEDs Comprising Mixed Host

The use of a mixed host enables the OLED devices according to the invention to be improved further with respect to absolute intensity and operating voltage. To this end, OLED17 is produced analogously to the process described in Example 4. In contrast to OLED1, the composition PS (70 wt %):E1 (30 wt %) is not used for the EML for OLED17, but instead the composition PS (30 wt %):E4 (60 wt %):E1 (10 wt %) is used. E1 is employed as emitter here and E4 as host.

Figure 17:
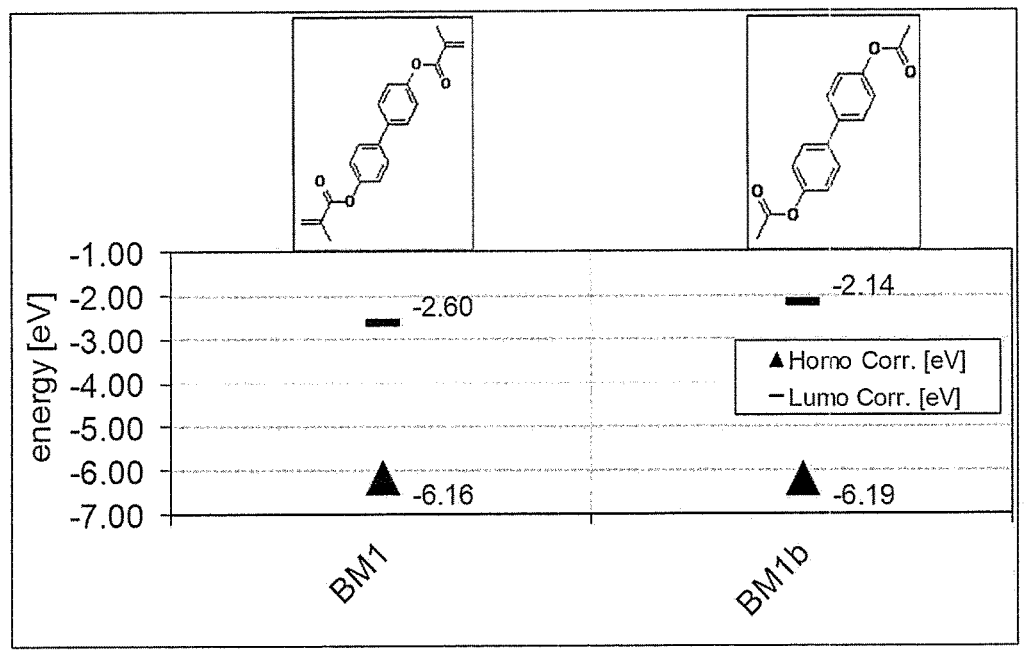
FIG. 17 shows results from quantum-chemical calculations on BM1 and BM1b.Abb.

FIG. 17 shows the EL spectra and operating voltages of OELD1 and OLED17 in comparison, where the absolute intensities have been standardised to the maximum of OLED17. It is clearly evident that the use of a mixed host consisting of PS and E4 enables the intensity of the UV OELD1 to be increased by a factor of about 4, where the operating voltage can be reduced at the same time.

Example 7

OLEDs with Blocking Layer

A further optimisation can be obtained through the use of a blocking layer. To this end, blocking material BM1 is employed. BM1 is a reactive mesogen which can be cross-linked with the aid of heating or UV radiation and can thereby form an insoluble network.

Figure 18:
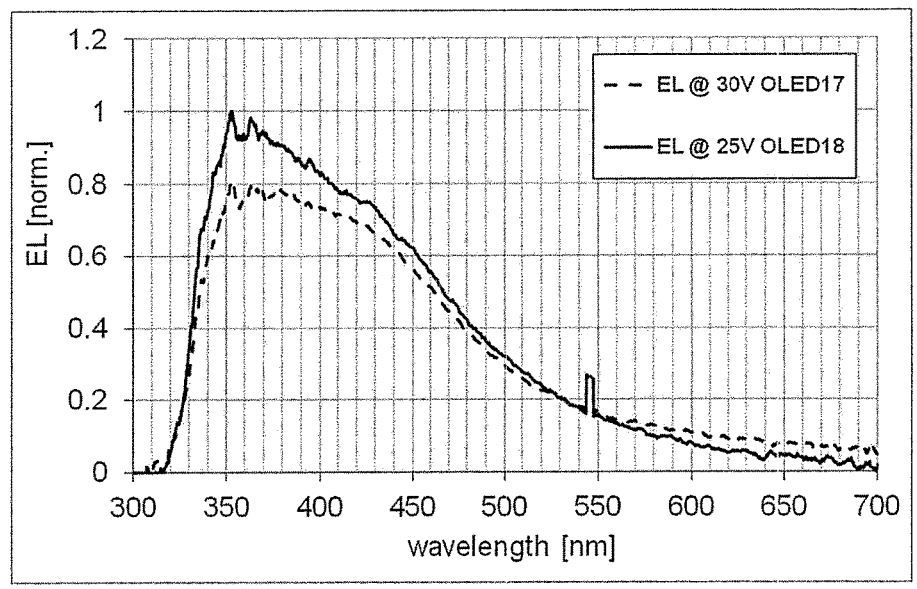
FIG. 18 shows the EL spectra and operating voltages of OLED17 (without blocking layer) and OLED18 (with blocking layer).

Firstly, quantum-chemical calculations on BM1 and BM1b (that is the effective component after the crosslinking reaction in the network; FIG. 18) are carried out. The $S_1$ level of BM1 is at 3.6 eV and that of BM1b is at 4.29 eV. The HOMOs and LUMOs of BM1 and BM1b are depicted in FIG. 18. BM1b has a relatively high LUMO level of −2.14 eV. The material is therefore suitable as exciton- and/or as electron-blocking material.

In order to check these theoretical considerations, the following experiment is carried out.
1) 20 nm of a layer consisting of BM1 is applied to a glass substrate by spin coating from a solution of BM1 in toluene having a concentration of 20 mg/ml;
2) the layer is dried by heating at 180° C. for 1 h in a glove box;
3) the layer is washed with toluene by spin coating;
4) the layer thickness is measured again. After the washing, a layer with a thickness of about 15 nm remains on the substrate.

OLED18 is subsequently produced as follows:
1) application of a layer of 80 nm of PEDOT (Clevios™ P VP AI 4083) to an ITO-coated glass substrate by spin coating, and drying by heating at 180° C. for 10 min.;
2) application of a 20 nm blocking layer by spin coating of a toluene solution of BM1 having a concentration of 20 g/ml;
3) drying of the blocking layer by heating: 60 min. at 180° C.;
4) washing of the blocking layer with toluene by spin coating;
5) application of an emitting layer with a thickness of 80 nm by spin coating of a toluene solution comprising a composition (PS (30 wt %):E4 (60 wt %):E1 (10 wt %)) having a concentration of 16 mg/ml;
6) drying of the device by heating: 30 min. at 50° C. and subsequently 30 min. in vacuo;
7) vapour deposition of a Ba/Al cathode (3 nm/150 nm);
8) encapsulation of the device.

Figure 19:
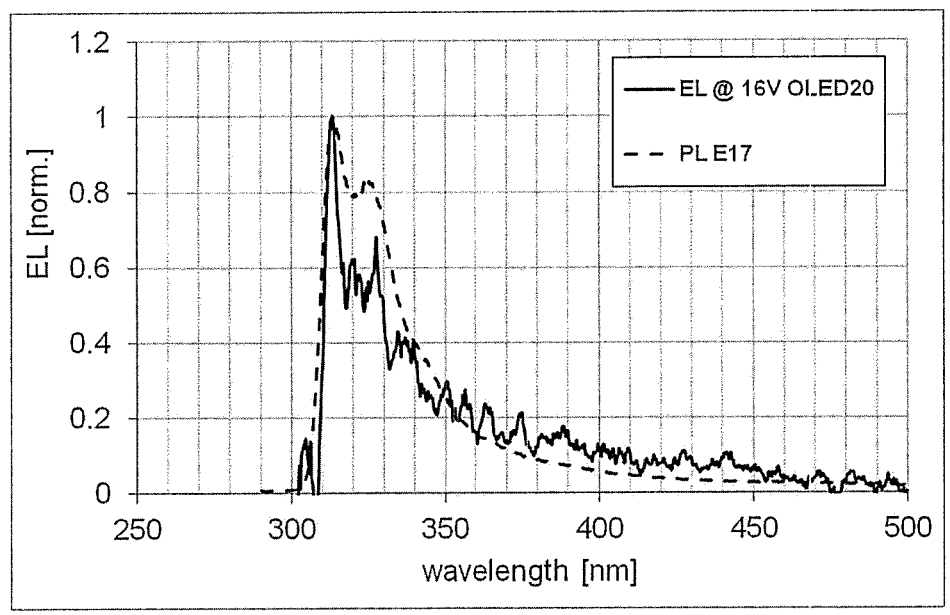
FIG. 19 shows the EL and PL spectrum of OLED20.

FIG. 19 shows the EL spectra and operating voltages of OLED17 (without blocking layer) and OLED18 (with blocking layer), where the absolute intensities are standardised to the maximum of OLED18. The figure shows a significant improvement of the properties of OLED18 compared with OLED17 with respect to intensity and operating voltage.

Example 8

OLEDs with Buffer Layer Having a High Work Function

Based on the technical teaching of the present invention, it is also possible to produce OLEDs which emit UV-B radiation (OLED20). To this end, a buffer layer having a higher work function is used (information from manufacturer "Heraeus Precious Metals GmbH & Co. KG", or see also Youn et al., J. Electrochem. Soc. 158, J321 (2011).

As comparison to OLED20, OLED19 is produced analogously to the process described in Example 4, where the EML has the composition PS (70 wt %):E17 (30 wt %)

OLED20 is produced as follows:
1) application of 80 nm of CLEVIOS™ HIL 1.3 to an ITO-coated glass substrate by spin coating with subsequent drying by heating at 180° C. for 10 min.;
2) application of an 80 nm layer as EML by spin coating of a toluene solution comprising the composition (PS (30 wt %):H1 (30 wt %):H2 (30 wt %):E17 (10 wt %)) in a concentration of 16 mg/ml;
3) drying of the device by heating: 30 min. at 50° C. and subsequently 30 min. in vacuo;
4) vapour deposition of a Ba/Al cathode (3 nm/150 nm).
5) encapsulation of the device.

Compared with Clevios™ P VP AI 4083, CLEVIOS™ HIL 1.3 has a significantly high work function, so that the injection of holes into the EML from the anode can be simplified.

For OLED19 comprising PS as host, the EL spectrum cannot be measured, even at an applied voltage of up to 40 V.

Figure 20:
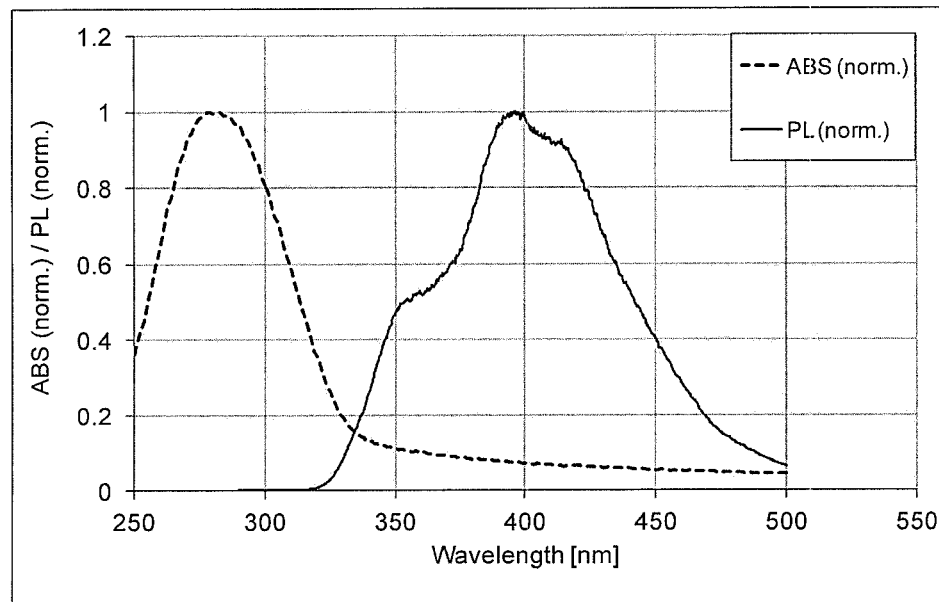
FIG. 20 shows the absorption and photoluminescence spectra of polymer P1.

FIG. 20 shows that OLED20 emits in the UV-B region at a low operating voltage of 16 V. The emission maximum is at about 312 nm. Other organic electroluminescent devices which emit UV-B radiation are not known.

Example 9

OLEDs Comprising Emitters E18 to E34

The PL spectra can be measured for emitters E18-E34. To this end, they are applied in a thin layer to quartz glass, where the thin layer is produced by spin coating of a corresponding solution in accordance with Table 2. All PL spectra exhibit an emission between 280 and 380 nm. On the basis of the technical teaching described above, person skilled in the art will be able, without inventive step, to produce electroluminescent devices which emit radiation in the UV region. Furthermore, the person skilled in the art will be able, without difficulties, to carry out further improvements by routine experiments on the technical teaching according to the invention. Thus, he will be able, for example, to use another co-matrix or an exciton-blocking layer or an anode or a substrate having improved UV transparency.

Example 10

Synthesis of Polymer P1

Polymer P1 is prepared from monomer units M1 and M2.

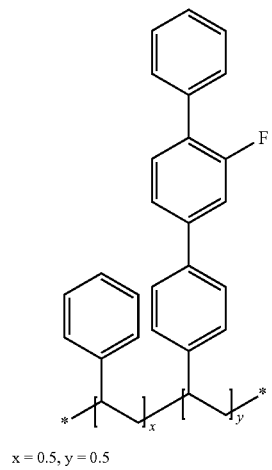

P1 x = 0.5, y = 0.5

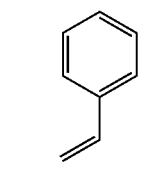

M1

CAS 100-42-5

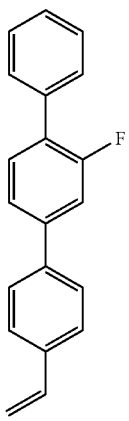

M2

Synthesis of M2

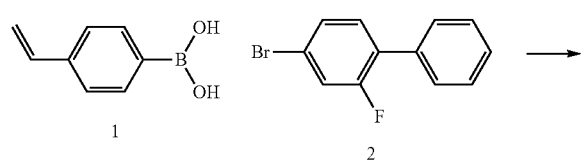

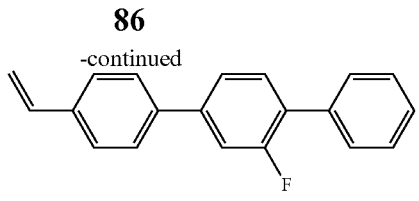

M2

Compound 1 (7.0 g, 47.3 mmol) and compound 2 (11.88 g, 47.3 mmol) are dissolved in 140 ml of dry 1,4-dioxane with stirring in a flask, PdCl$_2$(PCy)$_3$ (1.711 g, 2.3 mmol) is then added, and the reaction vessel is flushed with argon. Caesium fluoride (Aldrich 19, 832-3 (14.4 g, 94.7 mmol)) is added, and the reaction mixture is stirred at 100° C. for 12 hours. Water and dichloromethane are added to the reaction mixture, and the phases are separated. The aqueous phase is rinsed with dichloromethane. The combined organic phases are washed with saturated NaCl solution, subsequently dried over sodium sulfate, filtered and evaporated in a rotary evaporator.

Synthesis of P1

0.597 g (2.175 mmol) of 2'-fluoro-4"-vinyl-[1,1',4',1"]-terphenyl (M2) and 0.228 g (2.175 mmol) of styrene (M1) are transferred into a dried flask and rendered inert. 2.3 ml of degassed, dry toluene are added, and the solution is rendered inert a number of times. In a separate Schlenk vessel, 0.7 mg (0.004 mmol) of α,α'-azoisobutyronitrile are dissolved in 10 ml of dry, degassed toluene and rendered inert. The monomer solution is warmed to 70° C., and 0.1 ml of the AIBN solution is added to the reaction solution by means of a syringe. The reaction mixture is stirred at 70° C. for 72 h, then cooled to room temperature and stirred for a further 24 h. The reaction mixture is added dropwise to degassed ethanol, and the solid formed is filtered off. The solid is re-dissolved in toluene and precipitated in ethanol. The solid is filtered off and dried at 40° C. in a high vacuum for 24 h.

GPC measurement are measured with THF as eluent and o-dichlorobenzene as internal standard (1.2 m/l). The concentration of the analyte is 1000 g/l. The detection was carried out both by a diode array detector (250 nm), and also by a refractive index detector.

GPC Data:
Mn: 150,000 g/mol
Mw: 385,000 g/mol
PD: 2.6

Elemental Analysis:
C, 88.0%±0.2 (88.63% calculated)

Figure 21:
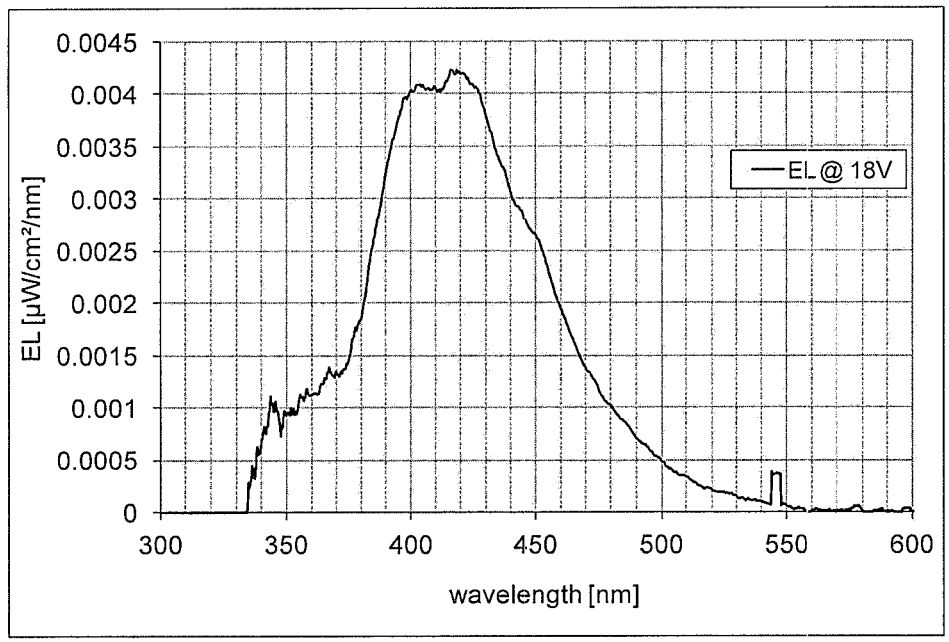
FIG. 21 shows the electroluminescence spectrum of OLED21.

The absorption and photoluminescence spectra of polymer P1 are measured by means of an 80 nm layer and shown in FIG. 21. P1 exhibits an emission in the UV region (peak around 350 nm) and a further component in the blue region of the spectrum.

Example 11

OLEDs Comprising Polymer P1

OLED21 and OELD22 are produced analogously to the process in Example 4, where the EML for OLED21 consists of 100% of P1, and the EML for OLED22 consists of a mixture of 90% of P1:10% of E9. Both EMLs are dried by heating at 180° C. for 10 min.

Figure 22:
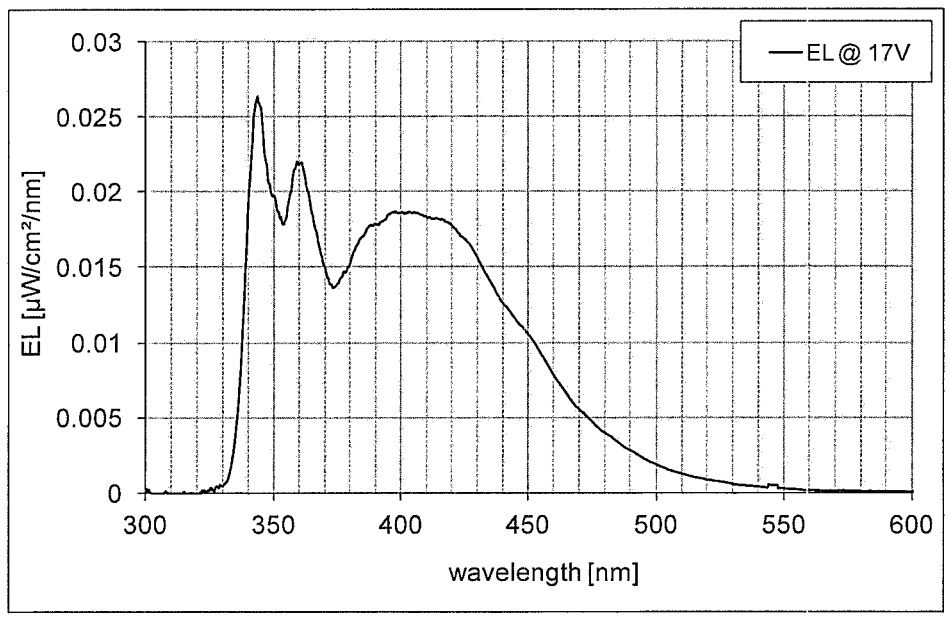
FIG. 22 shows the electroluminescence spectrum of OLED22.

FIG. 22 shows the electroluminescence spectrum of OLED21.

FIG. 23 shows the electroluminescence spectrum of OLED22.

Compared with OLEDs comprising small molecules, the P1-containing EML compositions of OLED21 and OELD22 exhibits improved solubility and an improved layer-formation property. Furthermore, the performance data of OLED21 and OLED22 are improved, in particular with respect to intensity, operating voltage and stability.

The invention claimed is:

1. An organic electroluminescent device comprising at least two electrodes and at least one light-emitting layer in between which comprises at least one organic compound, characterised in that the device emits radiation of a wavelength of 350 nm or smaller and wherein the at least one organic compound in the light-emitting layer is selected from the compound of the general formula (1)

$$Ar^1—Ar^2(-Ar^3)_n \qquad \text{formula (1)}$$

where the following applies to the symbols and indices used:

$Ar^1$, $Ar^2$ and $Ar^3$ are, identically or differently, five- or six-membered aromatic and/or heteroaromatic rings, which may in each case be substituted by one or more radicals $R^1$, which is optionally independent of one another;

n is 0 or 1;

$R^1$ is, identically or differently on each occurrence, H, D, F, $N(R^2)_2$, CN, $Si(R^2)_3$, $B(OR^2)_2$, $P(R^2)_2$, $S(=O)R^2$, a straight-chain alkyl, alkoxy or thioalkoxy group having 1 to 40 C atoms or a branched or cyclic alkyl, alkoxy, alkylalkoxy or thioalkoxy group having 3 to 40 C atoms, each of which is optionally substituted by one or more radicals $R^2$, where one or more non-adjacent $CH_2$ groups, is optionally replaced by $Si(R^2)_2$, $Ge(R^2)_2$, $Sn(R^2)_2$, C=O, C=S, C=Se, $C=NR^2$, SO, $SO_2$, $NR^2$, O, S or $CONR^2$, which is not bonded directly to ring of the formula (I), by $R^2C=CR^2$, C≡C or P(=O)($R^2$) and where one or more H atoms is optionally replaced by D, F, Cl, or CN, or an aromatic or heteroaromatic ring having 5 to 18 aromatic ring atoms, which may in each case be substituted by one or more radicals $R^2$, or a combination of two or more of these groups, two or more substituents $R^1$ here may also form a non-aromatic ring system with one another;

$R^2$ is, identically or differently on each occurrence, H, D, F, Cl, $N(R^3)_2$, CN, $Si(R^3)_3$, $B(OR^3)_2$, $C(=O)R^3$, $P(=O)(R^3)_2$, $S(=O)R^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which is optionally substituted by one or more radicals $R^3$, where one or more non-adjacent $CH_2$ groups is optionally replaced by $R^3C=CR^3$, C≡C, $Si(R^3)_2$, $Ge(R^3)_2$, $Sn(R^3)_2$, C=O, C=S, C=Se, $C=NR^3$, P(=O)($R^3$), SO, $SO_2$, $NR^3$, O, S or $CONR^3$ and where one or more H atoms is optionally replaced by D, F, Cl or CN, or an aromatic or heteroaromatic ring having 5 to 18 aromatic ring atoms, which may in each case be substituted by one or more radicals $R^3$, or a combination of two or more of these groups; two or more adjacent radicals $R^2$ here may form a non-aromatic ring system with one another;

$R^3$ is, identically or differently on each occurrence, H, D, F or an aliphatic, aromatic and/or heteroaromatic hydrocarbon radical having 1 to 18 C atoms, in which, in addition, one or more H atoms is optionally replaced by F; two or more substituents $R^3$ here may also form a non-aromatic mono- or polycyclic, aliphatic ring system with one another;

with the proviso that the compound of the formula (1) contains no condensed aromatic or condensed heteroaromatic ring systems, and with the proviso that the compound of the formula (1) contains no conjugated moiety containing more than 18 conjugated π (pi) electrons.

2. The device according to claim 1, wherein the radiation of a wavelength in the UV-B region of the spectrum.

3. The device according to claim 1, wherein the compound in the emitting layer has the general formula (18a) or (18b),

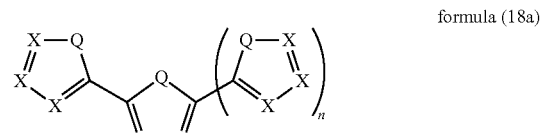

formula (18a)

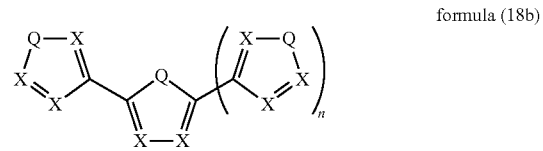

formula (18b)

wherein

X is on each occurrence, identically or differently, $CR^1$ or N;

Q is on each occurrence, identically or differently, X=X, $NR^1$, O, S or Se and n is equal to 0 or 1.

4. The device according to claim 1, wherein the compound in the emitting layer has one of the formulae (19) to (26)

formula (19)

formula (20)

formula (21)

formula (22)

formula (23)

formula (24)

-continued

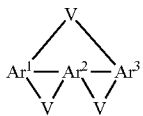

formula (25)

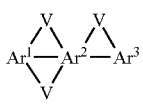

formula (26)

where the above definitions apply to $Ar^1$, $Ar^2$ and $Ar^3$ and where V is identical or different on each occurrence and stands for a non-aromatic bridge of the aromatic groups $Ar^1$ to $Ar^3$ and contains O, S, Se, N, Si, B, P and/or at least one $C(R^2)_2$ group.

5. The device according to claim 1, wherein the compound in the light-emitting layer contains no condensed rings.

6. The device according to claim 1, wherein $Ar^2$ is equal to the formula (87) and in that $Ar^1$ and $Ar^3$ are, identically or differently on each occurrence, of the formula (88)

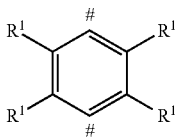

formula (87)

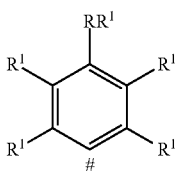

formula (88)

where $RR^1$ is H, F, Cl, CN, an alkyl or alkoxy group having 1 to 15 C atoms, where the groups is optionally unsubstituted or is optionally monosubstituted by $CF_3$, halogen, CN and where one or more $CH_2$ groups is optionally substituted by —O—, —S—, —$CF_2$O—, —$OCF_2$—, —OC—O— or —O—CO— in such a way that the O atoms are not connected directly to one another.

7. The device according to claim 1, wherein the compound in the emitting layer has the general formula (89-1)

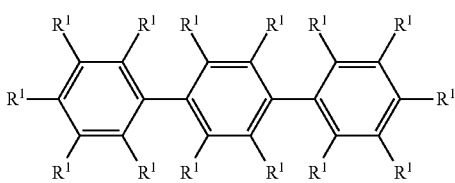

formula (89-1)

where a maximum of 4 of the radicals $R^1$ are not equal to H.

8. The device according to claim 1, wherein the organic compound in the light-emitting layer is employed as emitter and/or as host.

9. The device according to claim 1, wherein the device is a device from the group consisting of the organic light-emitting diodes (OLEDs), polymeric light-emitting diodes (PLEDs), organic light-emitting electrochemical cells (OLECs), organic light-emitting transistor (O-LETs) and organic light-emitting electrochemical transistor.

10. The device according to claim 1, wherein $Ar^1$, $Ar^2$ and $Ar^3$ have the general formula (2)

formula (2)

where the following applies to X and Q:
X is on each occurrence, identically or differently, $CR^1$ or N;
Q is on each occurrence, identically or differently, X=X, $NR^1$, O, S or Se.

11. The device according to claim 10, wherein Q is equal to X=X.

12. A method for the treatment of skin which comprises treating the skin by phototherapy using the device according to claim 1.

13. An organic electroluminescent device comprising at least two electrodes and at least one light-emitting layer in between which comprises at least one organic compound, characterised in that the device emits radiation of a wavelength of 350 nm or smaller and wherein the device comprises one or more additional layers between the electrodes, where the further layer(s) is:
a) an exciton-blocking layer which comprises an exciton-blocking material (blocking material) having a band gap of 3.6 eV or higher and/or
b) an electron-blocking layer which comprises an electron-blocking material (blocking material) having an LUMO of higher than −2.2 eV, and/or
c) a hole-blocking layer which comprises a hole-blocking material (blocking material) having an HOMO of lower than −6.0 eV.

14. The device according to claim 13, wherein the device is a device from the group consisting of the organic light-emitting diodes (OLEDs), polymeric light-emitting diodes (PLEDs), organic light-emitting electrochemical cells (OLECs), organic light-emitting transistor (O-LETs) and organic light-emitting electrochemical transistor.

15. The device according to claim 13, wherein the device comprises one or more additional layers between the electrodes, where the further layer(s) is:
a) an exciton-blocking layer which comprises an exciton-blocking material (blocking material) having a band gap of 3.8 eV or higher, and/or
b) an electron-blocking layer which comprises an electron-blocking material (blocking material) having an LUMO of higher than −2.1 eV, and/or
c) a hole-blocking layer which comprises a hole-blocking material (blocking material) having an HOMO of lower than −6.2 eV.

16. The device according to claim 15, wherein the device is a device from the group consisting of the organic light-emitting diodes (OLEDs), polymeric light-emitting diodes (PLEDs), organic light-emitting electrochemical cells (OLECs), organic light-emitting transistor (O-LETs) and organic light-emitting electrochemical transistor.

17. An organic electroluminescent device comprising at least two electrodes and at least one light-emitting layer in between which comprises at least one organic compound, characterised in that the device emits radiation of a wavelength of 350 nm or smaller and at least one polymer of the general formula (279)

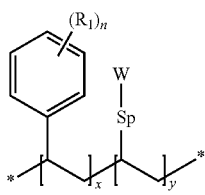

formula (279)

where the following applies to the indices and symbols used:
Sp is a single bond or a non-conjugated spacer;
W is, identically or differently on each occurrence, a structural unit of the formula (1), where the bonding between Sp and the compound of the formula (1) can take place at any desired and chemically possible position;
x is a number between 0 and 80 mol %;
y is a number from 2 to 100 mol %, where x+y=100 mol %;
n is an integer from 0 to 5;
$R_1$ is identically or differently on each occurrence, H, D, F or an aliphatic, aromatic and/or heteroaromatic hydrocarbon radical having 1 to 18 C atoms, in which, in addition, one or more H atoms is optionally replaced by F; two or more substituents $R^3$ here may also form a non-aromatic mono- or polycyclic, aliphatic ring system with one another.

18. The device according to claim 17, wherein the device is an organic light-emitting diode (OLED), a polymeric light-emitting diode (PLED), an organic light-emitting electrochemical cell (OLEC), an organic light-emitting transistor (O-LET) or an organic light-emitting electrochemical transistor.

19. A composition comprising at least one of the compounds of the formula (1)

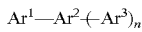

formula (1)

where the following applies to the symbols and indices used:
$Ar^1$, $Ar^2$ and $Ar^3$ are, identically or differently, five- or six-membered aromatic and/or heteroaromatic rings, which may in each case be substituted by one or more radicals $R^1$, which is optionally independent of one another;
n is 0 or 1;
$R^1$ is, identically or differently on each occurrence, H, D, F, $N(R^2)_2$, CN, $Si(R^2)_3$, $B(OR^2)_2$, $P(R^2)_2$, $S(=O)R^2$, a straight-chain alkyl, alkoxy or thioalkoxy group having 1 to 40 C atoms or a branched or cyclic alkyl, alkoxy, alkylalkoxy or thioalkoxy group having 3 to 40 C atoms, each of which is optionally substituted by one or more radicals $R^2$, where one or more non-adjacent $CH_2$ groups, is optionally replaced by $Si(R^2)_2$, $Ge(R^2)_2$, $Sn(R^2)_2$, C=O, C=S, C=Se, $C=NR^2$, SO, $SO_2$, $NR^2$, O, S or $CONR^2$, which is not bonded directly to ring of the formula (I), by $R^2C=CR^2$, C≡C or P(=O)($R^2$) and where one or more H atoms is optionally replaced by D, F, Cl, or CN, or an aromatic or heteroaromatic ring having 5 to 18 aromatic ring atoms, which may in each case be substituted by one or more radicals $R^2$, or a combination of two or more of these groups, two or more substituents $R^1$ here may also form a non-aromatic ring system with one another;
$R^2$ is, identically or differently on each occurrence, H, D, F, Cl, $N(R^3)_2$, CN, $Si(R^3)_3$, $B(OR^3)_2$, $C(=O)R^3$, $P(=O)(R^3)_2$, $S(=O)R^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which is optionally substituted by one or more radicals $R^3$, where one or more non-adjacent $CH_2$ groups is optionally replaced by $R^3C=CR^3$, C≡C, $Si(R^3)_2$, $Ge(R^3)_2$, $Sn(R^3)_2$, C=O, C=S, C=Se, $C=NR^3$, $P(=O)(R^3)$, SO, $SO_2$, $NR^3$, O, S or $CONR^3$ and where one or more H atoms is optionally replaced by D, F, Cl or CN, or an aromatic or heteroaromatic ring having 5 to 18 aromatic ring atoms, which may in each case be substituted by one or more radicals $R^3$, or a combination of two or more of these groups; two or more adjacent radicals $R^2$ here may form a non-aromatic ring system with one another;
$R^3$ is, identically or differently on each occurrence, H, D, F or an aliphatic, aromatic and/or heteroaromatic hydrocarbon radical having 1 to 18 C atoms, in which, in addition, one or more H atoms is optionally replaced by F; two or more substituents $R^3$ here may also form a non-aromatic mono- or polycyclic, aliphatic ring system with one another;
or at least one polymer of the formula (279)

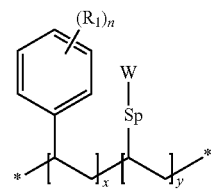

formula (279)

where the following applies to the indices and symbols used:
Sp is a single bond or a non-conjugated spacer;
W is, identically or differently on each occurrence, a structural unit of the formula (1), where the bonding between Sp and the compound of the formula (1) can take place at any desired and chemically possible position;
x is a number between 0 and 80 mol %;
y is a number from 2 to 100 mol %, where x+y=100 mol %;
n is an integer from 0 to 5;
$R_1$ is identically or differently on each occurrence, H, D, F or an aliphatic, aromatic and/or heteroaromatic hydrocarbon radical having 1 to 18 C atoms, in which, in addition, one or more H atoms is optionally replaced by F; two or more substituents $R^3$ here may also form a non-aromatic mono- or polycyclic, aliphatic ring system with one another;
and at least one organically material or organic semiconductor selected from the group of the emitters, host materials, matrix materials, electron-transport materials (ETM), electron-injection materials (EIM), hole-transport materials (HTM), hole-injection materials (HIM), electron-blocking materials (EBM), hole-blocking materials (HBM) and exciton-blocking materials (ExBM).

20. A formulation comprising the composition according to claim 19 and at least one solvent.

21. The composition according to claim 19, wherein the composition comprises at least one of the compounds of the formula (1).

* * * * *